(12) United States Patent
O'Brien et al.

(10) Patent No.: US 11,589,836 B2
(45) Date of Patent: *Feb. 28, 2023

(54) SYSTEMS AND METHODS FOR DETECTING NEUROLOGICAL CONDITIONS

(71) Applicant: NovaSignal Corp., Los Angeles, CA (US)

(72) Inventors: Michael O'Brien, Los Angeles, CA (US); Nicolas Canac, Los Angeles, CA (US); Michael Costa, Los Angeles, CA (US); Trevor Dunlop, Los Angeles, CA (US); Roman Flores, II, Los Angeles, CA (US); Robert Hamilton, Los Angeles, CA (US); Ilyas Patanam, Los Angeles, CA (US); Shankar Radhakrishnan, Los Angeles, CA (US); Mina Ranjbaran, Los Angeles, CA (US); Corey Thibeault, Los Angeles, CA (US); Samuel Thorpe, Los Angeles, CA (US); Seth Wilk, Los Angeles, CA (US); Jan Zwierstra, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 512 days.

This patent is subject to a terminal disclaimer.

(21) Appl. No.: 15/399,735

(22) Filed: Jan. 5, 2017

(65) Prior Publication Data

US 2017/0188992 A1 Jul. 6, 2017

Related U.S. Application Data

(60) Provisional application No. 62/275,192, filed on Jan. 5, 2016, provisional application No. 62/338,065, filed
(Continued)

(51) Int. Cl.
*A61B 8/08* (2006.01)
*A61B 8/06* (2006.01)
(Continued)

(52) U.S. Cl.
CPC .............. *A61B 8/4209* (2013.01); *A61B 8/06* (2013.01); *A61B 8/0808* (2013.01);
(Continued)

(58) Field of Classification Search
CPC . A61B 8/06; A61B 8/08–0816; A61B 8/0833; A61B 8/085; A61B 8/0891;
(Continued)

(56) References Cited

U.S. PATENT DOCUMENTS 3,841,308 A 10/1974 Tate
3,872,858 A 3/1975 Hudson et al.
(Continued)

FOREIGN PATENT DOCUMENTS

CN 104605889 A 5/2015
EP 0 403 807 A2 12/1990
(Continued)

OTHER PUBLICATIONS

International Search Report and Written Opinion dated Aug. 14, 2017, from international application No. PCT/US2017/029483.
(Continued)

*Primary Examiner* — Angela M Hoffa
(74) *Attorney, Agent, or Firm* — Foley & Lardner LLP

(57) ABSTRACT

According to various embodiments, there is provided a device including a processor configured to control a robotic system to autonomously position a transducer at a plurality of locations adjacent a subject's skull and to autonomously locate a window on the subject's skull within which an artery can be located, from which artery a signal can be
(Continued)

returned to the transducer, the signal having an energy level exceeding a predefined threshold.

22 Claims, 58 Drawing Sheets

Related U.S. Application Data on May 18, 2016, provisional application No. 62/347,527, filed on Jun. 8, 2016.

(51) Int. Cl.
*A61B 34/32* (2016.01)
*A61B 8/00* (2006.01)

(52) U.S. Cl.
CPC .......... *A61B 8/0891* (2013.01); *A61B 8/4218* (2013.01); *A61B 8/4444* (2013.01); *A61B 8/488* (2013.01); *A61B 8/5223* (2013.01); *A61B 8/585* (2013.01); *A61B 34/32* (2016.02); *A61B 8/486* (2013.01); *A61B 8/5276* (2013.01); *A61B 8/5292* (2013.01)

(58) Field of Classification Search
CPC ...... A61B 8/4461–4466; A61B 8/4777; A61B 8/488; A61B 8/5292; A61B 8/5276; A61B 8/5269; A61B 8/58; A61B 8/585; A61B 8/42–4227; A61B 8/4245–4263; A61B 34/30; A61B 34/32
See application file for complete search history.

(56) References Cited

U.S. PATENT DOCUMENTS

| | | | |
|---|---|---|---|
| 4,204,547 A | 5/1980 | Allocca |
| 4,205,687 A | 6/1980 | White et al. |
| 4,413,629 A | 11/1983 | Durley, III |
| 4,483,344 A | 11/1984 | Atkov et al. |
| 4,559,952 A | 12/1985 | Angelsen et al. |
| 4,759,374 A | 7/1988 | Kierney et al. |
| 4,815,705 A | 3/1989 | Kasugai et al. |
| 4,819,648 A | 4/1989 | Ko |
| 4,841,986 A | 6/1989 | Marchbanks |
| 4,930,513 A | 6/1990 | Mayo et al. |
| 4,951,653 A | 8/1990 | Fry et al. |
| 4,984,567 A | 1/1991 | Kageyama et al. |
| 5,040,540 A | 8/1991 | Sackner |
| 5,074,310 A | 12/1991 | Mick |
| 5,094,243 A | 3/1992 | Puy et al. |
| 5,156,152 A | 10/1992 | Yamazaki et al. |
| 5,197,019 A | 3/1993 | Delon-Martin et al. |
| 5,348,015 A | 9/1994 | Moehring et al. |
| 5,379,770 A | 1/1995 | Van Veen |
| 5,388,583 A | 2/1995 | Ragauskas et al. |
| 5,409,005 A | 4/1995 | Bissonnette et al. |
| 5,409,010 A | 4/1995 | Beach et al. |
| 5,411,028 A | 5/1995 | Bonnefous |
| 5,421,565 A | 6/1995 | Harkrader et al. |
| 5,514,146 A | 5/1996 | Lam et al. |
| 5,522,392 A | 6/1996 | Suorsa et al. |
| 5,526,299 A | 6/1996 | Coifman et al. |
| 5,617,873 A | 4/1997 | Yost et al. |
| 5,840,018 A | 11/1998 | Michaeli |
| 5,860,929 A | 1/1999 | Rubin et al. |
| 5,871,445 A | 2/1999 | Bucholz |
| 5,899,864 A | 5/1999 | Arenson et al. |
| 5,919,144 A | 7/1999 | Bridger et al. |
| 5,951,477 A | 9/1999 | Ragauskas et al. |
| 5,993,398 A | 11/1999 | Alperin |
| 6,027,454 A | 2/2000 | Low |
| 6,117,089 A | 9/2000 | Sinha |
| 6,120,446 A | 9/2000 | Ji et al. |
| 6,129,682 A | 10/2000 | Borchert et al. |
| 6,135,957 A | 10/2000 | Cohen-Bacrie et al. |
| 6,139,499 A | 10/2000 | Wilk |
| 6,200,267 B1 | 3/2001 | Burke |
| 6,231,509 B1 | 5/2001 | Johnson et al. |
| 6,261,231 B1 | 7/2001 | Damphousse et al. |
| 6,309,354 B1 | 10/2001 | Madsen et al. |
| 6,358,239 B1 | 3/2002 | Rake et al. |
| 6,364,869 B1 | 4/2002 | Bonaldo |
| 6,387,051 B1 | 5/2002 | Ragauskas et al. |
| 6,403,056 B1 | 6/2002 | Unger |
| 6,413,227 B1 | 7/2002 | Yost et al. |
| 6,423,003 B1 | 7/2002 | Ustuner et al. |
| 6,425,865 B1 | 7/2002 | Salcudean et al. |
| 6,454,715 B2 | 9/2002 | Teo |
| 6,488,717 B1 | 12/2002 | McColl et al. |
| 6,491,647 B1 | 12/2002 | Bridger et al. |
| 6,503,202 B1 | 1/2003 | Hossack et al. |
| 6,547,731 B1 | 4/2003 | Coleman et al. |
| 6,547,734 B2 | 4/2003 | Madsen et al. |
| 6,547,737 B2 | 4/2003 | Njemanze |
| 6,589,189 B2 | 7/2003 | Meyerson et al. |
| 6,618,493 B1 | 9/2003 | Torp et al. |
| 6,627,421 B1 | 9/2003 | Unger et al. |
| 6,653,825 B2 | 11/2003 | Munniksma |
| 6,656,125 B2 | 12/2003 | Misczynski et al. |
| 6,682,488 B2 | 1/2004 | Abend |
| 6,702,743 B2 | 3/2004 | Michaeli |
| 6,716,412 B2 | 4/2004 | Unger |
| 6,740,048 B2 | 5/2004 | Yost et al. |
| 6,746,422 B1 | 6/2004 | Noriega et al. |
| 6,875,176 B2 | 4/2005 | Mourad et al. |
| 6,887,199 B2 | 5/2005 | Bridger et al. |
| 6,955,648 B2 | 10/2005 | Mozayeni et al. |
| 7,122,007 B2 | 10/2006 | Querfurth |
| 7,128,713 B2 | 10/2006 | Moehring et al. |
| 7,147,605 B2 | 12/2006 | Ragauskas |
| 7,302,064 B2 | 11/2007 | Causevic et al. |
| 7,338,450 B2 | 3/2008 | Kristoffersen et al. |
| 7,403,805 B2 | 7/2008 | Abreu |
| 7,452,551 B1 | 11/2008 | Unger et al. |
| 7,534,209 B2 | 5/2009 | Abend et al. |
| 7,537,568 B2 | 5/2009 | Moehring |
| D594,127 S | 6/2009 | Causevic et al. |
| 7,547,283 B2 | 6/2009 | Mourad et al. |
| D603,051 S | 10/2009 | Causevic et al. |
| 7,674,229 B2 | 3/2010 | Hynynen et al. |
| 7,720,530 B2 | 5/2010 | Causevic |
| 7,771,358 B2 | 8/2010 | Moehring et al. |
| 7,815,574 B2 | 10/2010 | Mourad et al. |
| 7,854,701 B2 | 12/2010 | Stergiopoulos et al. |
| 7,857,763 B2 | 12/2010 | Tai |
| 7,904,144 B2 | 3/2011 | Causevic et al. |
| 7,912,269 B2 | 3/2011 | Ikeda et al. |
| 7,938,780 B2 | 5/2011 | Ragauskas et al. |
| 7,942,820 B2 | 5/2011 | Njemanze |
| D641,886 S | 7/2011 | Causevic et al. |
| 7,998,075 B2 | 8/2011 | Ragauskas et al. |
| RE42,803 E | 10/2011 | Lipson et al. |
| 8,036,856 B2 | 10/2011 | Pan et al. |
| 8,041,136 B2 | 10/2011 | Causevic |
| 8,062,224 B2 | 11/2011 | Ragauskas et al. |
| 8,075,488 B2 | 12/2011 | Burton |
| 8,109,880 B1 | 2/2012 | Pranevicius et al. |
| 8,162,837 B2 | 4/2012 | Moehring et al. |
| 8,206,303 B2 | 6/2012 | Ragauskas et al. |
| 8,211,023 B2 | 7/2012 | Swan et al. |
| 8,235,907 B2 | 8/2012 | Wilk et al. |
| 8,254,654 B2 | 8/2012 | Yen et al. |
| 8,265,291 B2 | 9/2012 | Bridger et al. |
| 8,353,853 B1 | 1/2013 | Kyle et al. |
| 8,364,254 B2 | 1/2013 | Jacquin et al. |
| 8,364,255 B2 | 1/2013 | Isenhart et al. |
| 8,366,627 B2 | 2/2013 | Kashif et al. |
| 8,391,948 B2 | 3/2013 | Causevic et al. |
| 8,394,024 B2 | 3/2013 | Miyama et al. |
| 8,394,025 B2 | 3/2013 | Ragauskas et al. |
| 8,414,539 B1 | 4/2013 | Kuracina et al. |
| 8,453,509 B2 | 6/2013 | Oberdorfer et al. |
| 8,473,024 B2 | 6/2013 | Causevic et al. |

(56) References Cited

U.S. PATENT DOCUMENTS

| | | |
|---|---|---|
| 8,603,014 B2 | 12/2013 | Alleman et al. |
| 8,613,714 B2 | 12/2013 | Alleman et al. |
| 8,622,912 B2 | 1/2014 | Chin et al. |
| 8,647,278 B2 | 2/2014 | Ji et al. |
| 8,706,205 B2 | 4/2014 | Shahaf et al. |
| 8,834,376 B2 | 9/2014 | Stergiopoulos et al. |
| 8,905,932 B2 | 12/2014 | Lovoi et al. |
| 8,926,515 B2 | 1/2015 | Ragauskas et al. |
| 8,998,818 B2 | 4/2015 | Pranevicius et al. |
| 9,005,126 B2 | 4/2015 | Beach et al. |
| 9,028,416 B2 | 5/2015 | De Viterbo |
| 9,042,201 B2 | 5/2015 | Tyler et al. |
| 9,066,679 B2 | 6/2015 | Beach et al. |
| 9,125,616 B2 | 9/2015 | Bredno et al. |
| 9,138,154 B2 | 9/2015 | Weinberg et al. |
| 9,192,359 B2 | 11/2015 | Flynn et al. |
| 9,196,037 B2 | 11/2015 | Jung |
| 9,630,028 B2 | 4/2017 | Browning et al. |
| RE46,614 E | 11/2017 | Lipson et al. |
| 10,709,417 B2* | 7/2020 | O'Brien .............. A61B 8/4444 |
| 11,090,026 B2* | 8/2021 | Hamilton .............. A61B 8/06 |
| 11,129,587 B2* | 9/2021 | Thorpe .............. A61B 8/0808 |
| 11,154,273 B2* | 10/2021 | O'Brien .............. A61B 8/0808 |
| 11,190,677 B2* | 11/2021 | Costa .............. H04N 5/2253 |
| 11,207,054 B2* | 12/2021 | Flores, II .............. A61B 8/4466 |
| 2001/0053879 A1 | 12/2001 | Mills et al. |
| 2002/0103436 A1 | 8/2002 | Njemanze |
| 2003/0050607 A1 | 3/2003 | Gagnieux et al. |
| 2004/0267127 A1 | 12/2004 | Abend et al. |
| 2005/0004457 A1 | 1/2005 | Moilanen et al. |
| 2005/0004468 A1 | 1/2005 | Abend et al. |
| 2005/0015009 A1 | 1/2005 | Mourad et al. |
| 2005/0049515 A1 | 3/2005 | Misczynski et al. |
| 2005/0119573 A1 | 6/2005 | Vilenkin et al. |
| 2005/0124901 A1 | 6/2005 | Misczynski et al. |
| 2005/0147297 A1 | 7/2005 | McLaughlin et al. |
| 2005/0148895 A1 | 7/2005 | Misczynski et al. |
| 2006/0025801 A1 | 2/2006 | Lulo et al. |
| 2006/0030777 A1 | 2/2006 | Liang et al. |
| 2006/0049721 A1 | 3/2006 | Kuehnicke |
| 2006/0173307 A1 | 8/2006 | Amara et al. |
| 2006/0173337 A1 | 8/2006 | Chen et al. |
| 2006/0184070 A1 | 8/2006 | Hansmann et al. |
| 2006/0206037 A1 | 9/2006 | Braxton |
| 2006/0241462 A1 | 10/2006 | Chou et al. |
| 2007/0016046 A1 | 1/2007 | Mozayeni et al. |
| 2007/0016050 A1 | 1/2007 | Moehring et al. |
| 2007/0078345 A1 | 4/2007 | Mo et al. |
| 2007/0161891 A1 | 7/2007 | Moore et al. |
| 2007/0232918 A1 | 10/2007 | Taylor |
| 2007/0239019 A1 | 10/2007 | Richard et al. |
| 2007/0244398 A1 | 10/2007 | Lo et al. |
| 2008/0015478 A1 | 1/2008 | Bose |
| 2008/0058861 A1 | 3/2008 | Cooper et al. |
| 2008/0065099 A1 | 3/2008 | Cooper et al. |
| 2008/0132790 A1 | 6/2008 | Burton |
| 2008/0208060 A1 | 8/2008 | Murkin |
| 2008/0262350 A1 | 10/2008 | Unger |
| 2009/0062813 A1 | 3/2009 | Prisco et al. |
| 2009/0074151 A1 | 3/2009 | Henderson et al. |
| 2009/0198137 A1 | 8/2009 | Ragauskas et al. |
| 2009/0264786 A1 | 10/2009 | Jacquin |
| 2009/0275836 A1 | 11/2009 | Fujii et al. |
| 2009/0287084 A1 | 11/2009 | Ragauskas et al. |
| 2009/0306515 A1 | 12/2009 | Matsumura et al. |
| 2009/0326379 A1 | 12/2009 | Daigle et al. |
| 2010/0016707 A1* | 1/2010 | Amara .............. A61B 5/02007 600/411 |
| 2010/0069757 A1 | 3/2010 | Yoshikawa et al. |
| 2010/0081893 A1 | 4/2010 | Jarvik et al. |
| 2010/0087728 A1 | 4/2010 | Jarvik et al. |
| 2010/0121192 A1 | 5/2010 | Nogata et al. |
| 2010/0125206 A1 | 5/2010 | Syme |
| 2010/0130866 A1 | 5/2010 | Main et al. |
| 2010/0274303 A1 | 10/2010 | Bukhman |
| 2010/0298821 A1 | 11/2010 | Garbagnati |
| 2011/0112426 A1 | 5/2011 | Causevic |
| 2011/0137182 A1 | 6/2011 | Bellezza et al. |
| 2011/0144518 A1 | 6/2011 | Causevic |
| 2011/0251489 A1 | 10/2011 | Zhang et al. |
| 2011/0275936 A1 | 11/2011 | Cho et al. |
| 2011/0301461 A1 | 12/2011 | Anite |
| 2012/0108967 A1 | 5/2012 | Weng et al. |
| 2012/0108972 A1 | 5/2012 | Miyama et al. |
| 2012/0123272 A1 | 5/2012 | Lam et al. |
| 2012/0123590 A1 | 5/2012 | Halsmer |
| 2012/0153580 A1 | 6/2012 | Soma |
| 2012/0157840 A1 | 6/2012 | Syme |
| 2012/0165675 A1 | 6/2012 | Syme |
| 2012/0165676 A1 | 6/2012 | Njemanze |
| 2012/0226163 A1 | 9/2012 | Moehring et al. |
| 2012/0238875 A1 | 9/2012 | Savitsky et al. |
| 2013/0006106 A1 | 1/2013 | O'Reilly et al. |
| 2013/0018277 A1 | 1/2013 | Liu |
| 2013/0047452 A1 | 2/2013 | McMurtry et al. |
| 2013/0080127 A1 | 3/2013 | Shahaf et al. |
| 2013/0197401 A1 | 8/2013 | Sato et al. |
| 2013/0239687 A1 | 9/2013 | Nakabayashi |
| 2013/0274607 A1 | 10/2013 | Anand et al. |
| 2014/0031690 A1 | 1/2014 | Toji et al. |
| 2014/0031693 A1 | 1/2014 | Solek |
| 2014/0081142 A1 | 3/2014 | Toma et al. |
| 2014/0081144 A1 | 3/2014 | Moehring et al. |
| 2014/0094701 A1 | 4/2014 | Kwartowitz et al. |
| 2014/0163328 A1 | 6/2014 | Geva et al. |
| 2014/0163379 A1 | 6/2014 | Bukhman |
| 2014/0171820 A1 | 6/2014 | Causevic |
| 2014/0194740 A1 | 7/2014 | Stein et al. |
| 2014/0276059 A1 | 9/2014 | Sheehan |
| 2014/0316269 A1 | 10/2014 | Zhang et al. |
| 2014/0323857 A1 | 10/2014 | Mourad et al. |
| 2014/0343431 A1 | 11/2014 | Vajinepalli et al. |
| 2015/0051489 A1 | 2/2015 | Caluser et al. |
| 2015/0065871 A1 | 3/2015 | Konofagou et al. |
| 2015/0065916 A1 | 3/2015 | Maguire et al. |
| 2015/0094582 A1 | 4/2015 | Tanaka et al. |
| 2015/0151142 A1 | 6/2015 | Tyler et al. |
| 2015/0157266 A1 | 6/2015 | Machon et al. |
| 2015/0190111 A1 | 7/2015 | Fry |
| 2015/0216500 A1 | 8/2015 | Mano et al. |
| 2015/0245771 A1 | 9/2015 | Wang et al. |
| 2015/0245776 A1 | 9/2015 | Hirohata et al. |
| 2015/0245820 A1 | 9/2015 | Tamada |
| 2015/0250446 A1 | 9/2015 | Kanayama |
| 2015/0250448 A1 | 9/2015 | Tamada |
| 2015/0297176 A1 | 10/2015 | Rincker et al. |
| 2015/0297177 A1 | 10/2015 | Boctor et al. |
| 2015/0302584 A1 | 10/2015 | Brauner et al. |
| 2015/0351718 A1 | 12/2015 | Vollmer et al. |
| 2015/0356734 A1 | 12/2015 | Ooga et al. |
| 2015/0359448 A1 | 12/2015 | Beach |
| 2016/0000367 A1 | 1/2016 | Lyon |
| 2016/0000411 A1 | 1/2016 | Raju et al. |
| 2016/0000516 A1 | 1/2016 | Cheng et al. |
| 2016/0030001 A1 | 2/2016 | Stein et al. |
| 2016/0094115 A1 | 3/2016 | Okawa et al. |
| 2016/0151618 A1 | 6/2016 | Powers et al. |
| 2016/0256130 A1 | 9/2016 | Hamilton et al. |
| 2016/0278736 A1 | 9/2016 | Hamilton et al. |
| 2016/0310006 A1 | 10/2016 | Aguero Villarreal et al. |
| 2016/0310023 A1 | 10/2016 | Chachisvilis et al. |
| 2016/0317129 A1 | 11/2016 | Seip et al. |
| 2016/0324585 A1 | 11/2016 | Noonan et al. |
| 2016/0367217 A1 | 12/2016 | Flores et al. |
| 2017/0119347 A1 | 5/2017 | Flores et al. |
| 2017/0188992 A1 | 7/2017 | O'Brien et al. |
| 2017/0188993 A1* | 7/2017 | Hamilton .............. A61B 8/4218 |
| 2017/0188994 A1 | 7/2017 | Flores et al. |
| 2017/0196465 A1 | 7/2017 | Browning et al. |
| 2017/0307420 A1 | 10/2017 | Flores et al. |
| 2018/0021021 A1 | 1/2018 | Zwierstra et al. |
| 2018/0093077 A1 | 4/2018 | Harding et al. |
| 2018/0103927 A1 | 4/2018 | Chung et al. |
| 2018/0103928 A1 | 4/2018 | Costa et al. |

(56) References Cited

U.S. PATENT DOCUMENTS

| | | | |
|---|---|---|---|
| 2018/0177487 A1 | 6/2018 | Deffieux et al. | |
| 2018/0214124 A1 | 8/2018 | O'Brien et al. | |
| 2018/0220991 A1* | 8/2018 | O'Brien | A61B 8/0891 |
| 2019/0150895 A1 | 5/2019 | Tian et al. | |

FOREIGN PATENT DOCUMENTS

| | | |
|---|---|---|
| EP | 1 750 804 | 2/2007 |
| EP | 2 034 901 | 3/2009 |
| EP | 2 111 787 | 10/2009 |
| EP | 2 858 619 | 4/2015 |
| FR | 2606625 A1 | 5/1988 |
| JP | S52-126979 A | 10/1977 |
| JP | H02-114008 | 4/1990 |
| JP | H05-143161 | 6/1993 |
| JP | H571763 U | 9/1993 |
| JP | 07-299066 A | 11/1995 |
| JP | 10-328189 A | 12/1998 |
| JP | 2003-225239 A | 8/2003 |
| JP | 2003-230558 A | 8/2003 |
| JP | 2003-245280 A | 9/2003 |
| JP | 2004-237082 A | 8/2004 |
| JP | 2006-025904 A | 2/2006 |
| JP | 2007-143704 A | 6/2007 |
| JP | 2010-500084 A | 1/2010 |
| JP | 2010-200844 A | 9/2010 |
| JP | 2013-503681 A | 2/2013 |
| JP | 2015-533299 A | 11/2015 |
| WO | WO-95/02361 | 1/1995 |
| WO | WO-99/56625 | 11/1999 |
| WO | WO-2009/138882 A2 | 11/2009 |
| WO | WO-2010/042146 | 4/2010 |
| WO | WO-2013/155537 | 10/2013 |
| WO | WO-2014/070993 A1 | 5/2014 |
| WO | WO-2015/073903 A1 | 5/2015 |
| WO | WO-2015/092604 | 6/2015 |
| WO | WO-2016/001548 | 1/2016 |

OTHER PUBLICATIONS

Chatelain et al. "Confidence-Driven Control of an Ultrasound Probe: Target-Specific Acoustic Window Optimization." IEEE ICRA May 16-21, 2016, pp. 3441-3446.

Chatelain et al. "Optimization of ultrasound image quality via visual servoing." IEEE INCRA May 26-30, 2015, pp. 5997-6002.

International Preliminary Report on Patentability dated Jul. 19, 2018, from application No. PCT/US2017/012395.

Japanese Office Action dated Apr. 24, 2018, from application No. 2016-554529.

Mckinnon et al. "Long-Term Ambulatory Monitoring for Cerebral Emboli Using Transcranial Doppler Ultrasound." Stroke(35), 2004; pp. 73-78.

Nadeau et al. "Intensity-Based Ultrasound Visual Servoing: Modeling and Validation with 2-D and 3-D Probes." IEEE Trans on Robotics (29:4), Aug. 2013, pp. 1003-1015.

Non-Final Office Action dated Jun. 27, 2018, from U.S. Appl. No. 15/942,368.

Qiu et al., "A Robotic Holder of Transcranial Doppler Probe for CBFV Auto-Searching." Proc of IEEE ICIA, Aug. 2013, pp. 1284-1289.

Souza-Daw et al. "Towards Ultrasonic Detection of Acoustic Windows forTranscranial Doppler Ultrasound and related Procedures." IEEE Proc INDS' 11 & ISTET'11. Jul. 25-27, 2011. 6 pages.

International Search Report and Written Opinion dated Jun. 1, 2017, from application No. PCT/IB2017/050349.

International Search Report and Written Opinion dated Jun. 8, 2017, from application No. PCT/US2017/012402.

Tatasurya, Samuel Radiant, "Multimodal Graphical User Interface for Ultrasound Machine Control via da Vinci Surgeon Console: Design, Development, and Initial Evaluation," The University of British Columbia, Vancouver, Aug. 2015, p. 33, paragraph 1.

International Search Report and Written Opinion dated May 4, 2017, from application No. PCT/US2017/012395.

International Search Report and Written Opinion dated Oct. 13, 2016, from related international application No. PCT/US2016/038433.

M.H. Raibert et al., "Hybrid Position/Force Control of Manipulators", Journal of Dynamic Systems, Measurement, and Control, vol. 102, Jun. 1981, pp. 126-133, abstract.

International Preliminary Report on Patentability dated Dec. 28, 2017, from international application No. PCT/US2016/038433.

Extended European Search Report dated Jul. 16, 2019, from application No. 17736353.8.

Extended European Search Report dated Jul. 19, 2019, from application No. 17736375.1.

Extended European Search Report dated Jul. 24, 2019, from application No. 17735919.7.

Aaslid, R., et al., "Noninvasive transcranial Doppler ultrasound recording of flow velocity in basal cerebral arteries", Journal of Neurosurgery, 1982, 57(6): p. 769-774.

Baldwin, K., et al., "Subpeak Regional Analysis of Intracranial Pressure Waveform Morphology based on Cerebrospinal Fluid Hydrodynamics in the Cerebral Aqueduct and Prepontine Cistern", 34th Annual International Conference of the IEEE EMBS, 2012, p. 3935-3938.

Bashford, G., et al.."Monitoring Cerebral Hemodynamics with Transcranial Doppler Ultrasound during Cognitive and Exercise Testing in Adults following Unilateral Stroke", 34th Annual International Conference of the IEEE EMBS, 2012, p. 2310-2313.

Chen, W., et al., "Intracranial Pressure Level Prediction in Traumatic Brain Injury by Extracting Features from Multiple Sources and Using Machine Learning Methods", 2010 IEEE International Conference on Bioinformatics and Biomedicine, 2010, p. 510-515.

Cheng, Y. & Zhao, R., "Self-training classifier via local learning regularization", Proceedings of the Eighth International Conference on Machine Learning and Cybernetics, 2009, p. 454-459.

Ekroth, R., et al., "Transcranial Doppler-estimated versus thermodilution estimated cerebral blood flow during cardiac operations. Influence of temperature and arterial carbon dioxide tension." Journal Thoracic Cardiovascular Surgery, 1991, 102(1): p. 95-102.

Extended European Search Report dated Jan. 4, 2019, from application No. 16812644.9.

Gomez, C., et al., Transcranial Doppler Ultrasonographic Assessment of Intermittent Light Stimulation at Different Frequencies, Stroke, 1990, 21, p. 1746-1748.

Harrison, M. & Markus, H., "Estimation of cerebrovascular reactivity using transcranial Doppler, including the use of breath-holding as the vasodilatory stimulus", Stroke, 1992, 23(5) p. 668-73.

International Preliminary Reporton Patentability dated Jul. 19, 2018, from application No. PCT/IB2017/050349.

International Preliminary Reporton Patentability dated Jul. 19, 2018, from application No. PCT/US2017/012365.

International Preliminary Reporton Patentability dated Jul. 19, 2018, from application No. PCT/US2017/012402.

International Preliminary Reporton Patentability dated Nov. 8, 2018, from application No. PCT/US2017/029483.

Jaffres, P., et al., "Transcranial Doppler to detection admission patients at risk for neurological deterioration following mild and moderate brain trauma", Intensive Care Med, 2005, 31 (6): p. 785-790.

Japanese Decision of Rejection dated Dec. 18, 2018, from application No. 2016-554529.

Japanese Office Action dated Aug. 28, 2018, from application No. 2016-554529.

Len, T.K., et al., "Cerebrovascular reactivity impairment after sport-induced concussion", Med Sci Sports Exerc, 2011, 43(12): p. 2241-2248.

Uguz, H., "A hybrid system based on information gain and principal component analysis forthe classification of transcranial Doppler signals", Computer Methods and Programs in Biomedicine, 2010, 107(2012) p. 598-609.

Zhu, X., "Semi-supervised Learning Literature Survey", Computer Sciences TR 1530, University of Wisconsin—Madison, 2008.

(56) References Cited

OTHER PUBLICATIONS

Chinese Office Action dated Mar. 24, 2020, from application No. 201680034144.6.
Extended European Search Report dated Nov. 12, 2019, from application No. 17736371.0.
Extended European Search Report dated Nov. 21, 2019, from application No. 17790294.7.
Final Office Action dated Jan. 30, 2020, from U.S. Appl. No. 15/497,039.
Japanese Office Action dated Jan. 27, 2020, from application No. 2018-534127.
Non-Final Office Action dated Dec. 11, 2019, from U.S. Appl. No. 15/399,710.
Non-Final Office Action dated Nov. 19, 2019, from U.S. Appl. No. 15/399,648.
Notice of Allowance dated Dec. 9, 2019, from U.S. Appl. No. 15/399,440.
Qiu, et al., "A Robotic Holder of Transcranial Doppler Probe for CBFV Auto-Searching", 2013 IEEE International Conference on Information and Automation (ICIA), IEEE, Aug. 26, 2013, pp. 1284-1289.
Notice of Allowance dated Mar. 4, 2020, from U.S. Appl. No. 15/942,368.
Chinese Office Action dated Aug. 27, 2020, from application No. 201780005528.X.
Final Office Action dated Jun. 9, 2020, from U.S. Appl. No. 15/399,648.
Non-Final Office Action dated Jul. 16, 2020, from U.S. Appl. No. 15/497,039.
Final Office Action dated Apr. 23, 2021, from U.S. Appl. No. 15/187,397.
Japanese Office Action dated Mar. 11, 2021, from application No. 2018-555541.
Notice of Allowance dated Mar. 19, 2021, from U.S. Appl. No. 15/399,710.
Chinese Office Action dated Sep. 23, 2020, from application No. 201780005865.9.
Final Office Action dated Sep. 18, 2020, from U.S. Appl. No. 15/399,710.
Japanese Office Action dated Dec. 10, 2020, from application No. 2018-534916.
Japanese Office Action dated Nov. 5, 2020, from application No. 2018-534904.
Japanese Office Action dated Oct. 22, 2020, from application No. 2018-534131.
Non-Final Office Action dated Oct. 28, 2020, from U.S. Appl. No. 15/187,397.
Chinese Office Action dated Jun. 30, 2020, from application No. 201780005447.X.
Chinese Office Action dated Aug. 18, 2020, from application No. 201780005508.2.
European Office Action dated Sep. 24, 2021, from application No. 17735919.7.
European Office Action dated Sep. 28, 2021, from application No. 17736375.1.
Notice of Allowance dated Aug. 24, 2021, from U.S. Appl. No. 15/187,397.
US Notice of Allowance dated May 27, 2022, from U.S. Appl. No. 16/847,247.

\* cited by examiner

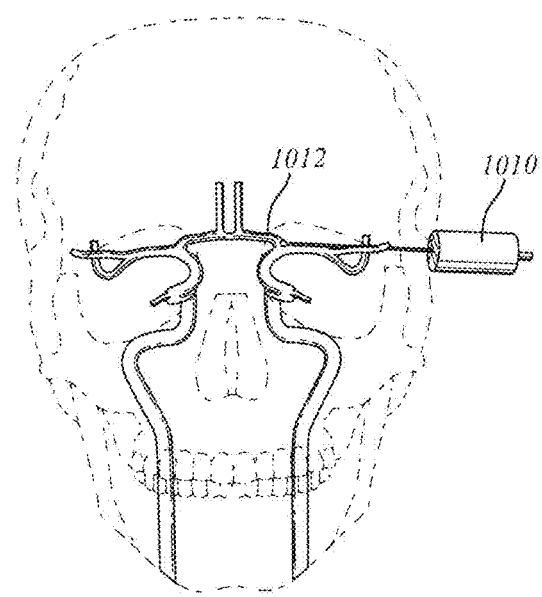
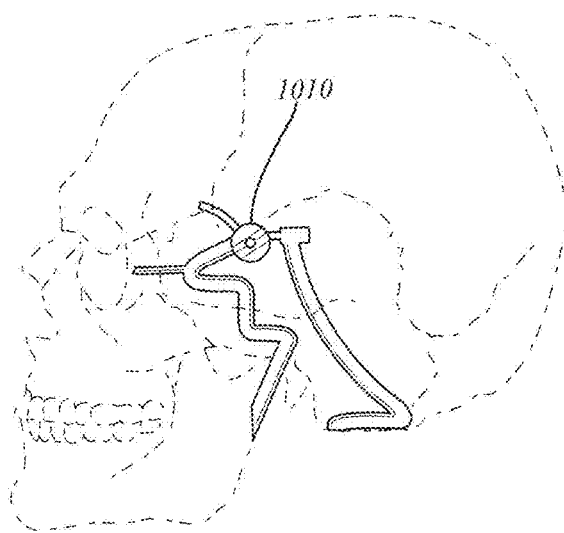
Fig. 16A
Fig. 16B
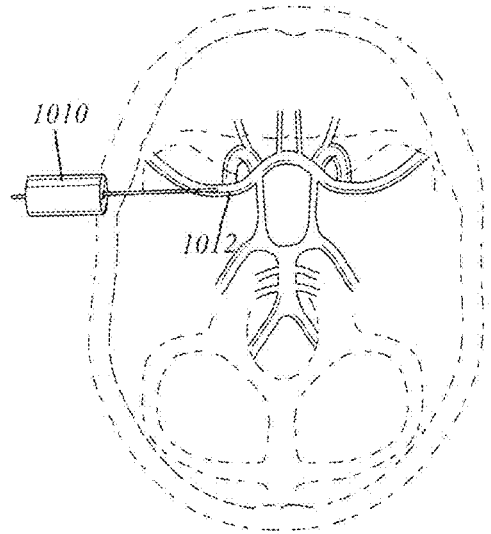
Fig. 16C

SYSTEMS AND METHODS FOR DETECTING NEUROLOGICAL CONDITIONS

CROSS-REFERENCE TO RELATED PATENT APPLICATIONS

The present disclosure claims priority to, and the benefit of, U.S. provisional patent application Ser. No. 62/275,192, titled SYSTEMS AND METHODS FOR DETECTING NEUROLOGICAL CONDITIONS, and filed on Jan. 5, 2016, which is incorporated herein by reference in its entirety. The present disclosure claims priority to, and the benefit of, U.S. provisional patent application Ser. No. 62/338,065, titled REMOTE CENTER OF COMPLIANCE PROBE DEVICE, and filed on May 18, 2016, which is incorporated herein by reference in its entirety. The present disclosure claims priority to, and the benefit of, U.S. provisional patent application Ser. No. 62/347,527, titled PROBE SUPPORT STRUCTURE WITH VARIABLE STIFFNESS, and filed on Jun. 8, 2016, which is incorporated herein by reference in its entirety.

FIELD

Subject matter described herein relates generally to medical devices, and more particularly to a headset including a transducer for diagnosing medical conditions.

BACKGROUND

Traumatic brain injuries (TBI) affect millions of patients each year worldwide. Cerebral hemodynamic dysfunction is common following TBI, potentially resulting in catastrophic neurologic sequelae, including long-term disability and even death. Current diagnosis and management methods are limited to hospital settings (transcranial Doppler ultrasonography—TCD, CT, MRI, etc.). Accordingly, there is a need for developing a medical device that can provide clinical utility of hospital-based assessment methods outside of a hospital for rapid and reliable assessment using disruptive innovations in TCD ultrasonography.

Various sensory modalities are currently used in major hospitals for the assessment of cerebral hemodynamics within the Circle of Willis arteries of the brain, including TCD ultrasound, transcranial color-coded sonography (TCCS), phased arrays, and functional Near-Infrared Spectroscopy (fNIRS). These modalities emit energy capable of penetrating windows in the skull. Acquiring the cerebral blood flow velocity (CBFV) signals using such sensory modalities, however, requires the placement of a transducer within a specific region of the skull thin enough for the ultrasound waves to penetrate. For example, it is known that a thin skull region often exists superior to the patient's zygomatic arch (transtemporal). Other windows often exist at the suboccipital, transorbital, submandibular portions of the skull. The location of these narrow windows, however, varies significantly from person to person based on facial features, and even race or gender. This variation makes insonating—exposing to ultrasound—the desired blood vessel difficult. This difficulty has often restricted TCD use, and other modalities, to major hospitals who engage expert sonographers to operate the device.

TCD specifically has been widely used clinically since the 1980s to measure CBFV within the major conducting arteries and veins of the brain (Circle of Willis). It is currently used in the diagnosis and monitoring a number of neurologic conditions, including the assessment of arteries after a subarachnoid haemorrhage (SAH) for vasospasm, aiding preventative care in children with sickle cell anemia, and risk assessment in embolic stroke patients. TCD utilizes the Doppler effect by emitting ultrasound frequencies typically between 1.6 MHz and 4 MHz and measuring the shift in frequency upon reflection from non-stationary tissue (red blood cells), which are converted to velocity. Depth information within the biologic tissue is controlled by time delays between emitting and receiving of the ultrasound waves.

Fully automating TCD use would not only remove the need for an expert technician but also open the technology up to a broader range of clinical indications. As such, there is a need for developing a portable, fully automated system to determine appropriate window locations.

Existing semi-automated diagnosis methods typically use two degree of freedom robotic mechanisms that can only reorient the TCD probe with pan and tilt rotations, emitting energy into the skull and then analyzing the return signals, but are otherwise unable to traverse portions of the skull in X and Y directions. All existing semi-automated methods require a knowledgeable user to place the robotic mechanism on an existing window. If such an existing mechanism is not placed on an existing window, useful data will not be returned. Some existing two degree of freedom mechanisms will not always find a signal, when they do, it often takes a trained technician to determine the location of appropriate windows and the best signals. Further, some existing mechanisms are not capable of constructing a map of blood vessels in the brain. As such, there exists a need to develop a fully automated robotic system that does not require user feedback to locate appropriate windows and is capable of constructing a map of blood vessels in the brain more quickly than current solutions.

SUMMARY

According to some embodiments, there is provided a head-mounted medical device that can automatically search, locate and acquire a stable CBFV waveform from any human being's temporal window, independent of his or her age, size, shape, or demography in an acceptable period of time (e.g., under five minutes). By automating the process of acquiring TCD signals, or other sensory modalities, using a robotic transducer positioning system that uses prior knowledge of the head anatomy for rapid signal discovery and locking, embodiments can vastly expand the clinical utility of TCD to settings outside of hospitals. Furthermore, embodiments can function with existing TCD systems. Embodiments enable on-site, rapid diagnosis of TBI.

According to various embodiments, there is provided a device, including a processor configured to control a robotic system to autonomously position a transducer at a plurality of locations adjacent a subject's skull and to autonomously locate a window on the subject's skull within which an artery can be located, from which artery a signal can be returned to the transducer, the signal having an energy level exceeding a predefined threshold. In some embodiments, the processor is further configured to cause the robotic system to autonomously locate within the window an ultrasonic signal representative of blood flow within an artery, the signal having an energy level exceeding a predefined threshold. In some embodiments, the processor is further configured to record in a database a plurality of locations of the transducer as the robotic system autonomously positions the transducer. In some embodiments, the processor is further configured to record in a database a plurality of energy levels of signals as the robotic system autonomously positions the transducer. In some embodiments, the processor is further configured to record in a database a plurality of locations of the transducer as the robotic system autonomously positions the transducer. In some embodiments, the processor is further configured to record in a database a plurality of energy levels of signals as the robotic system autonomously positions the transducer. In some embodiments, the processor is further configured to execute a search algorithm stored on non-transitory computer readable media. In some embodiments, the device further includes a robotic mechanism configured to move the transducer in multiple axes, and the search algorithm is further configured to control pan, tilt, and Z axis positions of the robotic mechanism. In some embodiments, the device includes a database of seed points stored on non-transitory computer readable media accessible by the processor, which database of seed points is used by the processor. In some embodiments, the device further includes a database of previously measured locations stored on non-transitory computer readable media accessible by the processor, which database of previously measured locations is used by the processor. In some embodiments, the processor is configured to execute a search algorithm, the search algorithm being configured to use dynamic dwell time at a plurality of locations searched. In some embodiments, the robotic system further includes a five degree of freedom robotic mechanism. In some embodiments, the robotic system further includes a five degree of freedom robotic mechanism configured to move the transducer in multiple axes simultaneously. In some embodiments, further includes a robotic headset within which the transducer is mounted. In some embodiments, the processor is further configured to cause the robotic system to build a vascular map of the brain inside the subject's skull. In some embodiments, the transducer is an ultrasound probe.

According to various embodiments, there is provided a robotic imaging device, including a transducer, a processor in communication with the transducer, the processor configured to receive and process data from the transducer, a robotic mechanism controlled by the processor configured to move the transducer to scan for and locate a window in a skull of a subject, and wherein the processor is configured to autonomously control the robotic mechanism to search for and locate a TCD signal within a window in the skull of the subject, said TCD signal having an energy level exceeding a predefined threshold. In some embodiments, the processor is further configured to execute a search algorithm stored on non-transitory computer readable media. In some embodiments, the processor is further configured to execute a search algorithm stored on non-transitory computer readable media, which search algorithm employs dynamic dwell time at a plurality of search locations. In some embodiments, the robotic mechanism is further configured to use a visual window guide used for initial registration. In some embodiments, the robotic mechanism is further configured to move in at least two axes simultaneously. In some embodiments, the robotic mechanism is further configured to include a five degree of freedom robotic mechanism configured to move the transducer in multiple axes simultaneously. In some embodiments, the robotic mechanism is further configured to include a six degree of freedom robotic mechanism. In some embodiments, the robotic mechanism is further configured to include at least a four degree of freedom robotic mechanism. In some embodiments, the device further includes a feedback mechanism used to adjust location due to subject movement.

According to various embodiments, there is provided a method for locating an artery in a subject's brain, including the steps of controlling a processor to autonomously locate a window of a subject's skull, and within the window of the subject's skull, to autonomously locate a first ultrasonic signal representative of blood flow within an artery, the first ultrasonic signal having an energy level exceeding a predefined threshold. In some embodiments, the method further includes a step of moving and autonomously locating a second signal representative of blood flow within an artery, the second signal having an energy level exceeding a predefined threshold.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 16A illustrates TCD sensor placement for insonating the middle cerebral artery (MCA).

FIG. 16B illustrates TCD sensor placement for insonating the middle cerebral artery (MCA).

FIG. 16C illustrates TCD sensor placement for insonating the middle cerebral artery (MCA).

DETAILED DESCRIPTION

Figure 1A:
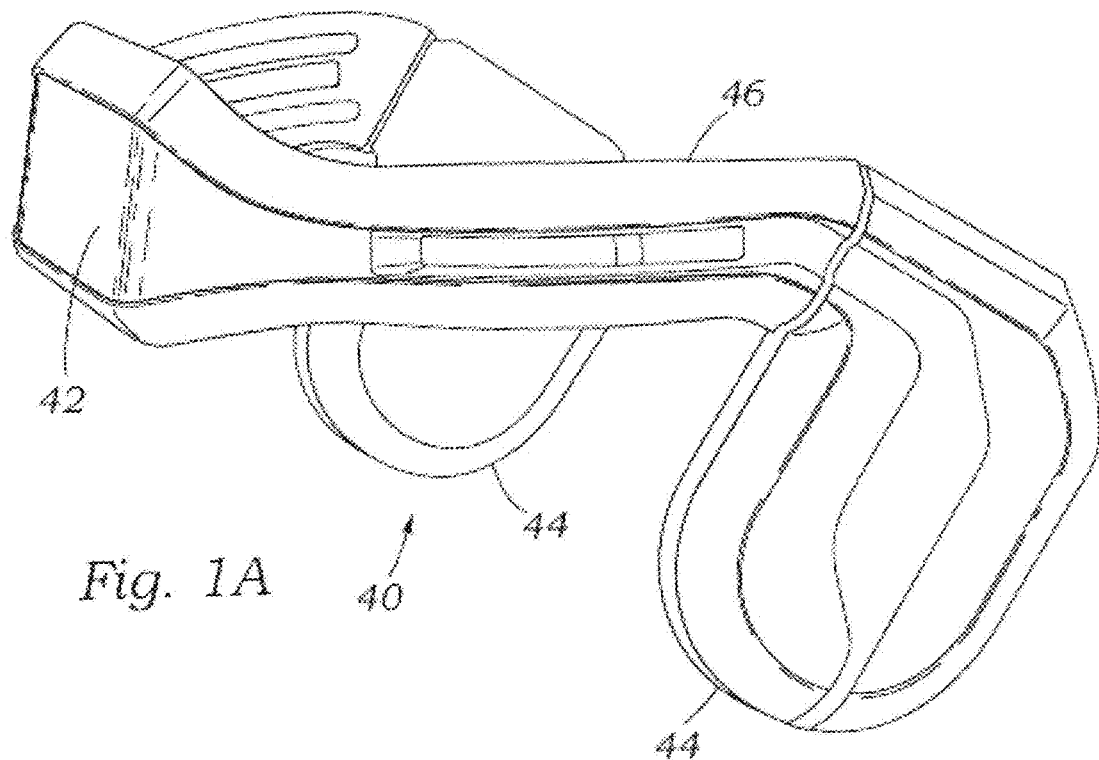
FIG. 1A is a perspective view of an ergonomic headband.

In the following description of various embodiments, reference is made to the accompanying drawings which form a part hereof and in which are shown by way of illustration specific embodiments in which the embodiments may be practiced. It is to be understood that other embodiments may be utilized, and structural changes may be made without departing from the scope of the various embodiments disclosed in the present disclosure.

Some of the likely beneficiaries of this technology include emergency room, acute care centers, general practice physicians, first responders, and other health care professionals (athletic trainers). They will benefit from the ability to rapidly diagnose and monitor head injury.

For first responders and untrained technicians, various embodiments provide a robotic TCD system or robotic mechanism that is fully automated, enabling accurate and rapid diagnoses and management TBIs, strokes, and other neurological conditions. Embodiments may leverage other technologies for machine learning algorithms that enable neurological conditions diagnoses based on subtle CBFV waveform changes. Additionally, embodiments can automate search methods traditionally completed by trained sonographers, making these methods easily available at the point of care.

According to various embodiments, there is provided a head-interfacing medical device that can automatically search, locate and acquire a stable CBFV waveform exceeding a predefined quality threshold from any human being's temporal window, independent of his or her age, size, shape, or demography. According to other embodiments, other acoustic windows may also be used. Embodiments may employ the use of force and torque sensors to maintain appropriate contact force that maximizes signal quality. Embodiments may also employ the use of a machine-learning algorithm to emulate the expertise of a trained technician in locating the insonated vessel.

In order to locate and insonate a vessel of interest, the position and orientation of a transducer may be described by five coordinates, or degrees of freedom (DOFs): three translation coordinates (x,y,z), and two rotational coordinates (pan and tilt). For automatic transducer placement, all five coordinates may be independently controlled. While this specification frequently mentions a transducer, in general, the techniques and devices herein specifically described as using a transducer could also be employed in various embodiments using a probe or sensor probe. Several approaches have been attempted or are being developed to simplify TCD signal acquisition. Briefly, these can be divided into fully automated or semi-automated TCD signal acquisition.

Semi-automated TCD signal acquisition: Several methods have been developed to assist or aid a TCD technician in locating and maintaining a stable signal. One of these is the Power Motion-Mode Doppler (PMD). A color-coded display of all flow signals detectable at a given position and direction of the transducer in real time is provided by PMD. The major advantages of PMD are that transcranial windows can be easily found and maintained by a ultrasonographer and it facilitates vessel identification using depth and direction of flow. Although this technique is now a routine feature of most modern TCD systems, this technique still requires an expert sonographer for operation.

Another notable product for semi-automation of signal acquisition is a headband using robotics to implement a limited number of active degrees of freedom. The headband features two degrees of freedom that are robotically controlled (pan and tilt) and three degrees of freedom—x and y translations and z positioning manually, using mechanical fixtures. The two angular automatic DOFs scan angles of ±15 degrees to locate the optimal angles of insonation, resulting in a semi-automated window discovery and vessel identification process. Such transducer positioning systems with two automatic DOFs and with control of the TCD insonation depth as a third DOF, can place a sample volume within the brain at a Cartesian location (x,y,z). With only three total degrees of freedom, the orientation of the sample cannot be specified. Therefore, the angle of incidence to the blood flow cannot be set so there is no guarantee of the signal strength. The angle can only be adjusted by the user manually moving the transducer.

Fully-automated TCD signal acquisition: Probes have been developed that consist of a two-dimensional array of transducers (two dimensional phased array transducer). An advantage of this technology is that an ultrasound insonation beam can be electronically steered in translational and angular degrees of freedom to discover the insonation window and the vessel of interest. However, the method is only usable for the long-term continuous monitoring of CBF, as it has a setup time of greater than 30 minutes.

In various embodiments, there is provided a five degree of freedom (DOF) kinematic mechanism that fully automates TCD sensor position and orientation, evaluation of the temporal window quality, and can rediscover the temporal window even after complete loss of signal. While this specification frequently discusses Transcranial Doppler (TCD) probes, in general, the techniques and devices discussed herein specifically described as using TCD can also be employed in various embodiments using probes for methods such as ultrasound, transcranial color-coded sonography (TCCS), phased arrays well as well as other known ultrasound energy modalities. Additionally, other techniques that use probes that emit or receive energy in the electromagnetic spectrum such as functional Near-Infrared Spectroscopy (fNIRS) or EEG can also be employed. To automate window discovery and vessel identification, a computer controls the mechanism to translate and reorient the transducer along the surface of the head until a candidate signal is located. The computer is in communication with the transducer and receives and processes data from the transducer. Once located, the transducer is then reoriented to increase signal strength. Accordingly, embodiments can perform functions an expert sonographer cannot, and allows the use of TCD outside of specialized clinical settings. In some embodiments, an automated system makes TCD a viable option for smaller neurological clinics as well as primary care physicians. Some embodiments provide clinicians the ability to diagnose neurological conditions that may otherwise go untreated until a patient is symptomatic, as well as monitor pathologies such as sickle-cell anemia, that would otherwise require visits to an imaging center—ultimately reducing health system costs and bringing better standards of care to patients.

Accordingly, some embodiments provide a robotic system for automatically performing TCD scans. In some embodiments, the robotic system or mechanism may consist of a five degree-of freedom or six degree-of-freedom TCD transducer positioning system with motion planning driven by prior domain expertise given knowledge of the human anatomy. In some embodiments, the positioning system can translate in x and y axes to locate the window in translational axes, and in the z axis with both force and position feedback control to both position and maintain the appropriate force against the human skull to maximize signal quality by maintaining appropriate contact force. Two angular degrees of freedom (pan and tilt) are be used to maximize normal insonation of the blood vessel to maximize velocity signal. In some embodiments, the motion planning and vessel location may be driven by a machine-learning algorithm in order to locate the optimal TCD signal, or a TCD signal with an energy level exceeding a specified or predefined threshold. In some embodiments, the algorithm drives the search trajectory while simultaneously analyzing the blood flow velocity and motion-mode (M-mode) information from the TCD sensor to identify a candidate for the TCD window.

Figure 2:
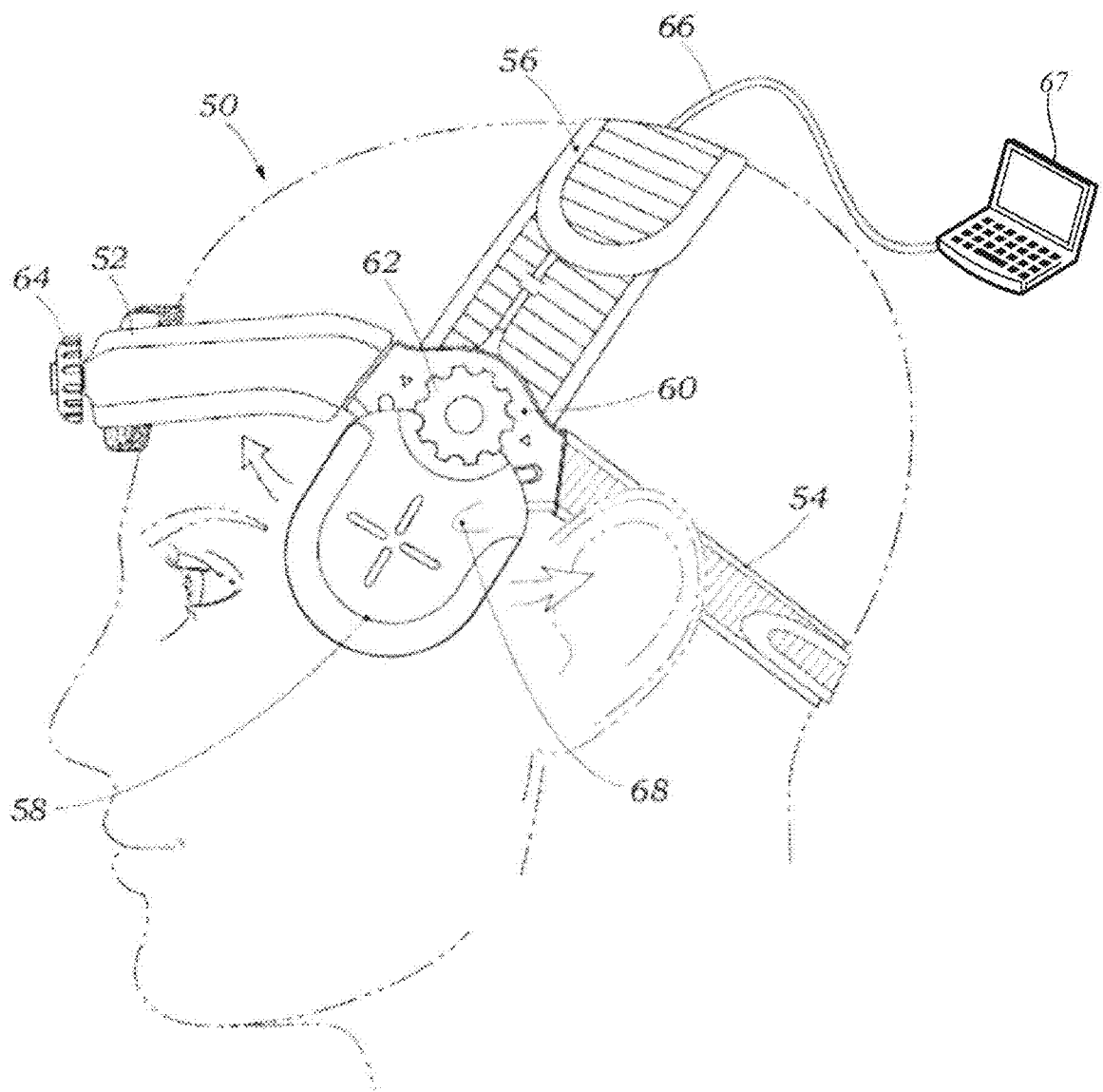
FIG. 2 is a side view of an exemplary TCD headset worn by a patient.

In some embodiments, the system includes a small robot holding a TCD transducer attached to an ergonomic headband. The robot's five degrees of kinematic freedom allow for the positioning and orientation of the TCD transducer. In some embodiments, each degree of freedom is driven by a motor with an optical encoder, hall effect, or other sensor to provide position feedback. Three degrees of freedom enable the transducer to be placed against the head and to slide along the skin in both up and down and side to side directions. The remaining two degrees of freedom implemented with gimbal are used to adjust the orientation of the transducer, which changes the direction of the ultrasound beam penetrating into the skull. FIG. 2 shows a side view of an exemplary TCD headset 50 worn by a patient.

Embodiments also provide a fully-automated robotic device for TCD window discovery and signal acquisition. An automated TCD transducer may accomplish two technical objectives: 1. Control the position, orientation and motion of the transducer exploring the surface of the head while applying an appropriate level of force; 2. Automate TCD window discovery and signal lock by implementing a search and signal processing algorithm that controls the transducer while interpreting the TCD sensor information to confirm discovery of the TCD signal and optimizing the signal strength. In some embodiments, position information is recorded and stored in a database. Furthermore, embodiments may correlate the signal to specific vascular anatomy (e.g., middle cerebral artery (MCA) vs posterior cerebral artery (PCA)), and may perform vascular mapping and vessel walking.

TCD sonography requires placement of the ultrasound transducer to the subject's head and moving the transducer while maintaining contact during both signal discovery and until the end of the data collection. Therefore, some embodiments control the transducer position and motion to enable the overall innovation of automatic TCD discovery and signal lock. In some embodiments, a robot automatically positions the device against the head and slides the transducer along the surface while applying sufficient force to maintain contact, without hurting subject. A technical challenge is to maintain the transducer nominally normal to the head during the surface exploration, with only approximate knowledge of the surface orientation, while controlling for applied force.

In some embodiments, the second technical objective integrates the TCD sensor information with robotic transducer motion to locate the TCD window, identify a signal, and reposition the transducer in order to maximize the signal strength during data collection. In some embodiments, a search algorithm controls both robotic transducer motion and the TCD transducer settings and data output. In some embodiments, the algorithm plans a transducer search trajectory while simultaneously analyzing the blood flow velocity and M-mode information from the TCD sensor to identify a candidate for the TCD window. Once the signal is acquired, the algorithm will direct the robot to reposition and reorient the transducer to minimize the Doppler angle, thereby increasing the signal magnitude. Various embodiments implement several types of search algorithms (e.g., a grid search of the temple area of a human subject). Some embodiments implement other algorithms with the goal of reducing signal acquisition time. Some embodiments of these other algorithms non-linear search motions, prediction based machine learning algorithms, or a combination of algorithms.

In some embodiments, there is provided a headset capable of diagnosing, monitoring, and treating a number of neurological conditions. In some embodiments, the headset utilizes ultrasound for the insonation of the major conducting arteries or veins of the brain; however, the technology is not limited to insonation of the cerebral vasculature as it could be used to insonate specific regions of the brain while utilizing the vasculature as a landmark (once it is known where the blood vessels are, the location of everything else in the brain is known). In some embodiments, the headset may include various sub-components or features, including:

Automatic Transducer Placement—In some embodiments, the system is placed on the head of the individual. In some embodiments, the system that interfaces with a head is implemented in a headset, but as will be discussed below, other embodiments exist as well. Once this placement has been accomplished, the ultrasound probes (or other transducer technology) come into contact with the skin.

Surface Alignment—In some embodiments, the transducer is correctly aligned with the surface of the skin to be useful.

Transducer Force Control—In some embodiments, in addition to surface alignment, a control of force of the transducer on the skin of a subject or patient is provided such that there is enough force to maintain contact, yet not too much to cause damage or discomfort to a subject or the probes. In some embodiments for the automatic transducer placement mechanism, a transducer force control mechanism is built in.

Window Discovery—In some embodiments, once the transducer is on the skin, the automated system identifies or finds the section of bone that is thin enough for the ultrasound energy to pass through in able to monitor the blood flow. The section is known as the acoustic window.

Signal Optimization—In some embodiments, when the system has identified the correct location on the skull and has positioned the ultrasound transducer to assess/measure cerebral blood flow, the system then optimizes the blood flow signal using a number of different inputs, such as, for example, orientation, signal quality, sound, depth, or intensity. This optimization may be accomplished for one depth or multiple depths.

Vascular Mapping—The cerebral vault has a number of major conducting arteries (i.e. Circle of Willis arteries) that can be insonated using embodiments. In some embodiments, once the signal is optimized, embodiments can optimize the signal automatically for all vessels and build a vascular map of the subject's brain.

Clinical Indications—Some embodiments described herein can be used for a number of different neurological conditions including TBI, stroke, dementia, vasospasm, and others impacting cerebral blood flow. These uses include diagnosis, monitoring, and treatment.

Diagnosis—Some embodiments measure small changes in cerebral blood flow and cerebral blood flow regulation. Results can be obtained to diagnose severe TBI (intracranial pressure), mild TBI (concussion), and specific strokes including large vessel occlusion and SAH.

Monitoring—Some embodiments can be used to determine how a neurological condition changes over time, e.g., over 12 hours for TBI or concussion or yearly checkups to diagnose/monitor dementia over a lifetime.

Treatment—Some embodiments can provide the use of ultrasound to break up clots or stimulate specific regions of the brain.

In some embodiments, the TCD signal is acquired using an ultrasound transducer that is placed against temporal window of a human subject's head. Each measurement may include positioning of the transducer in three translational and two rotational or orientation degrees of freedom. The measurement may include first scanning the temporal window of each subject to find the optimal TCD signal and then maintaining the signal lock, e.g., for up to 20 minutes, to collect sufficient data to make a diagnosis. As there are two temporal regions on a human head, each potentially consisting of a plurality of access windows, some embodiments perform bilateral scans.

In some embodiments, a robotic scanning system is provided which includes an electromechanical apparatus to automate scans bilaterally. The robotic scanning system enables operation and use of TCD ultrasonography by a lay user. It also allows optimization of the scan protocol, and makes signal acquisition reliable and repeatable.

In some embodiments, the robotic scanning system subsystem has at least three embodiments: commercial, consumer, and military. The commercial version is well-suited for use by healthcare professionals and in professional/collegiate athletics. The consumer version is well-suited for use in high school and youth athletics but may be used in healthcare and pro/collegiate athletics if it meets the all requirements. The military version is well-suited for military field hospital use.

External Control Software/Firmware Application as a User: Some embodiments control the movement and orientation of a TCD transducer with five degrees of freedom (x, y, z, pan, and tilt) so that the system is able to reliably detect MCA, PCA and anterior cerebral artery (ACA) arteries. In controlling the Cartesian degrees of freedom, an embodiment computes the inverse kinematics of the mechanism in order to command the joint positions. Some embodiments command the firmware to move the mechanism smoothly between several Cartesian configurations using a limited set of time-space interpolation points.

In some embodiments, robotic motors work together to increase the robot speed. In some embodiments, rather than simply moving along the x and y axes in a serial fashion, the robot moves the transducer along the x and y axes simultaneously to minimize the time to get to a new position. For example, if a robot can move along the x axis with a velocity v, and can move along the y axis at a velocity v, it could move to a diagonal point at a rate of $v*\sqrt{2}$, which is more than 40% faster than moving serially in only the x or y directions. In some embodiments, speed will further be increased if movement is made in the pan and tilt directions simultaneously.

In some embodiments, an application program interface (API) exists from a software application to command positions that does not necessarily update at the servo rate. Some embodiments query the status of the firmware. In some embodiments, the software/firmware API includes a firmware status update. In some embodiments, a firmware application scans enough temporal surface area so that the system is able to reliably detect MCA, PCA and or ACA for a subject. In some embodiments, the parameters of the scan are: Area size: no less than 55 mm across (x axis) by 30 mm down (y axis); Motion into the head (z axis) is sufficient to clear the head to ease removal of the device. In some embodiments, a software application controls scanning of the temporal surface of a patient or subject in less than two minutes. In some embodiments, translation speed of the sensor is not less than 7.5 mm/s.

In some embodiments, a firmware application controls the Cartesian movement of the TCD in the x,y,z axes with a precision and resolution of 1 mm to obtain TCD data, and it allows positioning of a 2 mm sample size TCD beam within a 4 mm vessel diameter. In some embodiments, precision and resolution increase to perform vascular mapping. In some embodiments, a firmware application orients the TCD transducer over a large enough range that the system is able to reliably detect MCA, PCA and ACA over a variety of head shapes. In some embodiments, pan and tilt are capable of rotating a minimum of ±30 degrees, and increases to account for anatomical differences of temple interface to transducer.

In some embodiments, a firmware application orients the TCD transducer with a precision and resolution of 0.1 degrees to obtain TCD data. This precision greatly exceeds the performance of an experienced human user and could only be achieved with the precision of a robotic system. In some embodiments, a firmware application puts adequate and constant pressure with TCD sensor on patient's head to be able to acquire a high fidelity TCD signal.

In some embodiments, a software application prevents mechanical motion from interfering/coupling with the ultrasound signal, to allow collection of cleaner data for an algorithm to analyze TCD signals with higher reliability. In some embodiments, a software application provides bilateral scanning, to make algorithms more efficient, with correct kinematics. In some embodiments, two mechanisms are used. In some embodiments, a single mechanism is used and it swaps to either side of the head for access to either of the temporal windows.

In some embodiments, a minimal amount of gel is necessary to enable TCD sensing, so as to prevent gumming up the mechanics. In some embodiments, the gel is capable of being cleaned from the machine easily. In some embodiments, the system actively maintains the TCD signal for 20 minutes or more after acquisition in order to complete a breathing protocol. Maintaining the signal may involve actively repositioning the TCD system to strengthen the signal due to patient motion. Some embodiments can maintain the signal for 6 hours or more.

A. Headset Design

Figure 1B:
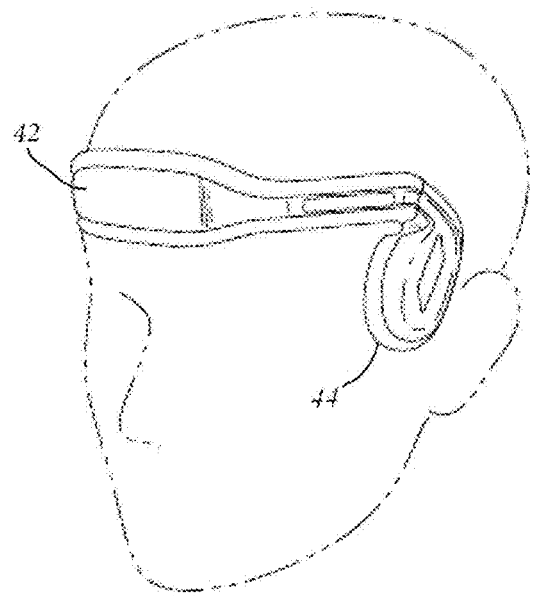
FIG. 1B is a view showing the ergonomic headband on a head.
Figure 1C:
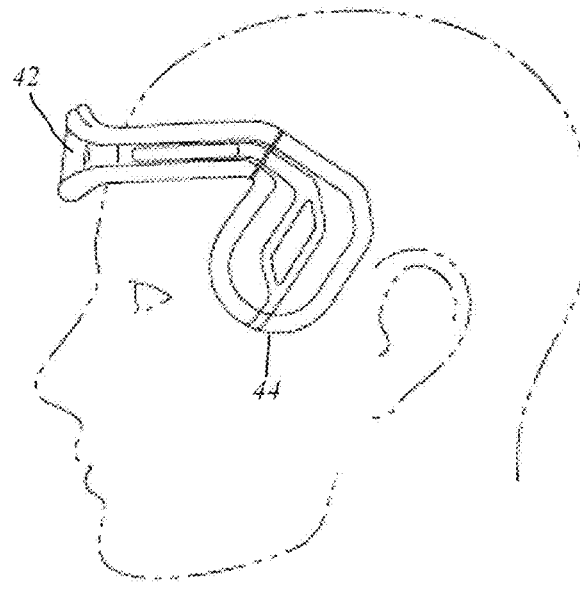
FIG. 1C is an elevation view showing the ergonomic headband on a head.
Figure 3A:
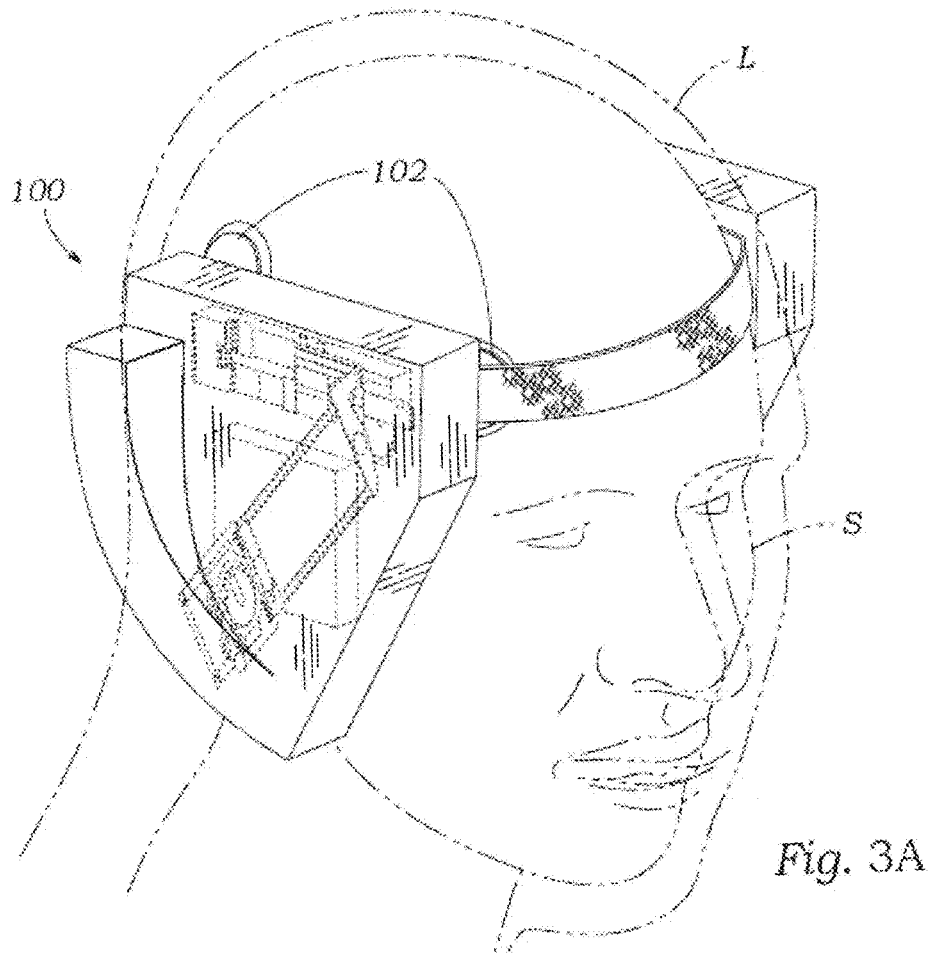
FIG. 3A is a perspective view of a TCD headset worn by a patient.
Figure 3B:
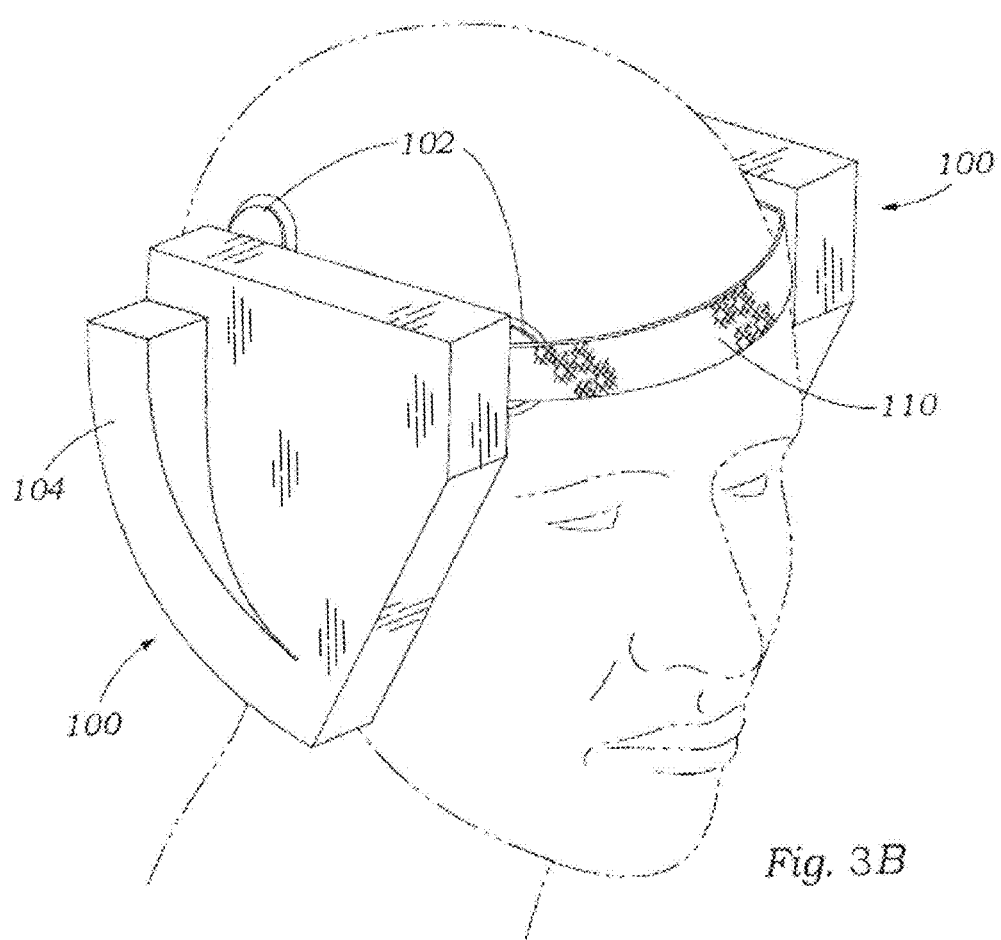
FIG. 3B is a perspective view of a TCD headset worn by a patient.
Figure 4A:
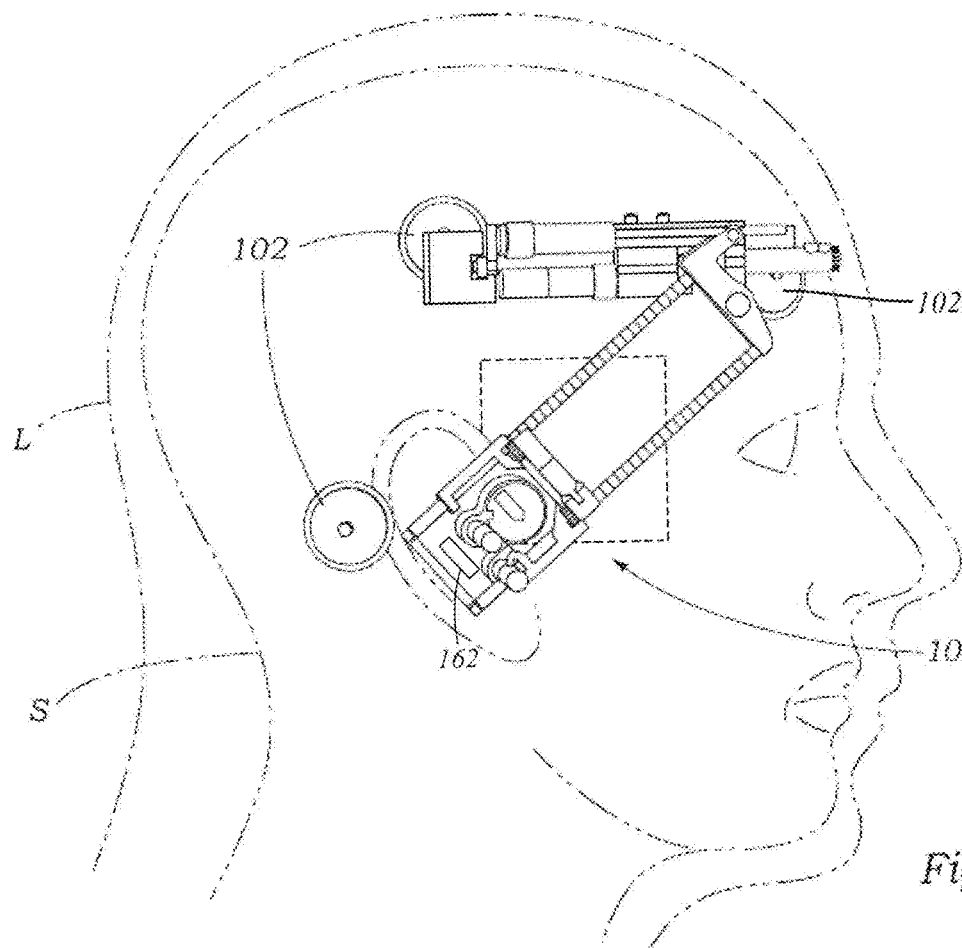
FIG. 4A is an elevation view of a TCD headset with the housing removed worn by a patient.
Figure 4B:
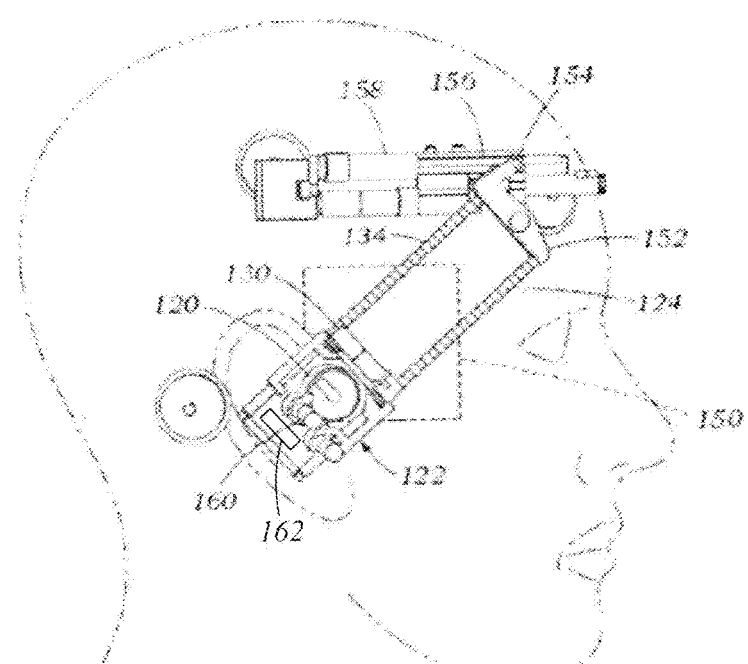
FIG. 4B is an elevation view of a TCD headset with the housing removed worn by a patient.
Figure 5:
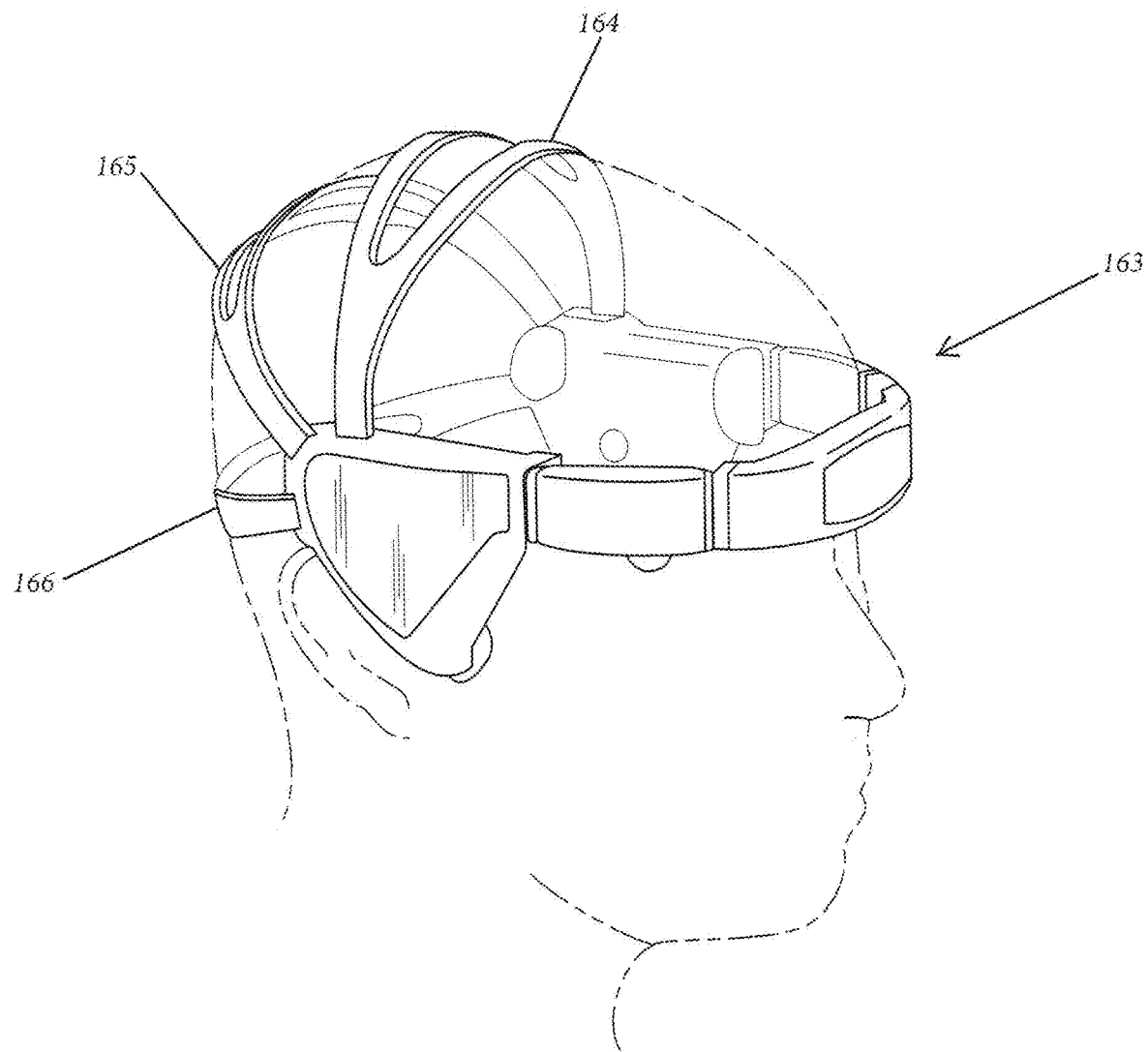
FIG. 5 is perspective view of a TCD headset worn by a patient containing multiple straps.
Figure 6:
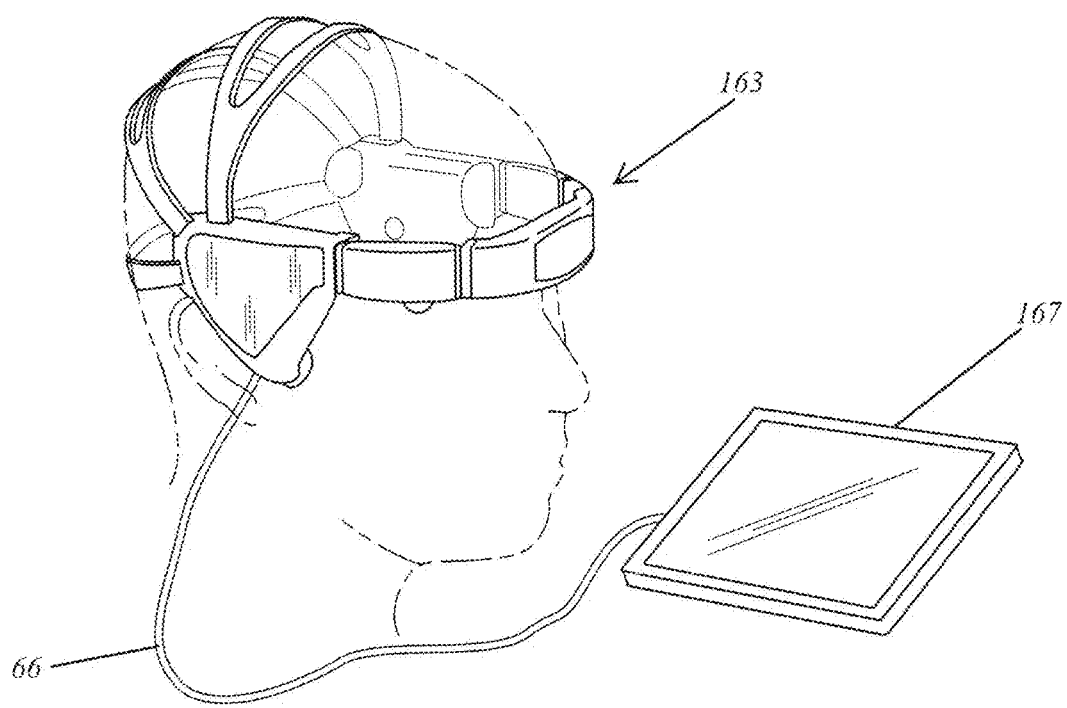
FIG. 6 is perspective view of a wired TCD headset worn by a patient.
Figure 7:
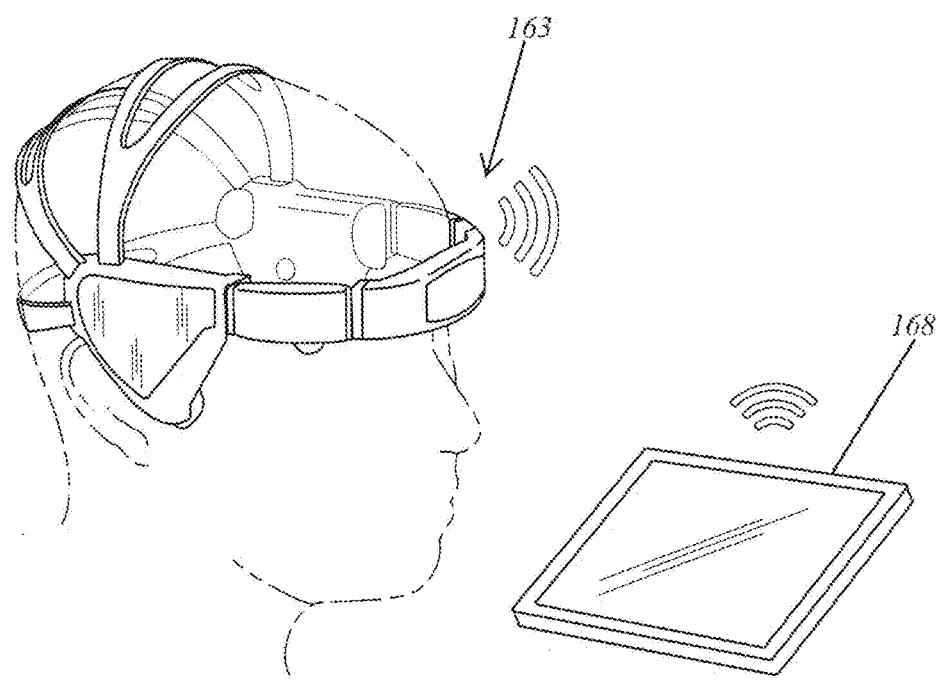
FIG. 7 is perspective view of a wireless TCD device worn by a patient.

FIGS. 1A-1C depict a Transcranial Doppler (TCD) device according to various embodiments. FIG. 2 depicts a TCD headset 50 according to various embodiments. FIGS. 3A-3B depict a TCD headset 100 according to various embodiments. FIGS. 4A-4B depict a TCD device 100 according to various embodiments. FIGS. 5-7 depict variations of TCD headsets 163 according to various embodiments.

FIGS. 1A-1C show an automated TCD headset 40 having a display screen 42 on the front thereof. More particularly, the headset 40 includes dual ultrasound probes 44 on the sides and a headband 46 that extends around the front so as to connect the two probes. As seen in FIGS. 1A-1C the headset 40 fits over the cranium of a patient with the probes 44 located at either temple. The probes 44 include TCD scanners therein that can auto locate the MCA, ACA, PCA or other arteries. Desirably, the headband 46 may be elastic or adjustable in nature and enables the headset 40 to fit snugly over the front of the head of a variety of different head sizes so that the inner face of the probes 44 makes good contact with the temples. A lubricating gel is preferably used to improve acoustic transmission.

Although not shown for the sake of clarity, power supplies, either in the form of batteries, or power supplies that operate based on readily available convenience outlets or other available electrical current are used to electrically power all components that normally require electrical power, such as transducers, motors, computers and processors, robot arms, electrical circuit boards, displays, and the like.

FIG. 2 is a side view of another exemplary TCD headset 50 worn by a patient and having a forehead strap 52, a rear strap 54, and a cranial strap 56. The straps 52, 54, 56 help secure the headset 50 on the head, and in particular ensure good contact of a pair of reciprocating ultrasound scanners 58 with either temple. The TCD scanners 58 mount for reciprocal forward and backward rotation, as indicated by the movement arrows, to a junction member 60 at the intersection of the three straps 52, 54, 56. In one embodiment, the TCD scanners 58, which incorporate transducers or probes, rotate about 60° in each direction about a z axis perpendicular to the x,y scan plane. Although not shown for the sake of clarity, a small motor within the junction member 60 enables movement of the scanners 58.

The system of the three straps 52, 54, 56 is effective in holding the headset 50 in place. The cranial strap 56 includes a Velcro break for adjustability, the rear strap 54 is desirably elastic, and a pair of tightening knobs 62 on each junction member 60 and a tightening knob 64 at the middle of the forehead strap 52 enable fine adjustment of the position of the scanners 58 for X-Y calibration. The cranial strap 56 helps limit migration of the headset 50 once secured due to movement of the jaw and associated muscles.

In some embodiments, a cable 66 may be attached to the junction members 60 for connection to a control unit such as computer 67, a tablet computer (not shown for clarity), or any other type of computing device, or the system may communicate wirelessly with a computing device. The computer 67, or other connected computing or processing device is in communication with and provides processing to receive and process data returned from TCD Scanners 58.

Each TCD scanner 58 desirably includes an injection port 68, preferably formed by an indent leading to a channel, for introduction of a lubricating gel to the inside contact surfaces. This injection port 68 helps reduce a messy application of the gel. In a preferred embodiment, the TCD sensor on the inside of each scanner 58 may be displaced in the z direction, or toward and away from the temple, to optimize acoustic contact. In some embodiments, headsets are capable of being cleaned of all ultrasonic coupling gel following use. Preferably, wipes or other such devices are used to protect the mechanism from accumulation of foreign matter within the mechanism. Materials selected withstand cleaning with water, isopropyl alcohol, and other cleaning agents routinely used in the doctor's office and clinical setting.

FIG. 3A is a perspective view of an exemplary TCD headset 100 positioned on soft mounting feet 102 on the side of a patient's head. Two sizes of patients' heads, small S and large L, are shown in contour lines to indicate the range of adjustability of the headset 100 for different sizes of patients. An outer housing 104 is shown in phantom to visualize internal components of the headset 100.

FIG. 3B shows the outer housing 104 against a profile of the wearer's head for clarity, and also shows a second headset 100 on the opposite side of the patient's head connected to the first set by straps 110. In some embodiments, each headset 100 has a plurality of the mounting feet 102 which resemble small suction rings to cushion the sets against the head and also provide some spacing between the head and the outer housing 104. In some embodiments, there are three mounting feet 102 on each side, as shown in FIG. 4A. The headsets 100 are anchored by tensioning the straps 110. There may be one forehead strap 110 as shown, or also one around the rear and even one over the cranium, as was described above in connection with FIG. 2.

With reference to FIGS. 4A and 4B, side elevational views of an embodiment of the TCD headset 100 of FIGS. 4A and 4B are shown with the outer housing 104 removed. Within the housing, a TCD scanner 120 mounts on a carriage 122 that slides on a pair of diagonal rails 124. The carriage 122 includes a small motor 130 that turns drive gears that mesh with small teeth 134 along both rails 124. The motor 130 may be controlled remotely or by wires, and the carriage 122 thus may be moved diagonally along the rails 124.

In some embodiments, the TCD scanner 120 mounted on the carriage 122 thus may be moved over the temple area of the subject. In some embodiments, the headset 100 can desirably scan an area of about 2 square inches as indicated by the dashed square area 150. To cover the entire area 150, the upper ends of the rails 124 pivotally attach to a frame member 152 that translates laterally along a generally horizontal path. More specifically, a pivot point 154 on the frame member 152 connects to a translating rod 156 that may be moved by a cylinder 158 in a piston/cylinder relationship. Alternatively, the cylinder 158 may contain a small motor which engages the end of the rod 156 opposite the pivot point 154 and translates it laterally. There are several ways to accomplish this movement, and each is controlled along with movement of the carriage 122 for coordinated two-dimensional movement of the scanner 140 in the x,y plane over the target area 150.

In addition, in some embodiments, the robotic arm encompassing the scanner 140 mounted for movement on the carriage 122 has a z axis displacement device actuated by a stepper motor 160. The robotic arm is further equipped with a pressure sensor (not shown) that maintains sufficient pressure of the scanner 140 against the skin for consistent signal quality. This pressure sensor is a feedback mechanism used to adjust location due to subject movement. This constant pressure addresses variability issues associated with patient movement and TCD.

In some embodiments, translational motion along the x,y,z axes and the pan and tilt directions or orientations are accomplished through use of motors 160 driven by a local motion control unit 162. The motion control unit 162 may comprise a microcontroller with memory and a CPU programmed to monitor and control the motors 160, as described in more detail below. In some embodiments, servo feedback is provided to assure that the desired position has been achieved. The servo feedback signal takes the form of a reverse EMF or encoder signal provided to the motor control unit 162. In some embodiments, instead of placing a programmed microcontroller in the headset co-located with motor 160, as shown in FIG. 2 and FIG. 6, a cable 66 may connect the headset with a computer 67, or the headset may communicate wirelessly to a computer 67 that is programmed to move the motors 160 and monitor the information returned from a TCD transducer (not shown for clarity) located within the headset.

Command Set: In some embodiments, X,Y,Z axes and pan and tilt direction movement will be controlled via an appropriate processor or microprocessor. In some embodiments, a command for movement along any axis will be in the form of a signed integer number indicating the number of step increments to be moved along each axis.

FIG. 5 shows a headset 163 with multiple straps 164, 165, 166 to allow for a snug fit. A unit that can adjust to several head sizes is important for wide-spread adoption. If the head mount does not fit correctly the TCD probes cannot acquire the optimal signal. The disclosed design addresses this concern separating the "anchoring" of the headset and the robotic mechanism. This design allows the user to fit the headset on any sized head with no impact on the ultrasound mechanism to reach the signal.

FIG. 6 shows a headset 163, connected via a cable 66 to a computer display 167 that may be used to input information from the patient or subject and to display information obtained from the scan of the patient or subject. FIG. 7 shows a headset 163 communicating wirelessly with a display 167 that may be used to input information from the patient or subject and to display information obtained from the scan of the patient or subject. The headset 163 and display 167 may communicate wirelessly using wireless methods of communication known to those skilled in the art, such as Wi-Fi, Bluetooth, Li-Fi, cellular communication technologies, and other known methods of radio communication.

In certain embodiments, the systems and methods described could be used for the diagnosis of mild and moderate TBI where there is no increase in ICP. The underlying physiology is different; however, the core analysis is the same. The cerebral hemodynamic changes following a mild TBI are well documented by several studies. The physiologic origin of these changes range from regional blood flow variations owing to increased metabolic demand in certain regions of the brain to variations in CBF due to disruptions in the cerebral vasculature or the brain itself (such as decreased compliance due to high intracranial pressure (ICP)).

B. Automatic Transducer Placement

FIGS. 8-11 illustrate various TCD systems and devices capable of automatic transducer placement.

Figure 8:
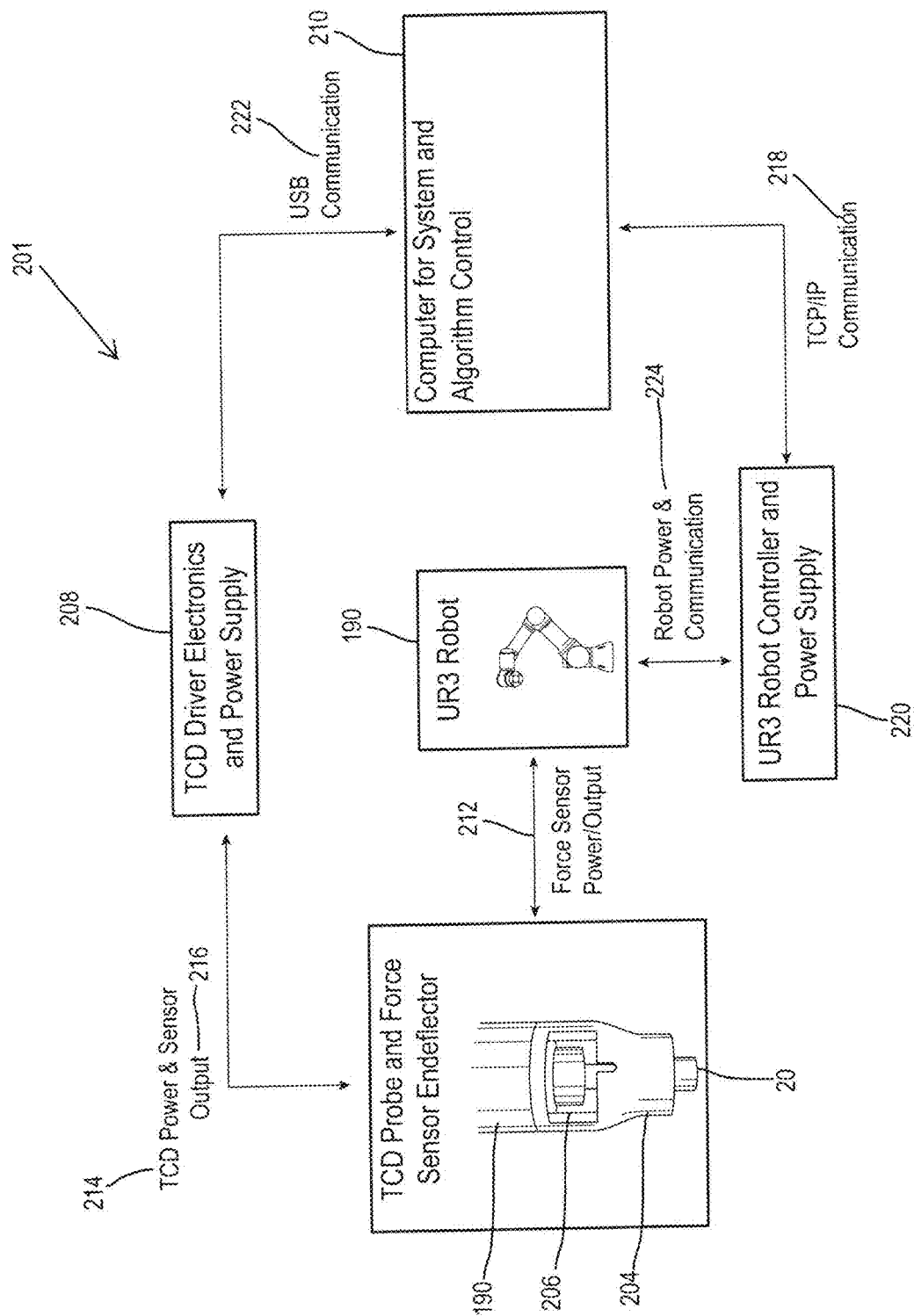
FIG. 8 is a system diagram of a TCD system.

Integrated System Framework for Automatic TCD Sonography—As shown in FIG. 8, in some embodiments, an automated TCD system 201 comprises a robot arm 190, also referred to as a redundant manipulator, that provides robotic positioning, transducer holder 204, transducer 20, with force sensor 206, TCD driver board 208, and algorithm control computer 210. A preferred device used to position and orient the transducer is a commercially available six degree of freedom Universal Robotics, UR3 tabletop robot arm 190. This robot arm 190 provides sufficient kinematic precision, has been certified for use around human beings in its workspace, and has settable safety levels to limit velocity and impact forces. It also has additional degrees of freedom. These characteristics address safety concerns to allow use with human subjects. A probe or transducer 20, that may be a Spencer TCD probe, is mounted onto a transducer holder 204, called an "endeffector." The endeffector mounts to the end of the robot arm 190 and has an axial force sensor 206 to monitor directly force applied by the robot arm 190 to the surface being scanned. The force sensor 206 sends force sensor information 212 to the robot arm 190. This force sensor 206 serves both to ensure that enough contact force is made between the transducer 20 and the surface being scanned, but is also a second measure of safety to prevent overloading of contact forces. In some embodiments, the probe driver board 208 connects to the transducer 20 and provides electronics to send power 214 to the probe to emit ultrasound energy and process the returned sensor output signal 216.

In some embodiments, the control computer 210 connects to and communicates with the robot arm 190 controller 220 via TCP/IP communication 218 and to the probe driver board 208 by USB 222. The robot arm 190 provides information 224 about such things as its current position, velocity, estimated forces applied to the endeffector, custom sensor readings, and other status information to controller 220, which is then communicated via TCP/IP 218 to the control computer 210. The probe driver board 208 USB 222 interface provides a method of setting up transducer 20 parameters and operation, such as depth, and processes data to produce information such as, but not limited to, the velocity envelope. The control computer 210 takes this information to execute the probe search algorithm and to issue new robot arm 190 commands. Embodiments may also employ the use of a machine-learning algorithm to emulate the expertise of a trained technician in locating the insonated vessel. In some embodiments, a control computer 210 autonomously controls the transducer 20 scanning process, but in other embodiments, a human being may teleoperate the transducer 20 scanning process using technology known to those of skill in the art, such as that used in the NeuroArm and DaVinci surgical robots.

Integration testing has shown that it is possible to maintain a 125 Hz control loop over the entire system, which is fast enough to read all data from the probe driver board 208, read all status data from the robot arm 190, update a signal processing and planning algorithm, and issue a new motion command to the robot arm 190 at its servo rate.

In some embodiments, a modular snake robot with more than six degrees of freedom is used instead of the UR3 to the redundant manipulator.

Figure 9:
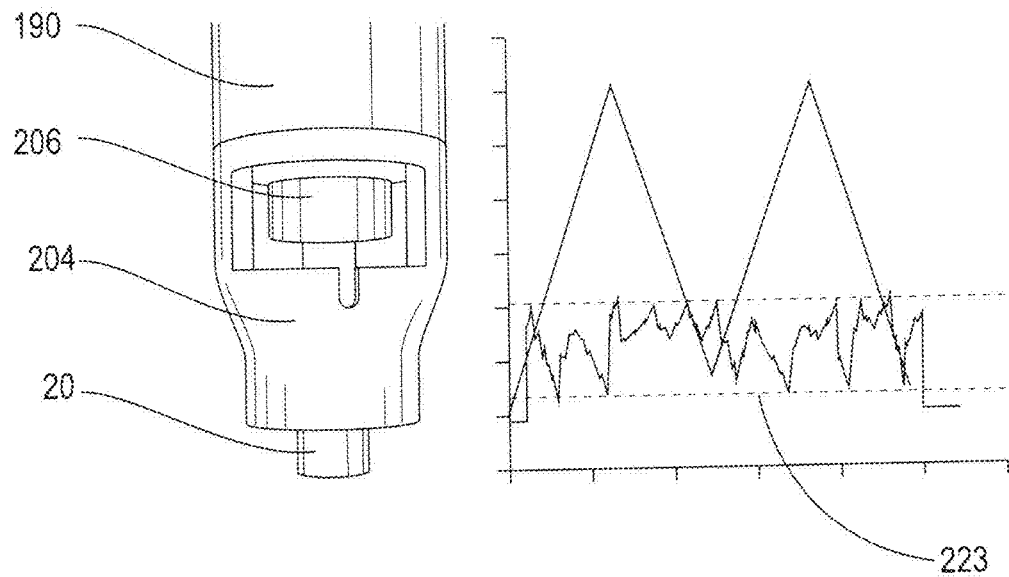
FIG. 9 is an elevation view of a transducer and illustrates admittance controller to control force.
Figure 10:
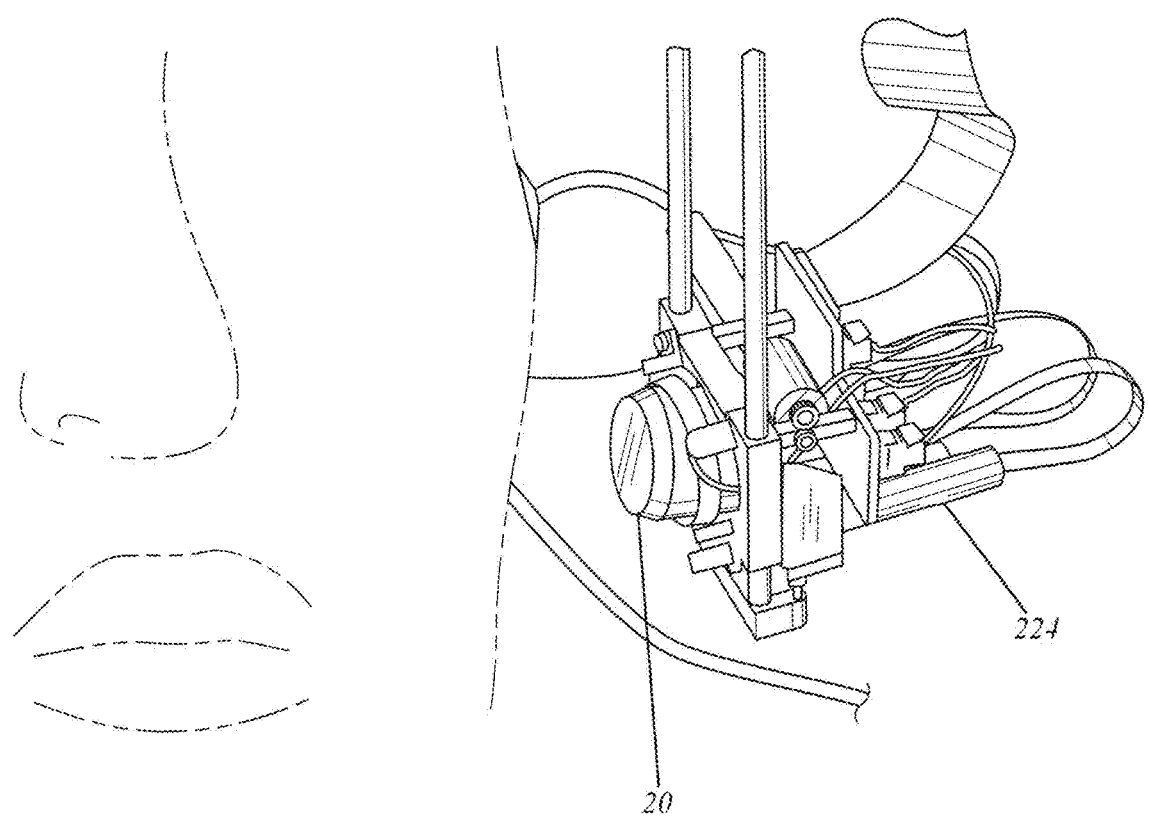
FIG. 10 is a perspective view of a TCD transducer holder.
Figure 11:
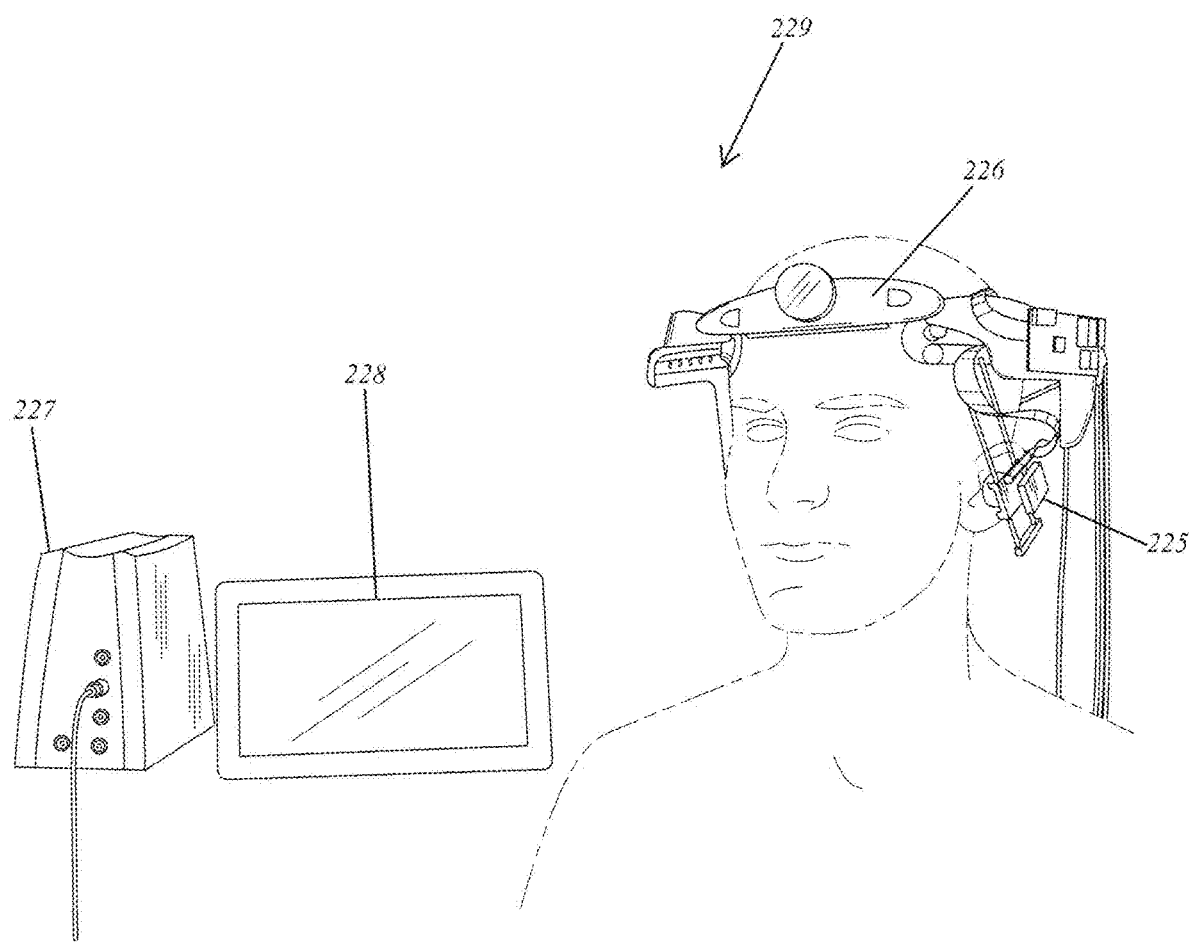
FIG. 11 illustrates a discovery platform including a small robot attached to an ergonomic head band.

FIG. 9 illustrates admittance controller results control force with precision. At left is shown transducer 20 mounted in probe holder 204, contacting force sensor 206, held by robot arm 190, to allow contacting and sliding over a flat surface. At right is shown the force output controlled to a deadband range 223 of 2 to 10 N. FIG. 10 illustrates a TCD Transducer Holder: The transducer 20 is mounted on carriage 224 that can translate in x,y,z directions, while a gimbal mechanism (not shown for clarity) allows for orientation changes in pan and tilt directions. FIG. 11 illustrates discovery platform 229 comprising: a small robot 225 attached to an ergonomic head band 226. TCD Transducer electronics 227 for processing TCD signals obtained from robot 225, and an output screen 228 for displaying scan data are shown on the left side of the figure.

In some embodiments, TCD sensor positioning and orientation are achieved with a robotic five degree of freedom (DOF) kinematic mechanism. For TCD applications, the position and orientation of a transducer can be described by five coordinates: three translation coordinates (x,y,z), and two rotational coordinates (pan and tilt). For automatic transducer placement, all five coordinates can be independently controlled.

Some existing devices rely on an expert human user to manually translate the transducer in x,y,z coordinates to the approximate location of the temporal window against the head, and further control of the orientation to complete signal acquisition. After translational placement, some semi-automatic devices are able to use two DOFs for orientation to further increase the signal strength. Control of orientation alone is insufficient for transducer placement and temporal window discovery.

In some embodiments, the kinematic mechanism includes five motor degrees of freedom, Q={J1,J2,J3,J4,J5} (called motor or joint space) to affect five degrees of freedom in position and orientation X={x,y,z,pan,tilt} (also called task space). The forward kinematics can be written as the relationship between motor coordinates and transducer coordinates:

$$X=\text{fwd\_kin}(Q)$$

where fwd_kin is a function representing a series of equations based on the mechanism design and typically analyzed by Denavit-Hartenberg parameters.

In some embodiments, placement of the TCD transducer can be specified via the inverse kinematics with either an analytic inverse solution $$Q=\text{inv\_kin}(X)$$

or by using a numerical differential such as the Jacobian inverse solution $$dQ_{cmd}(n)=J^{-1}(X_{err}(n))$$

where J is the Jacobian, relating differential motion of the motors to the differential motion of the transducer, $X_{err}(n)$ is the transducer position and orientation error at time n, and $dQ_{cmd}(n)$ is the differential motor command at time n.

Some embodiments include enough DOFs to completely define the problem, i.e., 5 DOFs to define x, y, z, pan, and tilt. Another embodiment utilizes a depth setting for a 6th virtual DOF, creating a redundant manipulator. This redundant manipulator enables the possibility for an infinite amount of solutions. This embodiment increases possibilities for how to place the sensor.

In some embodiments, after the device with the robot is placed on head (or head is placed into a device with robot), the robot moves the transducer towards the patient while keeping the orientation of the transducer normal to the surface of the head. Much of this process is established by using the kinematic knowledge of the device:

The Cartesian coordinates of the transducer is $$X=\{x,y,z,pan,tilt\}$$

Using the joint positions of each DOF, $Q=\{q_1, q_2, q_3, q_4, \ldots q_n\}$ of the device and knowledge of the forward kinematics of the device, X can be computed as a function of the joint positions $$X=fwd\_kin(Q)$$

Using inverse kinematics to generate joint commands $$dQ_{cmd}(n)=J^{-1}(X_{err}(n))$$

Establishing transducer contact and seating against the head is not simple because the exact orientation of the head relative to the transducer is not known. Even if it is roughly in line with the transducer, a small error will prevent the transducer from seating flush against the head. In some embodiments, the robot will attempt to maintain the commanded orientation of the transducer with the programmed servo stiffness of the controller.

In some embodiments, for transducer contact and seating, instead of trying to predict and control the exact position and orientation of the transducer, the transducer's impedance is selectively controlled. This control can be thought of as controlling an object's apparent stiffness, inertia, and friction, whether by mechanical design or software. In some embodiments, the orientation degrees of freedom of the transducer are compliant so that they rotate against contact and seat the transducer flush with the head, while the translation degrees of freedom are stiff enough to move the transducer and keep it placed against the head. In some embodiments, each of the directions have different impedances.

Software—limiting motor torque and motor servo stiffness: In some embodiments, the simplest software solution limits the torque applied by each of the motors, and can have different limits for creating different stiffnesses in different directions. This property makes the pan and tilt very compliant, while the translational are moderately more stiff. The limitation is that the stiffnesses do not adjust as the orientation of the transducer changes. For example, as the transducer changes orientation, the stiffness through the center of the transducer is a combination of each of the X, Y and Z axis actuators, not just the Z actuator. Nominally stiffness through the transducer should be more compliant than the X, Y translational degrees of freedom.

Software—task space impedance control: in some embodiments, the transducer orientation defines a local coordinate system with the Z axis through the center of the transducer. Instead of manipulating the impedance of the transducer by adjusting motor servo stiffness and torque limiting, the kinematics of the entire robot sets the impedance of each of the five directions, X, Y, Z, pan, and tilt, local to the transducer's coordinate frame. The transducer can be more compliant through the center line of the transducer and still keep in contact with the surface of the skin, but have local X and Y stiffness sufficient to control the transducer's location with precision.

Hardware—Series Elastic actuator: In some embodiments, the impedance of the device can be altered by adding a compliant member into the mechanical design, either as a spring element into the motor or as a structural member of the robot. Either method requires that the amount of deflection is measured in order to measure the exact position and orientation of the transducer. A series elastic actuator has the benefit of being designed to an exact compliance, and even have a damping element added, while avoiding computational nonlinearities and instabilities associated with programming the impedance.

Direct Sensing: In some embodiments, the interaction force and torque can be controlled between the transducer and the head by placing a force/torque sensing behind the transducer. Using that information the impedance of the transducer can be programmed in software using closed loop control.

Indirect Sensing:—In some embodiments, the force can be indirectly measured by monitoring the applied current of the motor. Once taking into account the kinematics of the robot, the force/torque vector of the system can be computed from the Jacobian: $F=J^T T$, where T is the vector of motor torques as predicted by the applied current to the motor.

In some embodiments, the automatic transducer placement system may include different sensors. Although TCD probes are described, different sensors may be utilized, such as, but not limited to, optical, radar, and the like.

In some embodiments, the automatic transducer placement system may include a gel pad. For example, the pad of gel may be placed with a border that the robot can identify, which could also serve as a method for transducer placement.

C. Window Discovery

Some embodiments that perform automatic window discovery do so using mechanisms with four, five, six, or more degrees of freedom, which insonate at multiple depths and angles. These additional degrees of freedom and insonating at multiple depths and angles speed the process of locating appropriate window locations on the skull and mapping blood vessels in the brain.

Figure 12:
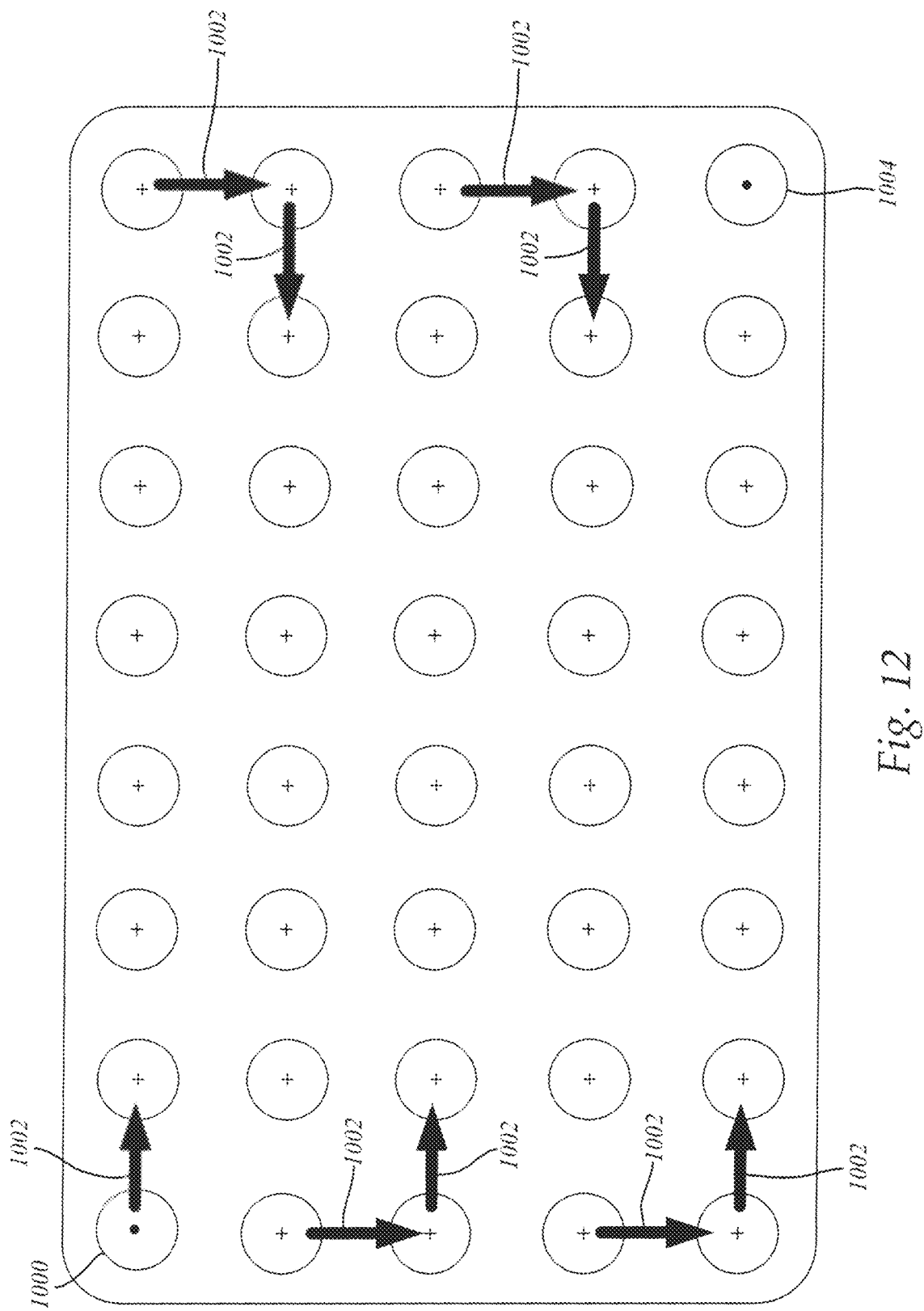
FIG. 12 illustrates a grid search pattern.
Figure 13:
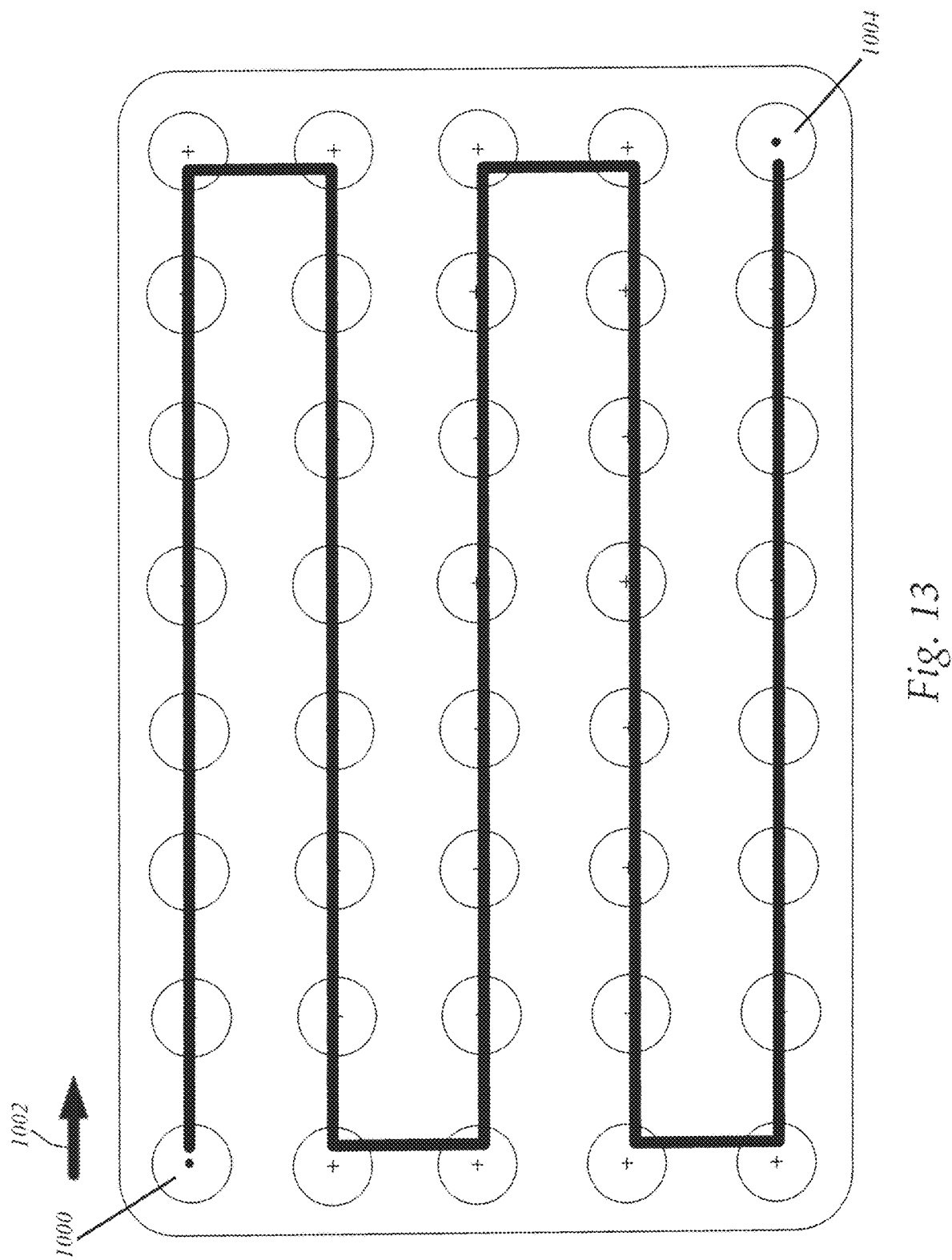
FIG. 13 illustrates a grid search pattern.
Figure 14:
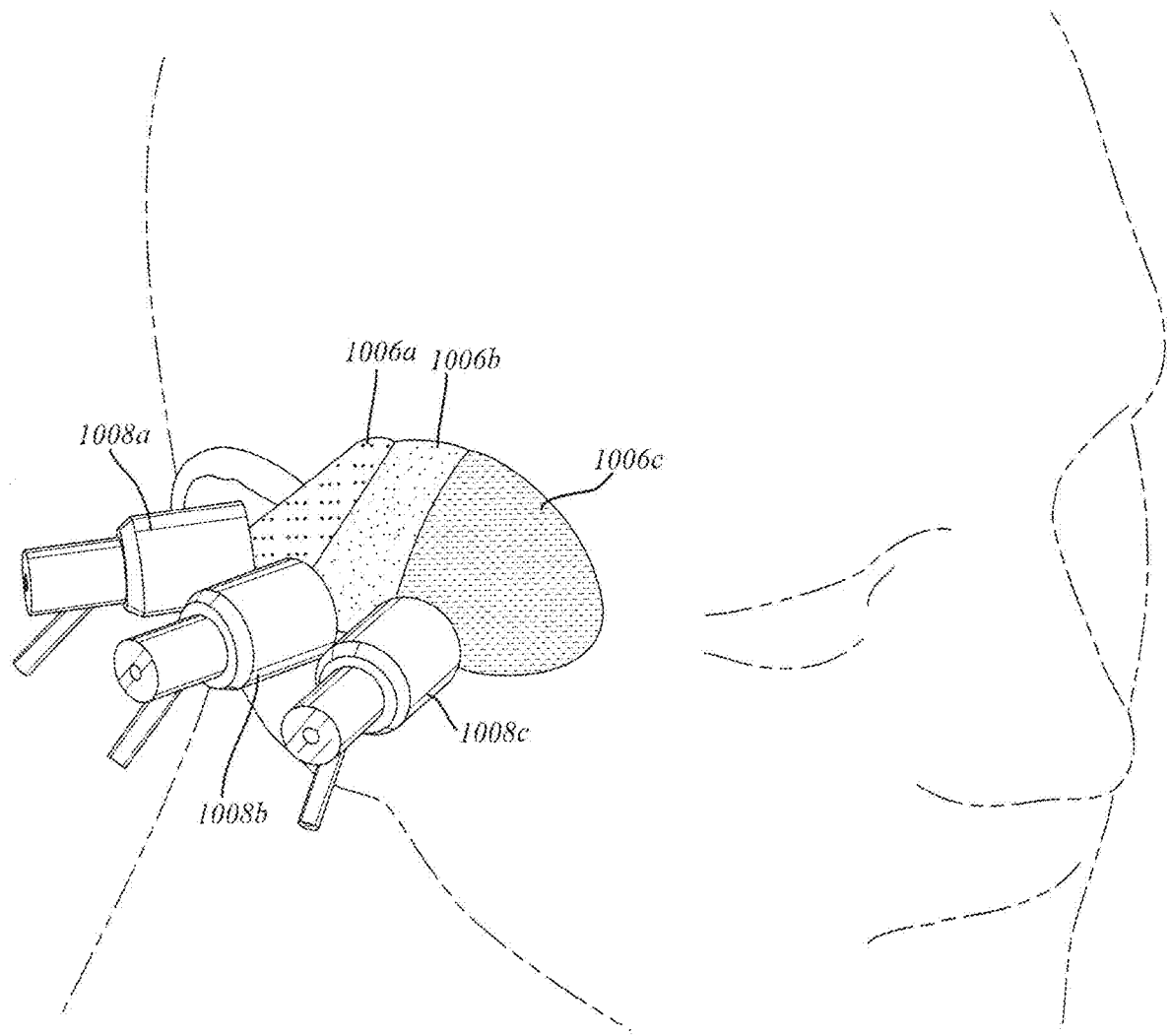
FIG. 14 illustrates overlapping volumes in a target area.
Figure 15:
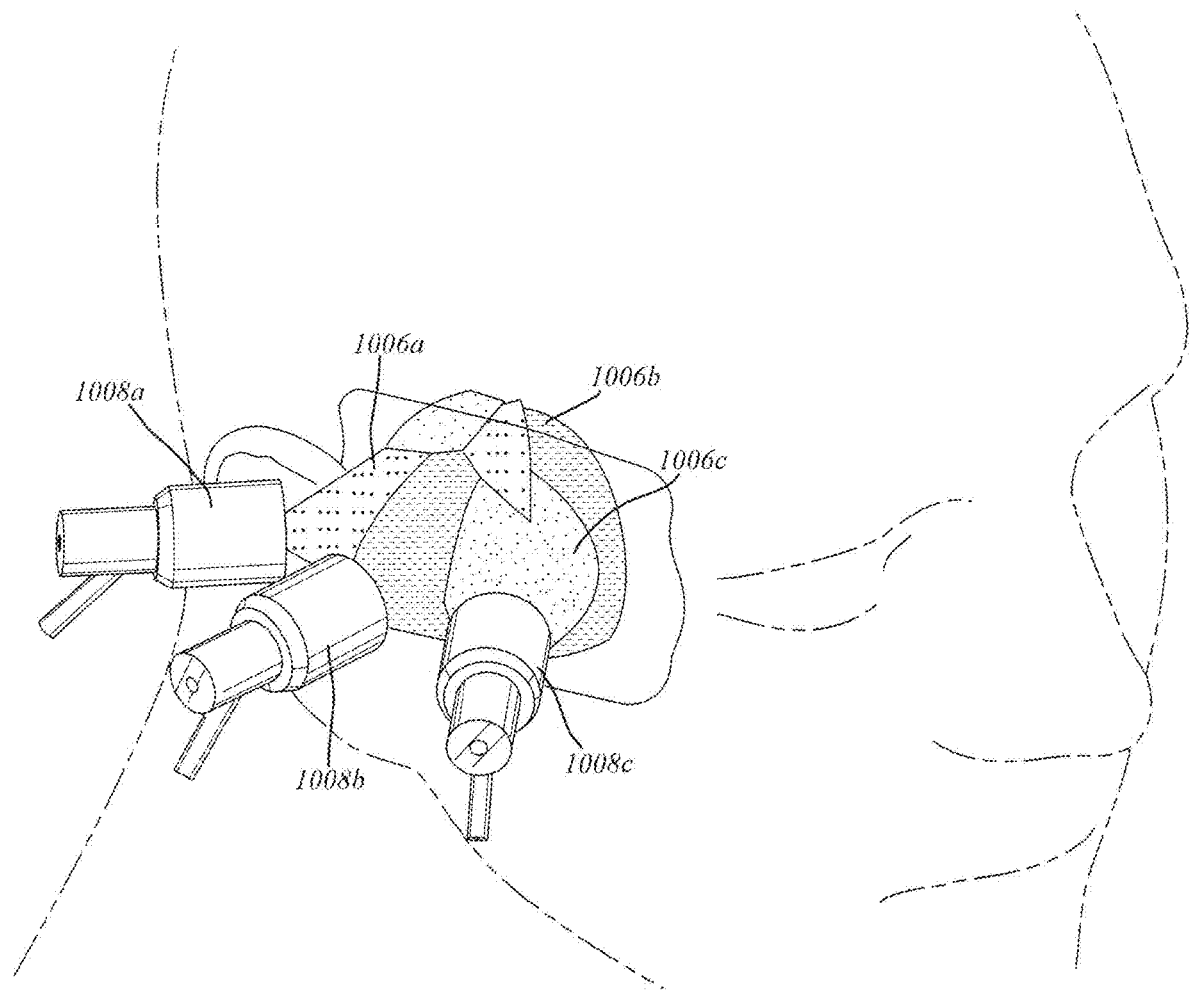
FIG. 15 illustrates overlapping volumes in a target area.
Figure 17:
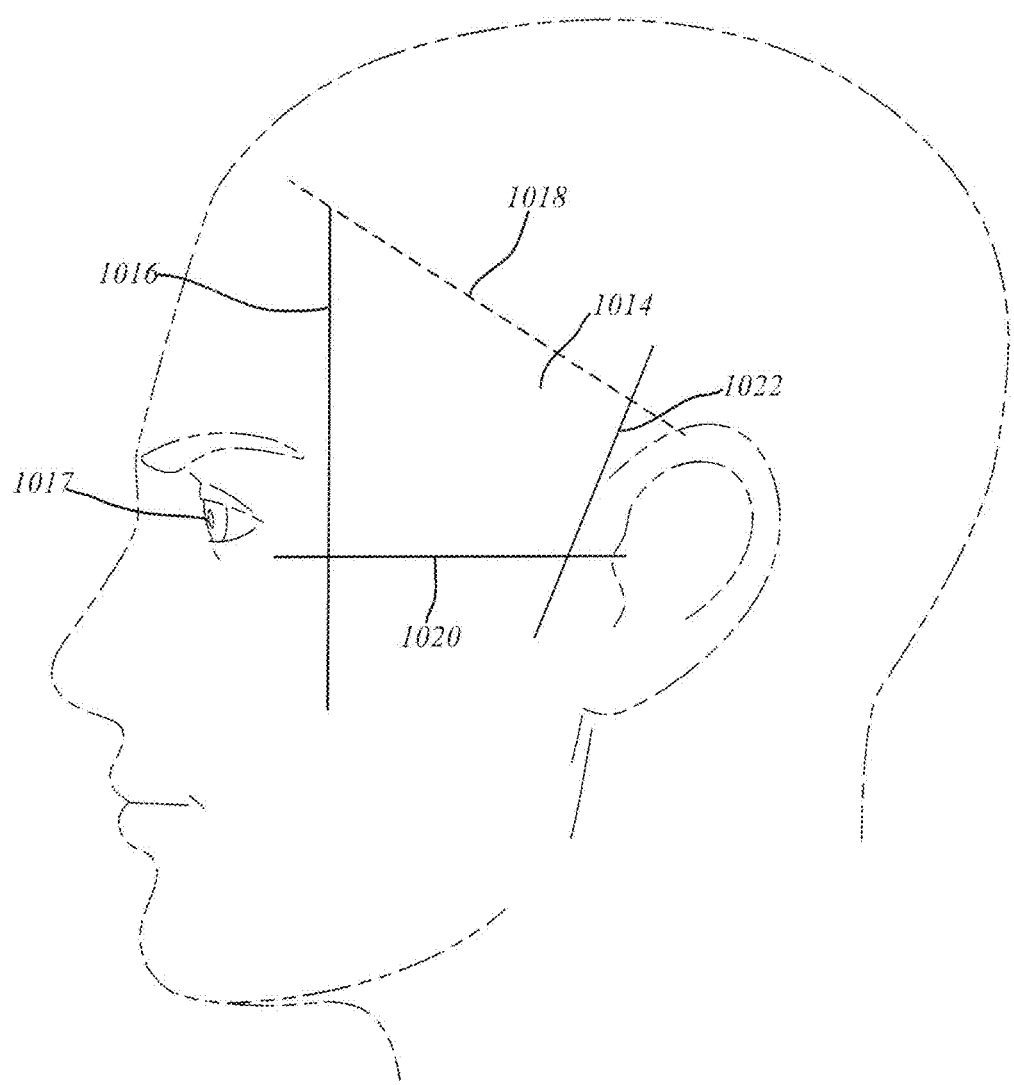
FIG. 17 illustrates temporal window landmarks and limits.
Figure 18A:
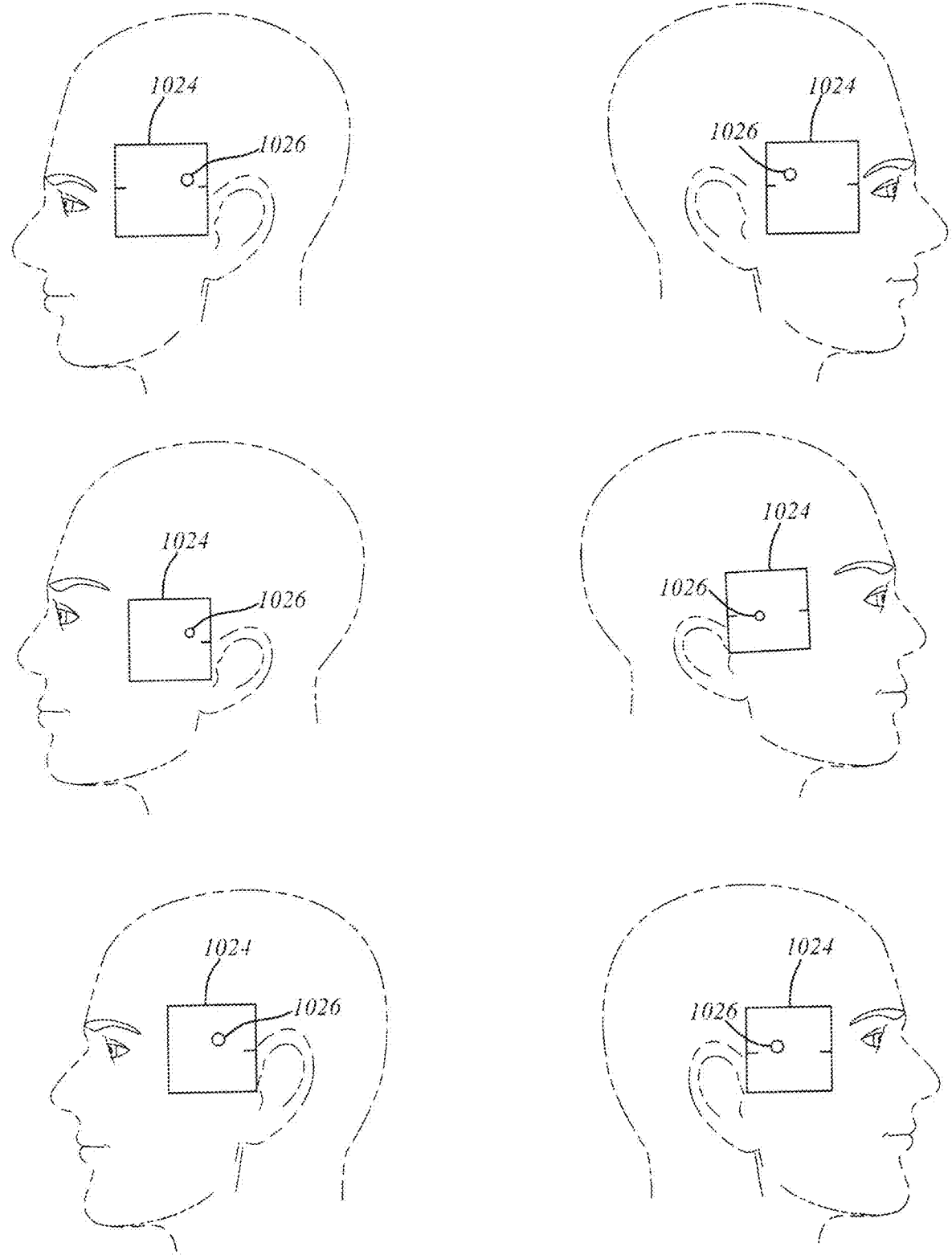
FIG. 18A illustrates example TCD locations.
Figure 18B:
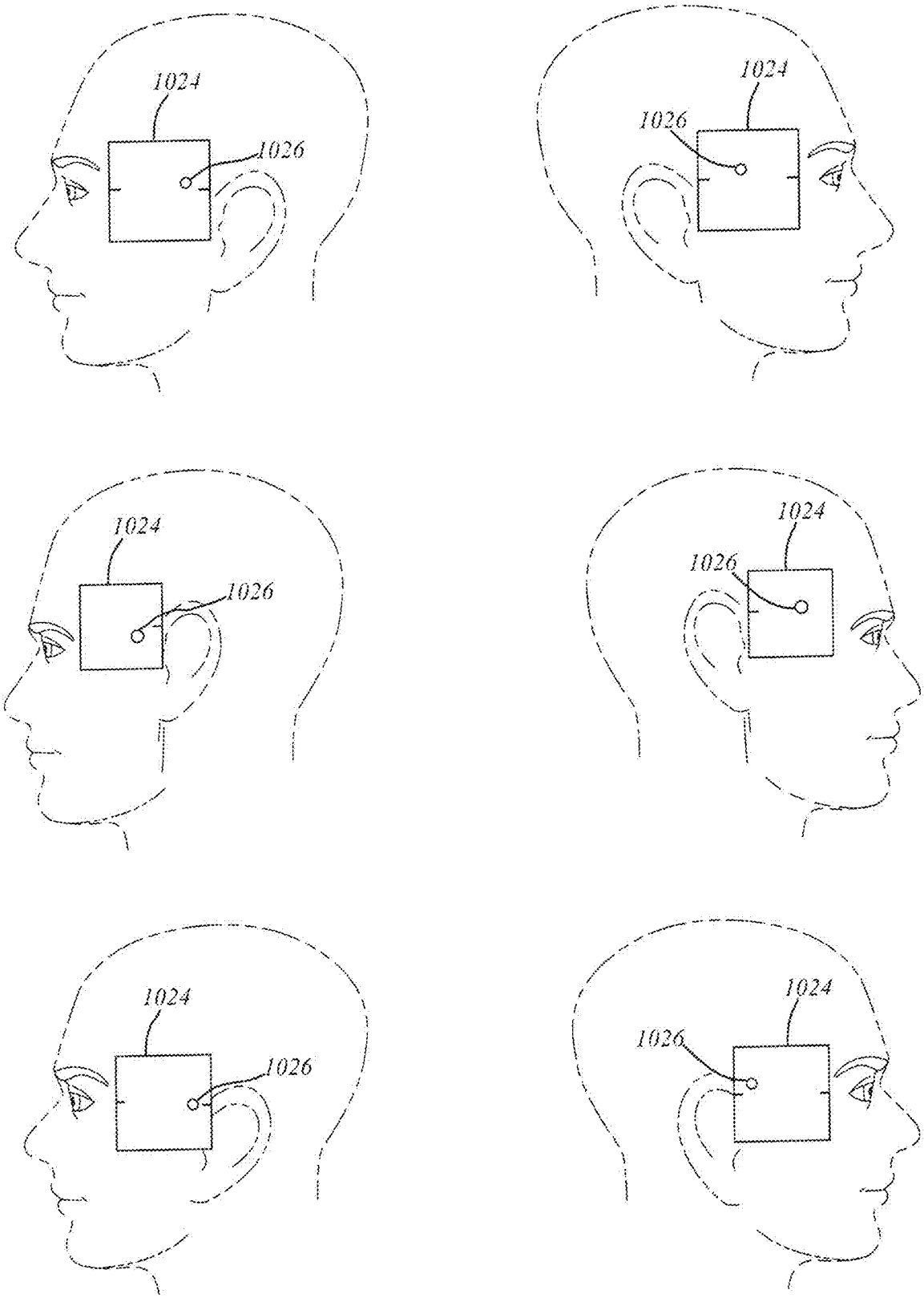
FIG. 18B illustrates example TCD locations.

FIGS. 12-17 correspond to features of Window Discovery. FIGS. 12 and 13 illustrate simple grid search patterns in which a transducer starts at a start location 1000, and moves from one location to the next in a sliding direction 1002 to continuously sweeping over a grid in the X and Y directions a snake like pattern until an end location 1004 is reached. Other embodiments use different search patterns. FIG. 14 illustrates overlapping volumes 1006a, 1006b, 1006c in a target area using multiple transducer positions 1008a, 1008b, 1008c. Reorienting the transducer positions 1008a-c can sweep out a search volume. As shown in FIG. 15, overlapping search volumes 1006a-c can be created by repositioning the transducer positions 1008a-1008c a few times. FIG. 16A, FIG. 16B, and FIG. 16C illustrate TCD sensor 1010 placement for insonating the MCA 1012. FIG. 17 illustrates temporal window 1014 landmarks and limits. Specifically, the anterior limit 1016 is near the orbital bone of the eye 1017. For patient safety, it is preferred not to image near the orbital bone of the eye 1017. The superior limit 1018 is not defined by any specific landmark. The inferior limit 1020 is identified by the zygomatic arch (cheek bone). The posterior limit 1022 is by the ear and provides a natural limit for the temporal window. FIG. 18A and FIG. 18B illustrate example TCD locations 1024 as they vary from person to person, with dots 1026 representing the location of the temporal window.

To locate the temporal window, a transducer is typically placed against the head. In the past, this step was typically assisted by an expert human user. The user placed the transducer against the temple in the approximate location of the window and kept manually reorienting the sensor until the signal was located. A semi-automated device may try to increase signal strength at this point by reorienting the transducer, but with only two degrees of freedom, less than satisfactory results are achieved when attempting to fully automate signal discovery.

According to some embodiments, four, five, six, or even more of degree of freedom (DOF) kinematic mechanisms are used that fully automate the evaluation of the temporal window quality and can rediscover the temporal window even after complete loss of signal, as disclosed below in the section entitled "G. Kinematics."

In some embodiments, with the transducer seated, compliance is kept normal to the surface high enough to keep the transducer seated, but low enough so to be comfortable as the transducer moves in and out following the surface of the head. The X and Y axes can retain a higher servo stiffness in order to maintain precision control of transducer location. Because the normal force of the transducer is determined by the Z axis stiffness, the sliding force encounter by the X and Y axes will be limited to a comfortable level. The transducer can now be directed to perform a search for the TCD window. If the orientation of the transducer needs to be changed, the orientation stiffnesses can be increased via software.

Registration: As discussed in more detail below, in some embodiments, a computer generates commands and directs the mechanism to translate and reorient the transducer along the surface of the head until a candidate signal is located. Once located, the transducer is then automatically reoriented to increase signal strength. Reducing the search time of the automated system to discover the temporal window may be accomplished by a process of anatomical registration involving alignment of the mechanism and transducer at a known anatomical feature, either manually or programmatically.

Figure 19A:
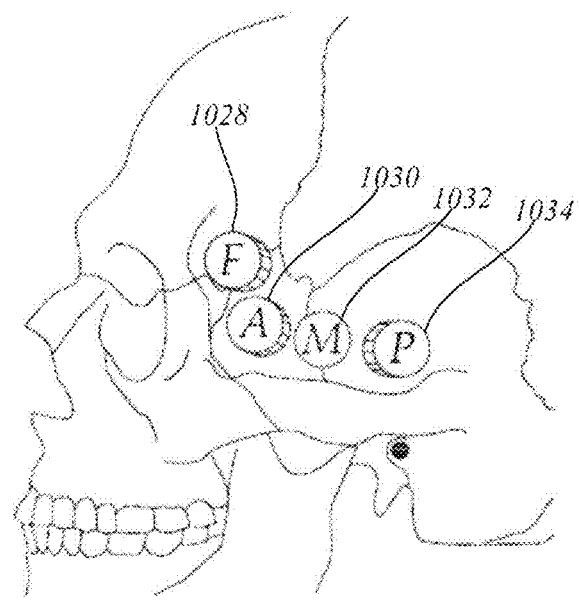
FIG. 19A illustrates the F, A, M, P locations on the temporal window of a skull.
Figure 19B:
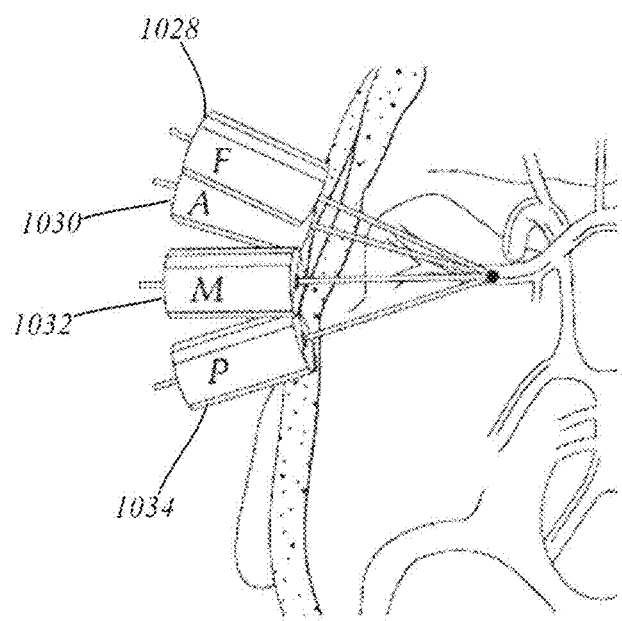
FIG. 19B illustrates insonation of the F, A, M, P locations on the temporal window of a skull.
Figure 19C:
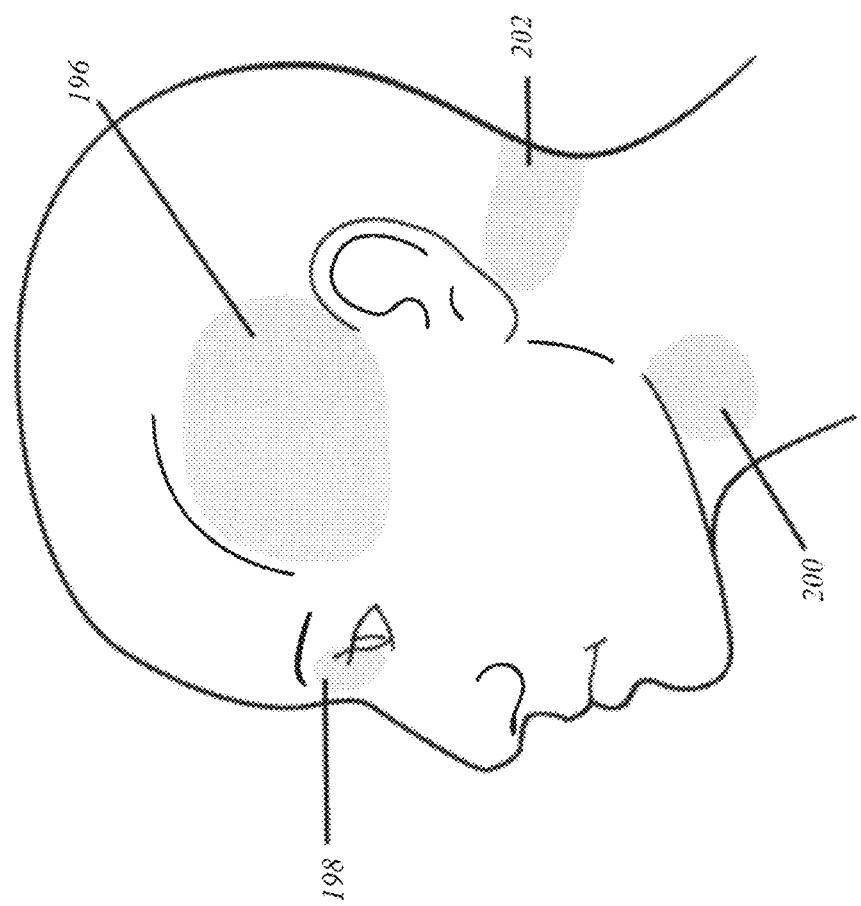
FIG. 19C illustrates various locations that can be insonated on a skull.
Figure 19D:
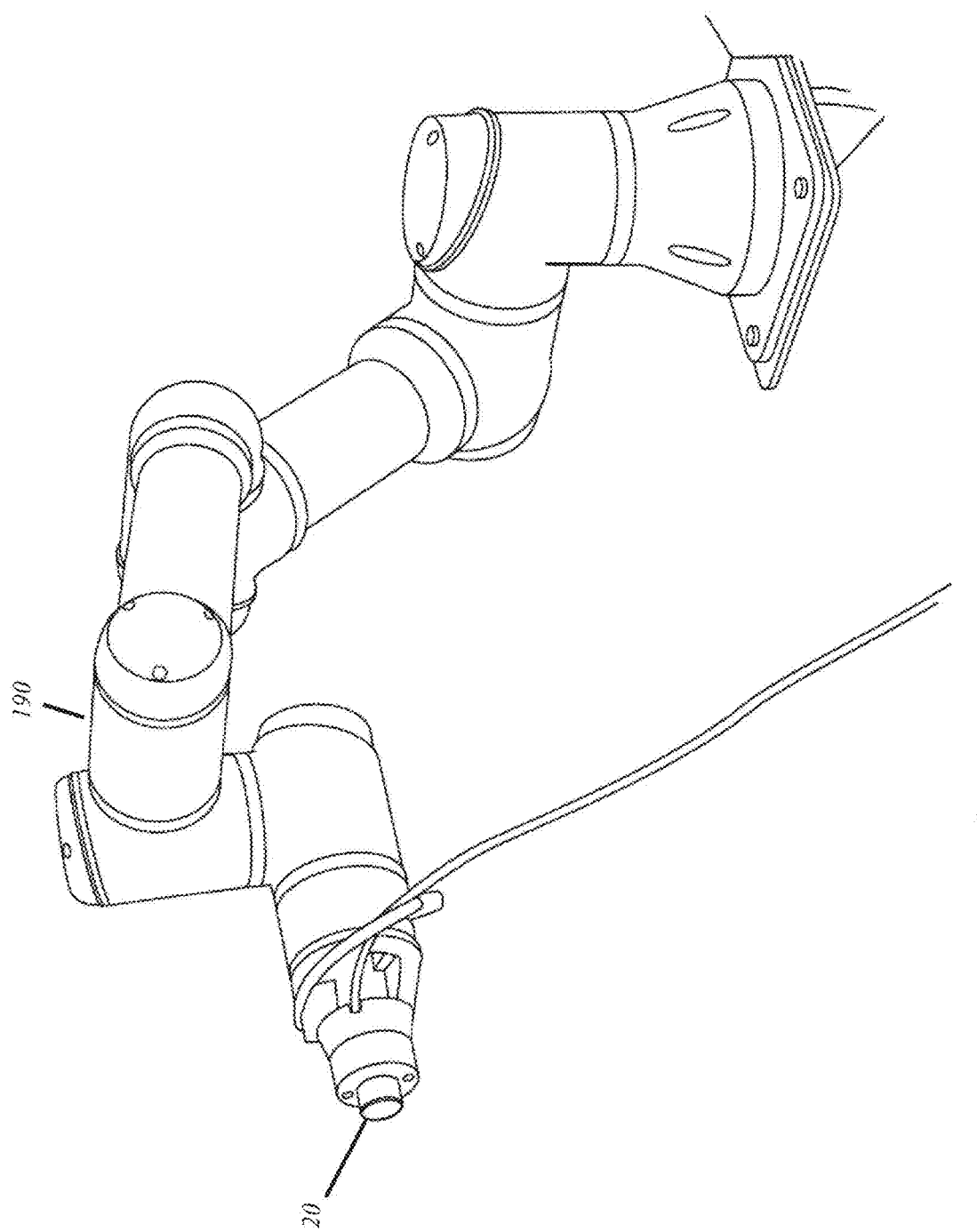
FIG. 19D illustrates a six degree of freedom robot arm with a probe or transducer.
Figure 19E:
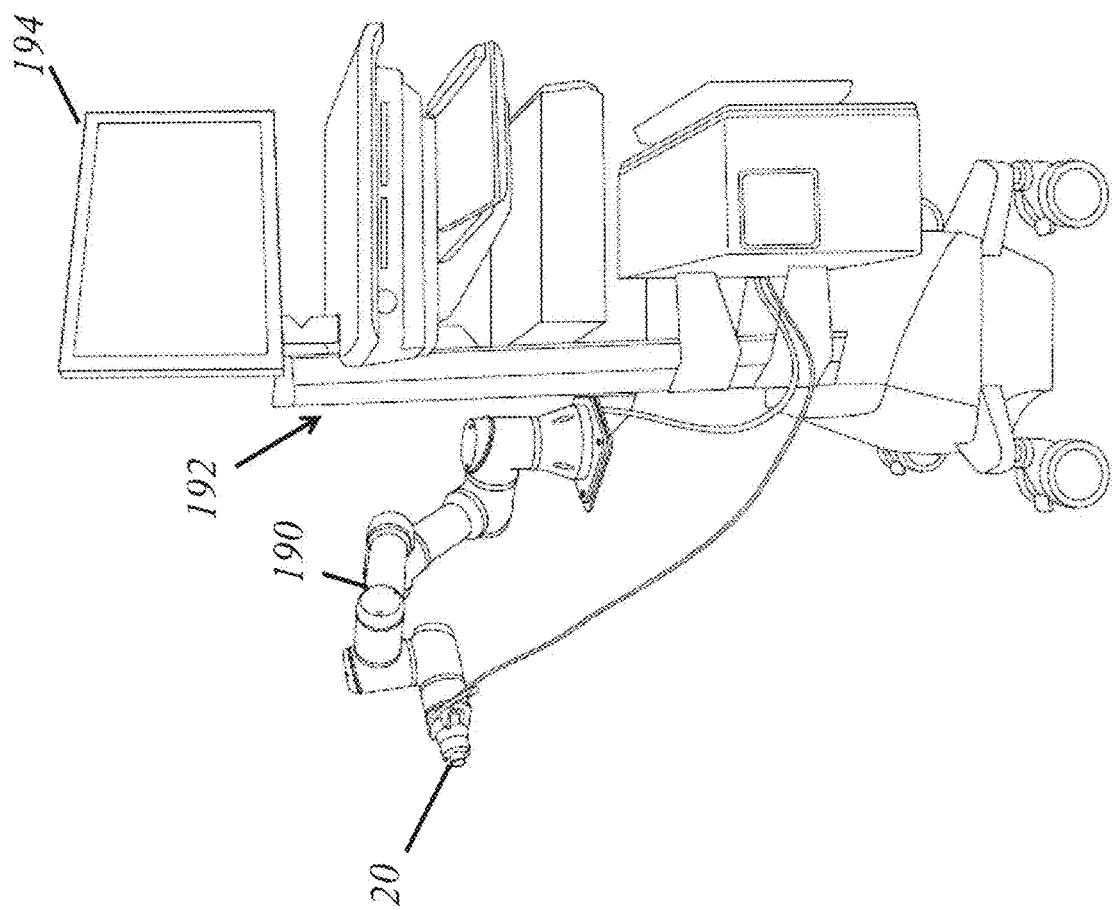
FIG. 19E illustrates a six degree of freedom robot arm mounted with a portable workstation.
Figure 19F:
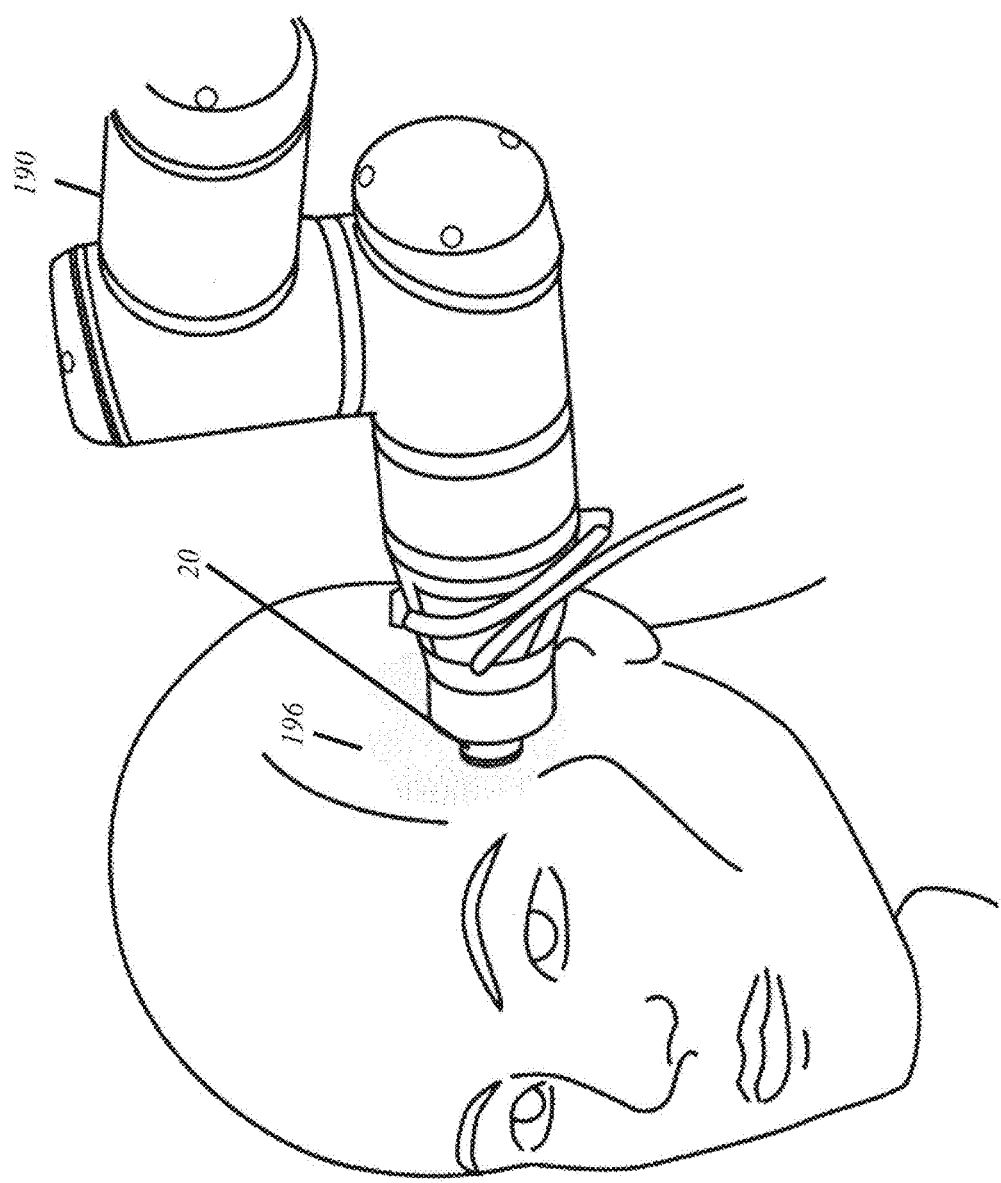
FIG. 19F illustrates a six degree of freedom robot arm insonating the transtemporal window.
Figure 19G:
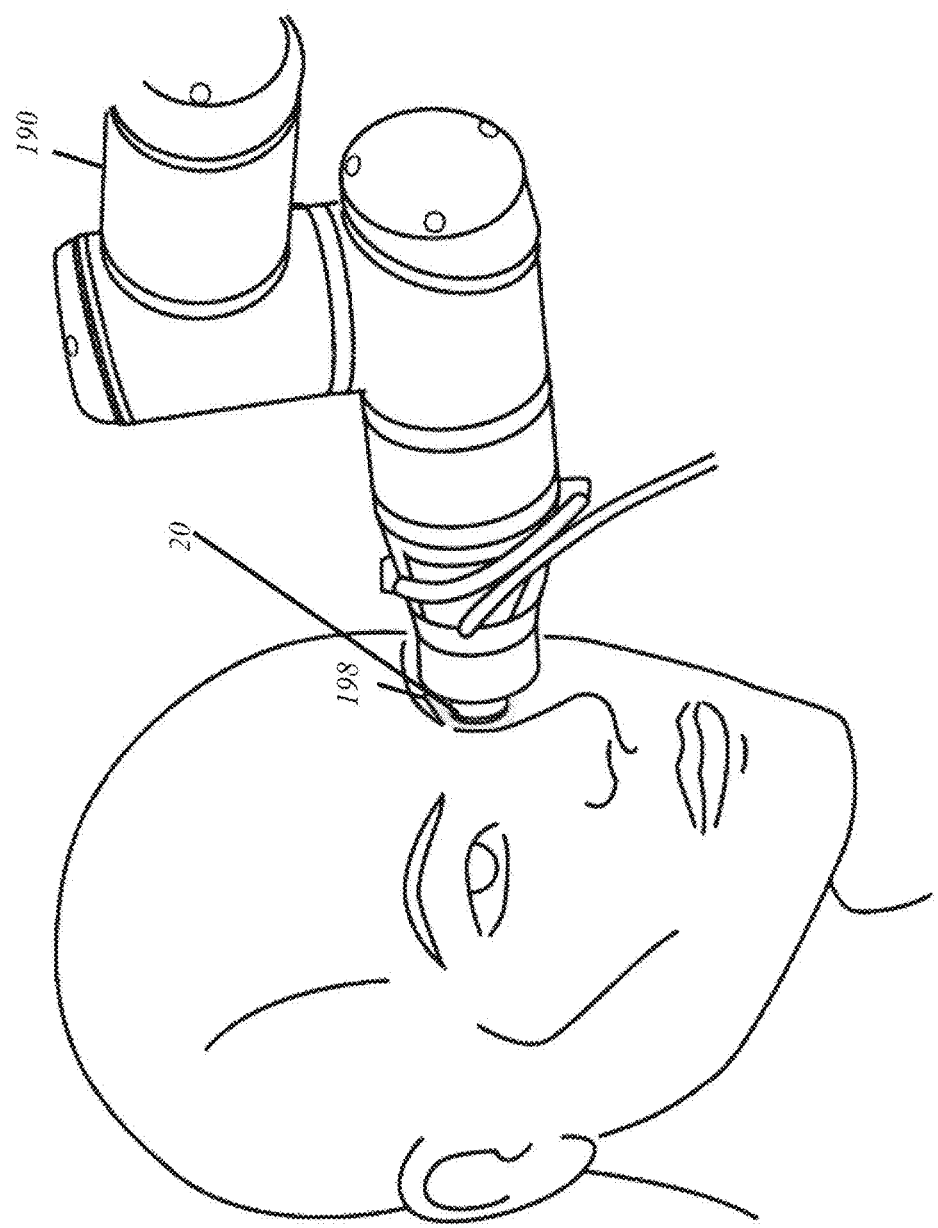
FIG. 19G illustrates a six degree of freedom robot arm insonating the transorbital window.
Figure 19H:
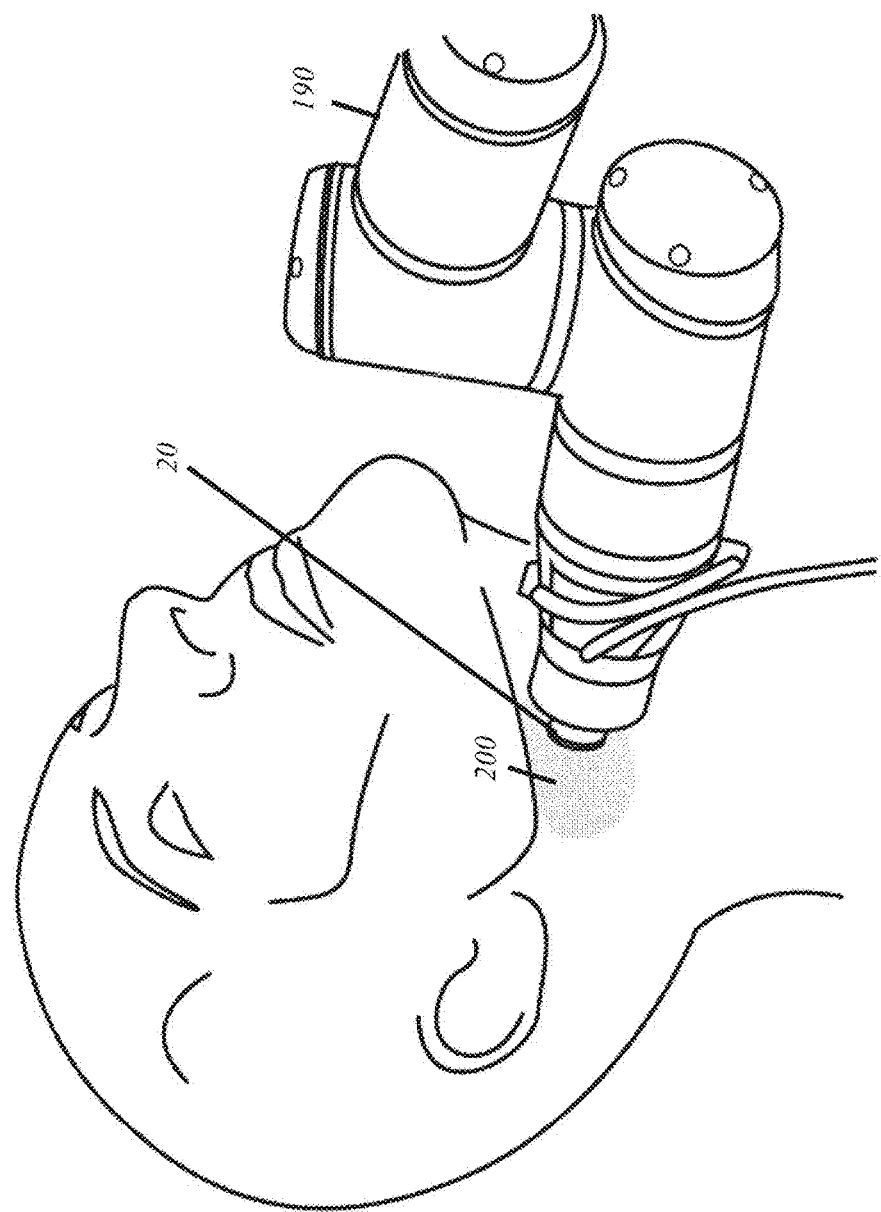
FIG. 19H illustrates a six degree of freedom robot arm insonating the submandibular window.
Figure 19I:
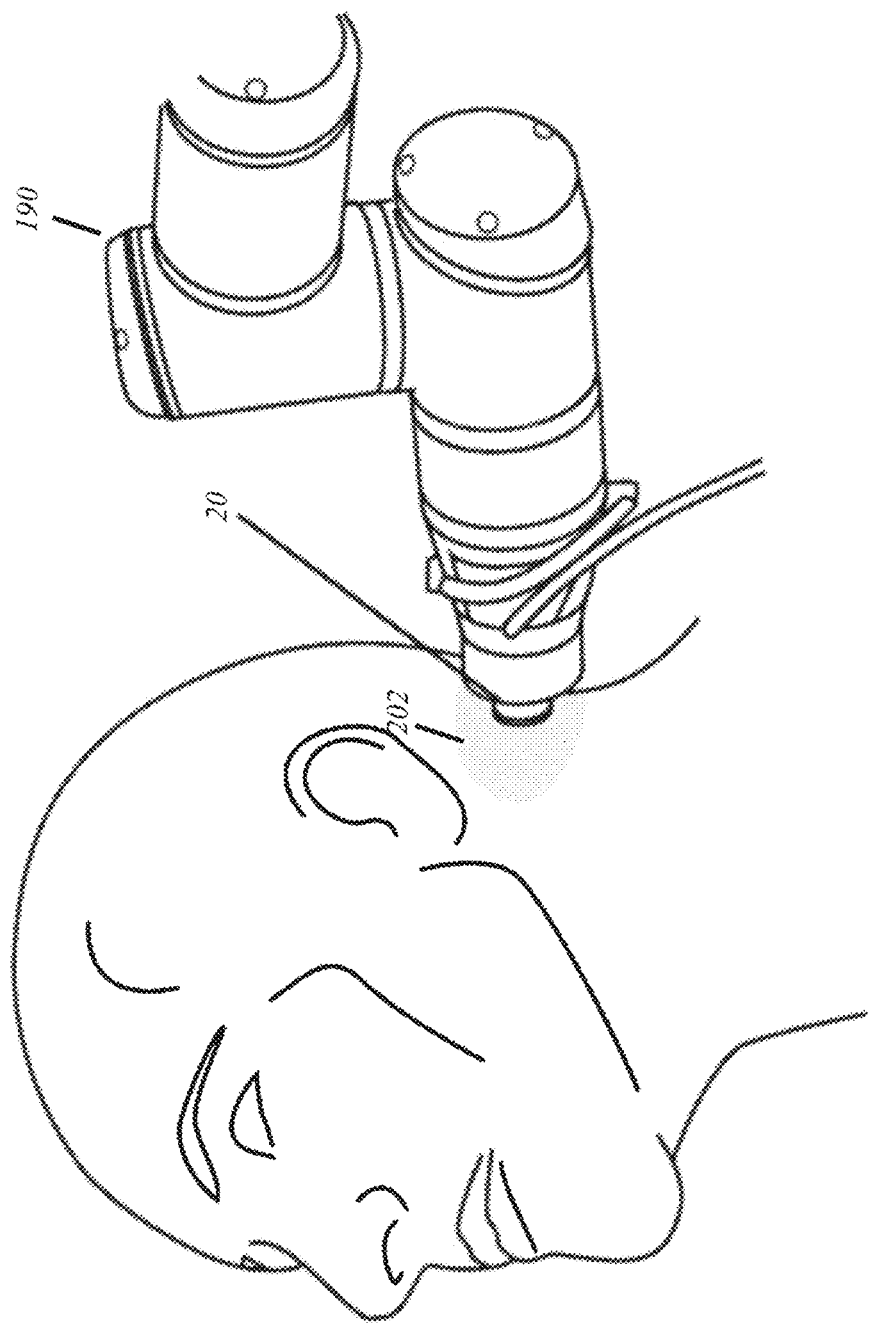
FIG. 19I illustrates a six degree of freedom robot arm insonating the suboccipital window.

Programmatic Registration: If done programmatically, this alignment may be accomplished with a visual window guide for the user to place an initial starting point along the zygomatic arch between ear and the eye. This anatomical registration technique is applicable to TCD, but can also be used with ultrasound, fNIRS, and TCCS. In general the techniques and devices discussed herein specifically described as using TCD can also be employed in various embodiments using TCCS, other known ultrasonic energy modalities, and fNIRS. Specifically, as shown in FIG. 19A, based on existing literature, several different registration points, frontal F 1028, anterior A 1030, medial M 1032, and posterior P 1034, may be used to define a transtemporal search window. Insonation of frontal F 1028, anterior A 1030, medial M 1032, and posterior P 1034 normally occurs both at different x and y locations on the temporal window, as shown in FIG. 19A as well as with different rotational positions of the sensor, as shown in FIG. 19B. Once the transducer is placed at a registration point, the robot is informed of which registration point is being probed. Different registration points could be used depending on which artery is to be insonated. For example, the MCA, ACA, and PCA arteries may be identified using different registration points. FIG. 19C shows various locations that can be insonated, including the transtemporal window 196, the transorbital window 198, the submandibular window 200, and the suboccipital window 202. While registration points for the transtemporal window 196 have been described, other registration points, for the transorbital window 198, the submandibular window 200, and the suboccipital window 202 could also be applied. Once registration points are established, all coordinates are reported relative to the registration points to impose a standard coordinate system across all subjects. For example, in some embodiments, the coordinate (0, 0) would correspond to the posterior limit 1022 of FIG. 17, and the coordinate (1, 0) would correspond to the anterior limit 1016 of FIG. 17. Alternatively, if a scan of a specific subject has been conducted previously, the information already obtained for that subject may be used to conduct registration. As shown in FIG. 19D, a six degree of freedom robot arm 190, which can also be referred to as a redundant manipulator, could be employed to move a transducer 20 to any convenient location on a subject. In other embodiments, the robot has fewer degrees of freedom such as five (x,y,z,pan,tilt) or is underactuated such that one is controlled in part by a spring. As shown in FIG. 19E, the six degree of freedom robot arm 190 could be mounted with a portable workstation 192 that includes a monitor 194. As shown in FIG. 19F the six degree of freedom robot arm 190 could place the transducer 20 at the transtemporal window 196. As shown in FIG. 19G the six degree of freedom robot arm 190 could place the transducer 20 at the transorbital window 198. As shown in FIG. 19H the six degree of freedom robot arm 190 could place the transducer 20 at the submandibular window 200. As shown in FIG. 19I the six degree of freedom robot arm 190 could place the transducer 20 at the suboccipital window 202.

Figure 20:
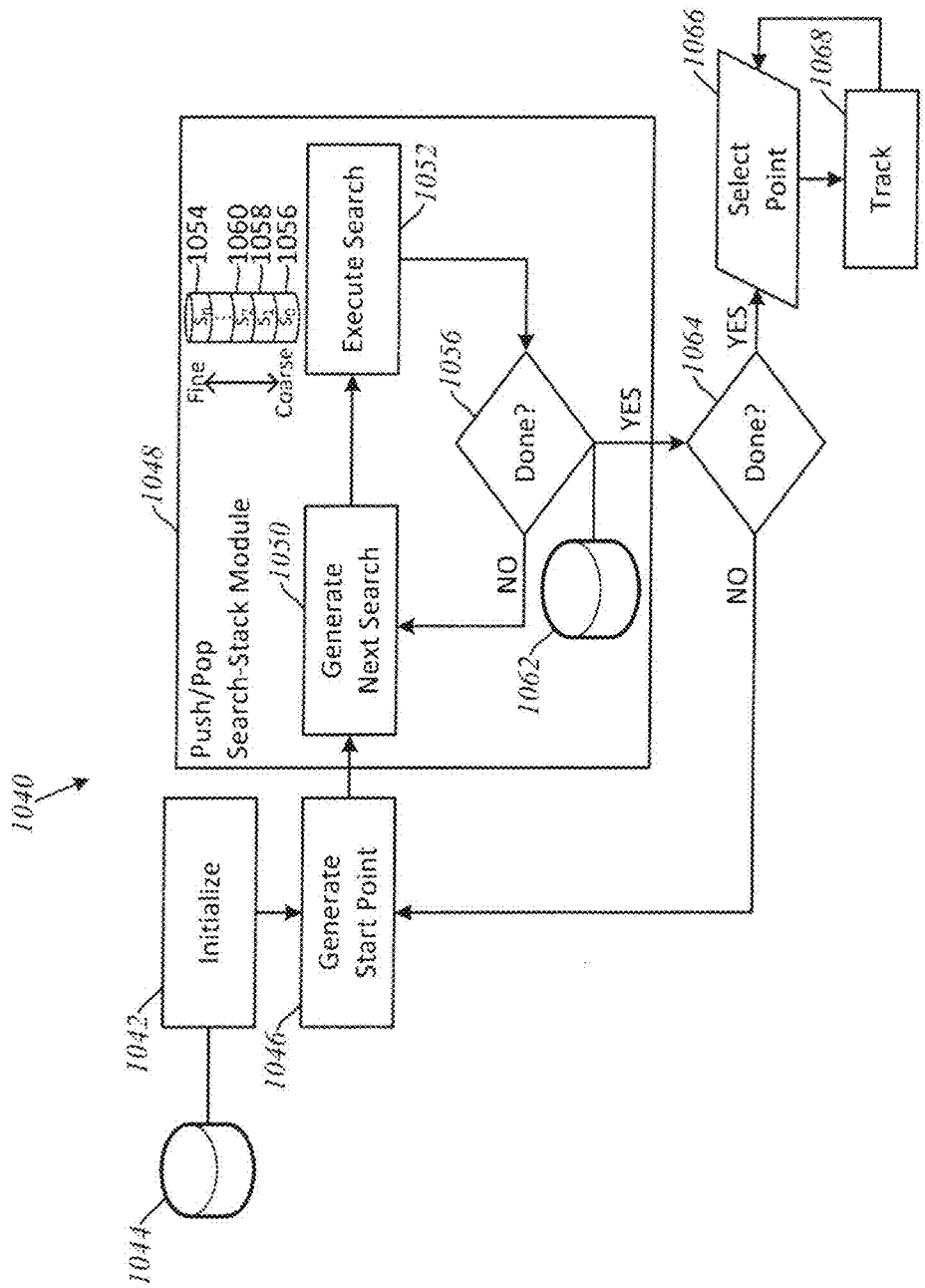
FIG. 20 illustrates a data-driven search algorithm for automatic signal acquisition.
Figure 21:
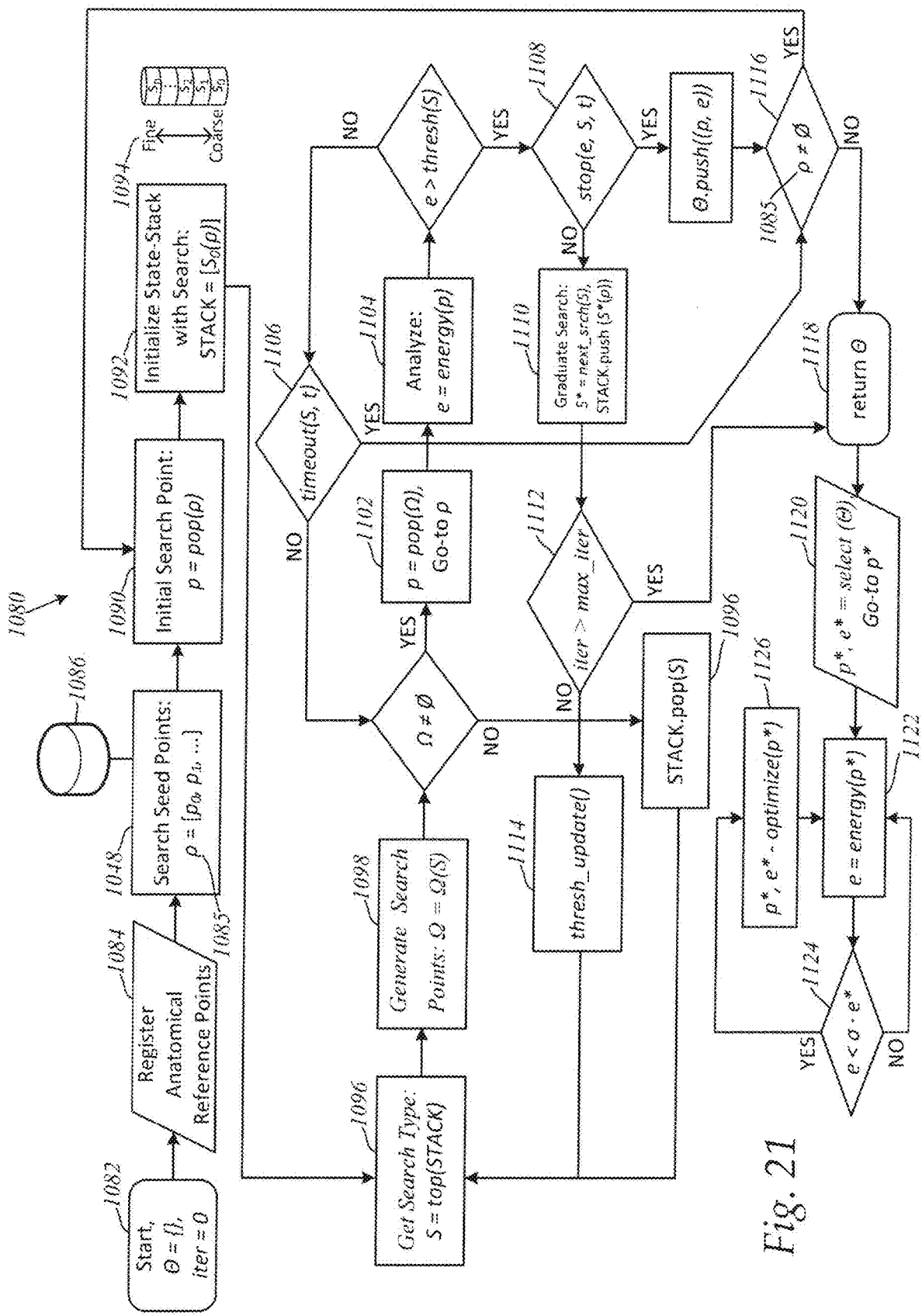
FIG. 21 illustrates a stack-search algorithm.

Automatic Signal Acquisition: Referring to FIG. 20, in some embodiments, automatic signal acquisition may be accomplished automatically using a data-driven search algorithm to identify energy levels exceeding a specified or predefined threshold. The instructions specifying the algorithm may be provided in software, firmware, or other computer readable media. As used in this specification, any software, firmware, or other computer readable information mentioned, may be stored on non-transitory media, such as a hard disk drive, a flash disk drive, in ROM, or other non-transitory media. Specifically, in a system 1040 using a computer to direct the search process, in some embodiments, a stack-search is used. A stack-search allows for optimizing in a global-to-local search paradigm. The functional value that is being optimized is some measure T computed on sensor data, in some embodiments T could represent the energy computed on an underlying TCD signal as acquired by a transducer. Function T, however, is not described by a known underlying distribution, but is instead a black box function with respect to sensor position. Energy values cannot be inferred ahead of time in this type of black box search because the underlying signal distribution is unknown. In some embodiments with a 5 DOF robot and a TCD signal with controllable depth, T is computed by visiting some location position p=(x, y, z, rx, ry, d) and computing T(x, y, z, rx, ry, d), where x, y, z are the translational positions of the sensor, rx, ry are the rotational position of the sensor, and d is the sensor's sample depth. T(x, y, rx, ry, d) is sampled by moving the robot to position (x, y, rx, ry, d) and measuring signal and computing the energy at the position. Before discussing further aspects of the algorithm, some background will be provided.

Energy Computation: Energy computation is a joint function of the M-mode, the envelope, the spectrogram, and the depth, as well as any other information provided by the TCD. A standard energy embodiment can be calculated as either of:

$$\text{Energy}(mmode, env, spec, depth) = \alpha \cdot mmode\_eng(mmode) + \beta \cdot env\_eng(env) + \gamma \cdot spec\_eng(spec) + \delta \cdot depth\_eng(depth) \quad (\text{Eq. 1})$$

$$\text{Energy}(mmode, env, spec, depth) = \alpha \cdot mmode\_eng(mmode) + \beta \cdot env\_eng(env) + \gamma \cdot spec\_eng(spec) \times \delta \cdot depth\_eng(depth) \quad (\text{Eq. 2})$$

Examples of energy for TCD include the following.

Envelope: For the envelope, in one embodiment the time-frequency structure can be determined via a discrete wavelet transform. Wavelet power is obtained at narrow-band scales characteristic of TCD periodicity, e.g., heart rate, P2, and the like, and compared to broad-band power obtained over adjacent scales. Strongly periodic envelopes will have a greater proportion of power at characteristic scales. Noisy envelopes are less likely to show strong concentration of power in any narrow-band because white noise contributes power equally at all scales.

Autocorrelation is a mathematical tool for finding repeating patterns, such as the presence of a periodic signal obscured by noise, or identifying the missing fundamental frequency in a signal implied by its harmonic frequencies. In another embodiment, autocorrelation with a shifted waveform for periodic signals can be evaluated in the following manner, yielding another energy computation possibility. Given that env[t] is the signal at time t, the autocorrelation function at lag l can be expressed as:

$$R_{env}(l) = \sum env(t) \times env(t-l) \quad \text{(Eq. 3)}$$

R will have three strong peaks (besides near zero) and strong valleys between them, indicating a pulsatile waveform with 3 strong frequencies.

env_eng can also be embodied as the time-averaged envelope summed with the time-averaged second derivative of the envelope, enforcing velocities in a particular range, and a forced smoothness.

M-mode: In various embodiments, the width of the M-mode band may be used for calculations. In some embodiments, the summed power in the M-mode may be used for calculations. In some embodiments, the M-mode energies can be masked by a particular depth range if needed for a given vessel search in TCD.

Spectrogram: In various embodiments, the weighted average of the spectrogram signal, weighted by the particular bin number associated with each power value may be used. In some embodiments, the weighted average of the spectrogram signal, weighted by the inverse of the distance from the envelope for each power value may be used. For example, this weighting could be a one-side weighting, where for example all spectrogram data lying above the envelope is counted as zero towards the energy.

Search Optimization: If a simple brute force snake search, as illustrated in FIG. 12 of, for example, a 55 mm by 55 mm transtemporal window were conducted, using a five degree of freedom mechanism that moves along an X axis at 1 mm resolution, a Y axis at 1 mm resolution, a 30 degree by 30 degree X and Y rotational dimensions (rx, ry) and a TCD depth of 75 mm, approximately 200 million points would need to be searched. Such a search would take a significant amount of time. In some embodiments, the search time can be optimized using a data-driven search algorithm implemented on a robotic system searching across a pre-defined area, as discussed below.

Data Driven Searching: Referring again to FIG. 20, in some embodiments, the system first initializes at the initialization step 1042. A database of seed points 1044 may exist. In some embodiments, manual measurements from actual subjects may comprise the database of seed points. Based on measurements from made by technicians, x and y positions of transducer position for the MCA can be used, and the data is clustered using a standard clustering algorithm such as k-means, and the cluster center points are used as seed points into the algorithm.

Referring again to FIG. 20, in some embodiments, the database of seed points 1044 is created by searching seed points via robotic scans of the selected window (e.g., temporal, orbital, sub occipital, submandibular) across a large number of subjects and storing energy computations for points in each window across the entire window. In some embodiments, the computerized robotic system employed has perfect memory, thus allowing for recall of particular signals for a particular subject after the signals have been found. For example, in some embodiments, ACA, MCA, PCA monitoring positions for a particular subject are all stored in memory and the operator can select one of them, commanding the robot to return to that position and display the particular waveform. This ability to recall specific monitoring positions for a particular subject facilitates long term monitoring of a subject because monitoring can be done quickly without needing to start a search from scratch.

Using this technique of generating a database of seed points, thousands of data points can be aggregated across subjects. Layering the collected data across numerous subjects provides a probability distribution of likely window seed points and search biases to speed up the search. Thus, in some embodiments, the search space may be limited by specifying $(x_i, y_i)$ Cartesian coordinates to seed a search at based on high probabilistic chances that a temporal window is found at $(x_i, y_i)$. Additionally, in some embodiments, for a given point (x, y), the transducer rotational orientation is limitless, but the data acquired previously allows for a systematic bias for particular transducer orientations given a set translational point (x, y), greatly limiting the search space. For example, in some embodiments, if the robotics rotational range is ±15° in both pan and tilt, the search range can potentially be limited at a given coordinate if a signal has only been found at the coordinate for a pan of 7-15° and a tilt of 3-10°. In some embodiments, seed points are chosen based on the race, gender, or age of subjects. A generate start point module 1046 then determines an initial start point based on the artery to be scanned.

Push/Pop Search-Stack: In some embodiments, a push/pop search-stack module 1048 is used to conduct the search. In some embodiments, this module is implemented in software on a computer with a central processing unit and associated hardware to monitor information received from a transducer. In other embodiments, this module can be implemented in other types of digital electronic circuitry, or in an ASIC, FPGA, or firmware, or hardware, including the structures disclosed in this specification and their structural equivalents, or in combinations of one or more of them. As is known to those of skill in the art, pushing an element adds an element to the top of a stack. Popping an element removes the top element of a stack. The push/pop search-stack module 1048 contains a generate next search module 1050, an execute search module 1052, a search stack 1054, and an evaluate search value module 1056. At the beginning of a search, no signal has yet been obtained upon which can be optimized. Accordingly, it is preferable to start with a broad, coarse search, which is just looking for a hint of a signal. In some embodiments, an example of the initial search would be a coarse brute force snake search across the entire temporal region, or a coarse spiral/concentric circles centered at the initial seed point.

Each subsequent search is a product of previous searches and their results. As points of interest with strong signals are located, searches will be refined or graduated in the areas of the strong signals. The generate next search module 1050 generates an initial search $S_0$ 1056, which is a very coarse search. In some embodiments, if and when a point of interest is located during the search, a new, finer search $S_1$ 1058 is identified and pushed onto a search stack 1054. For example, if a coarse spiral search is being conducted, and a point of interest is discovered, then a finer spiral search could be pushed onto the state stack. If the fine spiral search finds another point of even higher interest, then an even more refined search would be pushed onto the state stack and thus conducted. If search $S_1$ 1058 generates useful additional points of interest, an even finer search $S_2$ 1060 is generated and pushed on the search stack 1054, and so on. In some embodiments, the "point of interest" energy threshold is increased or made more strict as the searches become more refined. In general, if a search $S_n$ does not generate any useful additional points of interest, search $S_n$ is popped off the search stack 1054 and that search state returns to the state it was at during search $S_{n-1}$ and continues using the potentially less strict energy threshold as was specified for $S_{n-1}$.

After each search is executed by the execute search module 1052, an evaluation of the returned value of the execute search module 1052 is made by evaluate search value module 1056. If the returned value of the execute search module 1052 does not satisfy a finishing criteria, then a new search is generated by the generate next search module 1050, and the cycle continues. If the returned value of the execute search module 1052 does satisfy a finishing criteria and the signal obtained is sufficiently useful, the evaluate search value module 1056 exits and the returned value of the execute search module 1052 is added to a set of useful points 1062 and the search stack 1054 is cleared. Next, the end of search decision module 1064 determines whether sufficient number of useful points have been identified. If a sufficient number of useful points have not been identified, the generate start point module 1046 generates a new search and the cycle continues using the next seed point. In another embodiment, all search points visited and their corresponding energies are stored in a sorted list. This list can be filtered to keep only the best energies given some spatial resolution constraints. The top of the list has the highest energy points and these represent the useful points for the next part of the algorithm.

If a sufficient number of useful points have been identified, the search algorithm terminates. At this step, the select point module 1066 may ask an operator, or may decide automatically, whether any point located in the prior searches is of interest. Once a point of interest is selected, the track module 1068 directs a robotic mechanism to move to the point of interest and analyze the signal. In some embodiments, the point of interest may be selected based on computed energy value (e.g. the highest energy is assumed to be the best point) or based on metadata such as a point label (e.g. MCA, ACA, PCA for TCD). In some embodiments, the system 1040 will then monitor that point, continuously tracking the energy at that point. In some embodiments, if the energy degrades by a certain percentage (e.g., 10% degradation), the system 1040 will then conduct a local optimization near that point, using a track module 1068 to re-acquire the ideal signal. This re-acquiring of the signal is significant because patients often move or talk, causing the system 1040 to lose the signal. In some embodiments, at any point, the operator may select a different point of interest to examine.

Referring to FIG. 23, in some embodiments of a stack-search algorithm, a system 1080 using a computer programmed with software to direct the stack-search process, has an initialization module 1082 which initializes variables. The system 1080 then registers anatomical reference points in the register anatomical reference points module 1084. A database of seed points 1086 may exist, which contains a set of seed points ρ 1085, which may be used by the search seed points module 1088 to determine which seed points to search or the search seed points module 1088 may use information received from the register anatomical reference points module 1084. The database of seed points 1086 may be stored on non-transitory computer readable media. An initial search point module 1090 then determines an initial seed point "p" to search and provides that point to the initialize state-stack search module 1092. The initialize state-stack search module 1092 creates a search stack 1094 based on seed points p.

In some embodiments, a get search type module 1096 determines a search by popping the top element off the search stack 1094 and provides the search type S to the generate search points module 1098. The generate search points module 1098 generates a set of points to search Ω based on the search type S. If no additional points exist in the set of points to search Ω, then the top element of the search stack 1094 is popped off by the stack pop module 1100 and provided to get search type module 1096 and another search type S is retrieved from the generate search points module 1098.

In some embodiments, if points exist in the set of points to search Ω, the point identification module 1102 identifies a point p to search by popping it off the top of the set of points to search Ω and directs the robotic mechanism to go to point p. The analyze energy module 1104 then analyzes the energy e received from the energy directed at point p. If the energy e is below a specified energy threshold, possibly indicating that a vessel has not been located, in some embodiments a search timeout decision is implemented via timeout module 1106. Search timeouts have special utility in time-critical situations, such as a stroke diagnosis in which emergency medical intervention may be required. In some embodiments the duration of the search timeout is a pre-defined interval of time used for every search. In some embodiments, the duration of the search timeout is dynamic that changes. In some embodiments the duration of the search timeout updates every time the finest search $S_N$ is conducted, and the duration of the search timeout may either be increased or decreased, depending on the desired outcome, for example increasing search thoroughness, or increasing search speed. In some embodiments the duration of the search timeout may be based, in part, on the amount of time spent searching.

In some embodiments, if no search timeout is taken and there are more points to search in the set of points to search Ω, the next point p is identified by the point identification module 1102 and the cycle continues. Alternatively, if there are not more points to search, the get search type module 1096 determines a search by popping the top element off the search stack 1094 and the cycle continues.

In some embodiments, if a search timeout is taken then the evaluate seed point set module 1116 evaluates whether the set of seed points ρ 1085 constitutes the empty set Ø. If the set of seed points ρ 1085 does not constitute the empty set Ø, then initial search point module 1090 generates a new initial point to search and the cycle continues. Alternatively if the set of seed points ρ 1085 does constitute the empty set Ø, then no more seed points exist and the set of candidate points ⊖ 1118 is returned. Then in the user selection step 1120, the user then selects a point p*, and its corresponding energy e* from ⊖ 1118 and the robot is directed to go to point p*. Track mode is then entered, as discussed above. In the compute energy module 1122, the system continuously computes the energy e at p*. The compare energy module 1124 determines whether e falls below some fraction σ of the original energy e*. If compare energy module 1124 determines that e has fallen below some fraction σ of the original energy e* then the optimization module 1126, re-optimizes, computing a new point p* and its corresponding e*.

Referring again to the analyze energy module 1104, if the energy e is above a specified energy threshold, then the stop determination module 1108 makes a determination as to whether to stop the search. In some embodiments, the determination to stop the search may be based on some combination of the amount of energy e received, the search type S, or the time spent searching.

In some embodiments, if the stop determination module 1108 determines that the search should not stop, then the graduate search module 1110 identifies the next search to conduct and pushes onto the search stack 1094 a finer search.

In some embodiments a maximum search iteration module 1112 determines whether the maximum number of searches allowable has been conducted. This maximum search iteration module 1112 provides a method of limiting the time spent searching. In some embodiments, the maximum search iteration module 1112 may base the decision regarding whether the maximum number of searches allowable has been conducted on some combination of the total time spent searching, the total number of iterations of searching conducted, or the total number of searches conducted at the finest search time $S_N$.

In some embodiments, if the maximum number of iterations has not been reached then a threshold update module 1114 may perform a dynamic threshold update for the minimum acceptable energy level. In some embodiments, it is important to update this threshold because there are significant anatomical differences among subjects. Some subjects have very poor signals and the embodiment may be required to obtain the best signal possible in a predefined amount of time, so thresholds are initially set low. Other subjects have very strong signals, and using the same thresholds on these subjects as were used with the poor signal subjects will result in poor final signals compared to what they could ultimately be yielded if higher thresholds were imposed. In some embodiments, dynamic thresholds will be updated after the completion of each successful search, and the threshold will be updated to increase the difficulty of locking onto a signal during the next iteration of the search cycle.

TCD Search and Signal Processing Algorithm: The problem of an automated TCD system with a path planning and signal processing algorithm that searches for a TCD signal while directing the general motion of the transducer, can be separated from the robot control problem of being able to automatically follow a contoured surface (as would be found on a head). The rationale for this separation is that the detection algorithm is a signal processing and motion-planning problem that encapsulates some of the innovation. The interaction is with a small area of the head that can be simplified to a nominally 2D surface, which puts the focus of this objective on the planning and signal processing algorithm development. Having a transducer follow a contoured surface while maintaining a normal angle is a technical task that extends the applicability of the system eventually to human subjects, but is not dependent on TCD signal interpretation. In some embodiments, the system can deploy an ultrasound transducer against a contoured 2-d surface, and slide the transducer at constant velocity while maintaining a constant normal force between 2 and 10 Newtons.

Search Types: In various embodiments of the search system, many different types of searches may be employed. Specific search types are discussed below.

Grid Search—Cartesian: The simplest window and signal discovery is a brute force approach. In some embodiments, a five degree of freedom robot is used. Given a bounded search area, the search algorithm will direct the robot to place the transducer onto the flow phantom interface and then move it through a Cartesian grid of discrete points in a segmented step size, stopping to check the velocity envelope signal at each point. As discussed in more detail below, in some embodiments, the TCD transducer will also need to be set to a grid of sample depths to find the maximum signal at that point. Once the grid is complete, the location of the maximum signal can be determined and the transducer repositioned to that location, as illustrated in FIGS. 12 and 13. In some embodiments, the dimensions are X, Y, rotation in the X axis, rotation in the Y axis, and depth of insonation, or TCD depth, which step sizes are represented by dx, dy, drx, dry, ddepth, respectively. As noted above, using a relatively small step size such as 1 mm, a snake/grid search may be inefficient and time consuming. Using a coarser step size, which greatly prunes the number of searches conducted, such a snake/grid search may be appropriate for imprecise studies, such as window mapping.

This algorithm also sets a baseline performance metric to compare other algorithms to. For one version of the algorithm, the string phantom is set to a constant velocity, simplifying the signal detection to checking the magnitude of the velocity envelope. Once constant velocity can be detected, the complexity of the problem will be increased by setting the string phantom to mimic pulsatile flow. In some embodiments, what is used is perhaps simplest pulse detection algorithm, which employs a band pass filter centered at the beat frequency to determine presence and magnitude of the TCD signal.

In order to reduce the time for the optimal TCD velocity signal to be found, or a TCD velocity signal exceeding a predefined threshold, the transducer will be constantly moving while the search algorithm checks the sensor data, as illustrated in FIGS. 12 and 13. Complicating this task is that transducer motion can couple into the output signal yielding false positives. In some embodiments, implementing this algorithm involves characterizing the motion coupling noise into the transducer output to determine the maximum scan speeds and signal filters to ameliorate the noise. For example, during the constant velocity string phantom case, noisy signals are sometimes generated, and a low pass filter may be used to decouple the noise due to transducer motion sliding artifacts from the DC velocity signal coming from the string phantom. In some embodiments, for pulsatile motion a band bass filter or other probabilistic detection method, such as a Bayesian filter may be used.

Grid Search—Cartesian and Orientation: The magnitude of the velocity signal is proportional to the Doppler angle as a function of the cosine, $v_z = \|\vec{v}\| \cos \theta_D$. changing the orientation of the transducer can affect the quality of the signal. Changing the transducer angle also allows for searching a volume for the target vasculature at one location instead of just emitting a line of projected ultrasound acoustical energy, as shown in FIG. 14. This algorithm repeats the Cartesian grid search adding a grid of orientation angles of the transducer (pan and tilt) to sweep out a search volume. By triangulating on the maximum signal location, this search picks an optimal transducer orientation and position that may differ from the Cartesian only grid search. Overlapping search volumes can be created by repositioning the transducer a few times.

Simulated Annealing: Another search type used in some embodiments is simulated annealing. Simulated annealing is a search method known to those of skill in the art. Simulated annealing provides a method of determining a likely good, but not necessarily optimal, solution to an optimization problem. In general, and simplified, terms, simulated annealing searches for the best solution by generating an initial solution at random and then explores the area nearby randomly to generate a new solution. If the new solution is better than the current solution, the new solution replaces the current solution, and it is saved as the base of the next iteration. Alternatively, if the solution in the neighboring vicinity is worse, the algorithm calculates an acceptance probability and compares it to a random number. If the acceptance probability is higher than the random number, the new solution replaces the current solution, it is saved as the base of the next iteration. Otherwise, the new solution does not replace the current solution.

Spiral Search: Another search type used in some embodiments is a spiral search. A spiral search originates at a seed point. The search can be coarse or fine, depending on the application. Instead of moving along an X axis until an end is reached and then adjusting the Y direction as in the Cartesian search, a spiral search adjusts angular separation simultaneously in the X and Y directions to make the transducer spiral outward from the initial seed point. A coarse spiral search expands more quickly than a fine spiral search.

Concentric Search: Another search type used in some embodiments is a concentric search. A concentric search starts at a seed point as the initial position and then typically adjusts either the X or Y direction to come to a new position defining a radius from the initial position. From the new position, the search adjusts both the X and Y axes to search in a circle. Once the starting point of the circle is returned to, another radial adjustment is made and a search of the new circle is conducted.

Hill Climb: Another search type used in some embodiments is the hill climb. The hill climb technique is another technique known to those of skill in the art for efficiently finding local optima that can be used in various embodiments. In general, and simplified, terms, a hill climb technique starts at a seed point as the initial position. The initial position is analogized as the base of a hill. The technique then repeatedly improves the solution finding a better signal, which is analogized to walking up a hill, until some condition is maximized and a satisfactory signal is found.

Contra-lateral Search: Some technicians have reported that a signal acquired on the ipsilateral is often reflected, position-wise, in the contra-lateral side. In some embodiments, this domain knowledge is exploited in embodiments of the search algorithm. Specifically, in some embodiments in which a bilateral scan is conducted, if a signal is detected, for example, on the contra-lateral side, the position and signal strength information will be provided to the processor conducting a scan on the ipsa-lateral side, and vice versa. Continuing with the example, the processor for the ipsa-lateral side then assess the broadcasted signal strength and makes a determination of whether a search should be started centered at the symmetric point provided by the contra-lateral side. In some embodiments, this search can either be done by immediately abandoning the current search and moving to the point, or adding the symmetric point to the list of seed points for the algorithm.

D. Vessel Signal Optimization

In some embodiments, once the system has placed the transducer on the skin (See Automatic Transducer Placement) and identified a candidate window (See Automatic Window Discovery), the embodiments then identify the optimal signal, as discussed above. In currently existing manual systems, this optimization is sometimes being done by the technician "optimizing" the transducer angle, sound, depth, waveform fit, spectrum.

Overview: In some embodiments, signal optimization is important. For TCD, the strength of the echoed blood flow velocity signal strength decreases as a cosine function of the angle of incidence between the ultrasound beam and the blood flow. For purposes of a machine learning algorithm, a loss of signal can disrupt the final diagnosis. Many external factors can cause signal weakening: TCD transducer slippage relative to the head, mechanical creep in TCD head mounted fixtures, patient motion, and the like. Even just achieving and maintaining the maximum signal is difficult for an expert user. Fundamentally, all of these problems center on minimizing the angle of incidence of the ultrasound beam and the blood flow.

In some embodiments, controlling for this angle incidence requires placing the sample beam location of the TCD sensor in Cartesian space, (x,y,z), onto the arterial structural, and then minimizing the orientation error (angle of incidence) between the direction of the beam and the direction of the blood flow. Setting the orientation of the sample location requires two degrees of freedom—pan, tilt. In total a minimum of five degrees of freedom must be used to kinematically guarantee at least one solution where the orientation error is zero (or as close to zero as possible has defined by the limits of TCD window anatomy and vessel orientation). Some currently available TCD products automatically control for only the two orientation degrees of freedom.

Some embodiments provide a five DOF mechanism that when coupled with a TCD sensor, controls the depth setting of the TCD. This mechanism creates a virtual link to the ultrasound sample location within the brain and in total a six DOF kinematic chain. In some embodiments a redundant manipulator also exists that can adjust itself with small motions while maintaining maximum signal strength. In some embodiments, a sample volume is placed at a three dimensional location within the vessel and the orientation of the sample is adjusted to align itself with the vessel blood flow in order to minimize the angle of incidence, which increases signal strength.

Limitations of Current Two DOF Systems: It is important to note the limitations of two degree of freedom systems. Currently available TCD system with two automatic DOFs and control of the TCD depth as a third DOF, can place a sample volume within the brain at a Cartesian location (x,y,z). With only three total degrees of freedom, the orientation of the sample cannot be specified. Therefore, the angle of incidence to the blood flow cannot be set so there is no guarantee of the signal strength. The angle can only be adjusted by the user manually moving the transducer. Signal acquisition and optimization remains a manual process, with the fundamental geometry unlikely to be understood by the user.

Optimizing Signal Strength: With a five DOF mechanism, and using the depth setting of the TCD transducer, the sample volume Cartesian location (x,y,z) and orientation (pan,tilt) can be specified. For the device, the following describes a relationship between the input mechanism and TCD settings, $Q=\{q_1, q_2, q_3, q_4, q_5, TCD_{depth}\}$ to the sample volume location and orientation X={x,y,z,pan,tilt}, which is called the forward kinematics $$X = \text{fwd\_kin}(Q)$$

Similarly an inverse relationship called the inverse kinematics can derive mechanism settings Q from a desired sample location and orientation, X.

$$Q = \text{inv\_kin}(X)$$

For a given Cartesian location within the brain (x,y,z), pan and tilt can be adjusted to maximize the signal strength by minimizing a cost function based on orientation error.

Use of a Redundant Degree of Freedom: When the mechanism is able to press the transducer into the head because of skin and tissues compliance, there is a brief area before the z motion of the transducer into the head becomes constrained where there are six controllable degrees of freedom. In this region, there is one extra degree of freedom which creates a redundant kinematic chain. The mechanism can now reconfigure itself, from $Q_1$ to $Q_2$ while maintaining the sample position and orientation X via the relationship $$\Delta q = J^\dagger \vec{e} + (I - J^\dagger J)\varphi$$

where $\Delta q$ is the change in mechanism configuration, J is the Jacobian which relates differential joint motion Q to differential task space motion X, $J^\dagger$ is the pseudo inverse of the Jacobian, $J^\dagger \vec{e}$ is the term that corrects for sample position error, and $(I-J^\dagger J)\varphi$ is the null space that maps a desired change in Q into a $\Delta q$ that does not affect X.

This extra degree of freedom allows for multiple approaches or mechanism configurations to signal discovery and maintenance. It also allows for repositioning of the mechanism while maintaining signal lock.

It is important to note that the Z action of the device must not be coincident with depth action of the TCD, or a degree of freedom will be lost. This approach only works while the mechanism can move the transducer within the compliance of skin.

Gradient Descent and Optimizing Signal Strength after Lock: Some embodiments are not limited to straight line, constant velocity moves. As the transducer motion commands can be updated in real time at a rate of at least 125 Hz, other non-linear search paths can be created. By taking advantage of being able to change the orientation of the transducer and the depth information from M-Mode, a gradient descent algorithm can be implemented that maximizes a TCD velocity signal. Once the candidate location is found, the signal strength at the current transducer location can be optimized by reducing the Doppler angle. This optimization will result in more rapid detection of a the TCD signal. The approach for signal strength optimization is as follows:

Optimization of Blood Velocity Signal from TCD Measurements Using a Robotic Device: When measuring the blood velocity using a TCD sensor, maximizing the signal strength is important for analysis. Signal strength is dependent on the Doppler angle, $\theta_D$, between the blood velocity vector, $\vec{v}$, and the orientation of the normal to the TCD sensor surface or emission axis, $\vec{z}$. The measured velocity along the TCD emission axis, $v_z$, varies as function of the cosine of the Doppler angle.

$$v_z = \|\vec{v}\| \cos \theta_D \quad \text{(Eq. 4)}$$

The optimization of this relationship is to simply minimize the Doppler angle.

Approach: In some embodiments, a robotic device holds the TCD sensor while collecting data from a section of the cerebral artery. The position and orientation of the TCD sensor is known from the robot kinematics. Because the depth setting of the TCD is also known, the position of the sample within the brain can be thought as the final step of the kinematic chain of the robot. This sample has the same orientation as the TCD sensor. The measured velocity should be a function of the Doppler angle between the sample normal axis $\vec{z}$ and the blood velocity vector, $\vec{v}$ as described through Eq. 4. In some embodiments, the robotic device can reorient the TCD sample while maintaining its position. The TCD sensor itself will need to change position and orientation, but the location of the sample in the brain will remain constant. At each reorientation, the Doppler angle changes and the new velocity is measured. Given a collection of enough sample orientations and their respective velocity measurements, and the relationship described in Eq. 4, allows for solving for $\vec{v}$ which will determine both the optimal orientation to collect TCD data, and predicts the maximum blood flow.

Analytic Solution: Assume that the origin reference coordinate frame is the beginning of the robot kinematic chain. The orientation of the sensor can be described by a coordinate frame attached to the surface of the TCD transducer with the Z axis normal to the surface. This coordinate frame can be derived from the robot's forward kinematics and is described by a rotation matrix. The columns of a rotation matrix are the orthogonal unit axes of frame n written in the coordinates of frame 0.

$$_n{}^0 R = [\vec{X}\,\vec{Y}\,\vec{Z}] \quad \text{(Eq. 5)}$$

If this coordinate frame is translated a distance d equivalent to the sample depth setting of the TCD sensor, it will now lie coincident with the blood flow velocity vector, $\vec{v}$, that is being measured. The orientation of the axis of emission of the TCD sensor is described by the z-axis of the rotation matrix in Eq. 5, $\vec{Z}$, which falls out of the kinematics. The angle between the two vectors is the Doppler angle. The angle between the two vectors can be related with the vector dot product $$\vec{Z} \cdot \vec{v} = \|\vec{Z}\|\|\vec{v}\| \cos \theta_D \quad \text{(Eq. 6)}$$

The magnitude of $\vec{Z}$ is already normalized. By normalizing $\vec{v}$ Eq. 6 reduces to $$\vec{Z} \cdot \vec{v}_{norm} = \cos \theta_D \quad \text{(Eq. 7)}$$

For each measurement made at a set position $\vec{P}$ with a different orientation $_n{}^0 R$, a measured velocity $_n v_z$, is generated with a z-axis orientation, $_n \vec{Z}$ where the measurement index is n=1, 2, 3 . . . . The analytic solution can be derived by substituting Eq. 7 into Eq. 5 and making three measurements to generate three equations.

$$_n v_z = \|\vec{v}\|(_n z_1 v_{norm,1} + {_n z_2} v_{norm,2} + {_n z_3} v_{norm,3}) \quad \text{(Eq. 8)}$$

Making a substitution of variables $c_1 = \|\vec{v}\| v_{norm,1}$ $$_1 v_z = {_1 z_1} c_1 + {_1 z_2} c_2 + {_1 z_3} c_3$$

$$_2 v_z = {_2 z_1} c_1 + {_2 z_2} c_2 + {_2 z_3} c_3$$

$$_3 v_z = {_3 z_1} c_1 + {_3 z_2} c_2 + {_3 z_3} c_3 \quad \text{(Eq. 9)}$$

With three equations and three unknowns this can be solved using the familiar 3×3 matrix inverse solution $$\begin{vmatrix} a_{11} a_{12} a_{13} \\ a_{21} a_{22} a_{23} \\ a_{31} a_{32} a_{33} \end{vmatrix}^{-1} = 1/\text{DET} *$$ (Eq. 10)

$$\begin{vmatrix} a_{33}a_{22} - a_{32}a_{23} & -(a_{33}a_{12} - a_{32}a_{13}) & a_{23}a_{12} - a_{22}a_{13} \\ -(a_{33}a_{21} - a_{31}a_{23}) & a_{33}a_{11} - a_{31}a_{13} & -(a_{23}a_{11} - a_{21}a_{13}) \\ a_{32}a_{21} - a_{31}a_{22} & -(a_{32}a_{11} - a_{31}a_{12}) & a_{22}a_{11} - a_{21}a_{12} \end{vmatrix}$$

with $\text{DET} = a_{11}(a_{33}a_{22} - a_{32}a_{23}) -$ (Eq. 11)
$a_{21}(a_{33}a_{12} - a_{32}a_{13}) + a_{31}(a_{23}a_{12} - a_{22}a_{13})$ Once the coefficients of Eq. 9 are solved, the magnitude of the blood flow velocity can be computed from the vector coefficients.

$$\|\vec{v}\| = \sqrt{c_1^2 + c_2^2 + c_3^2}$$ (Eq. 12)

This last result can be used to help verify that when the orientation with the predicted max velocity is moved to, that it is indeed achieved.

Pan and Tilt Angles: Analytic solution—If it is desired to describe the orientation of the blood flow in terms of pan and tilt angles, the pan and tilt angles can be derived from the z-axis of the X-Y-Z fixed angle rotation matrix $$^0_n R_{XYZ}(\gamma, \beta, \alpha) = \begin{bmatrix} \cdots & \cdots & c\alpha s\beta + s\alpha s\gamma \\ \cdots & \cdots & s\alpha s\beta c\gamma - c\alpha s\gamma \\ \cdots & \cdots & c\beta c\gamma \end{bmatrix}$$ (Eq. 13)

by setting the yaw angle, $\gamma$ to 0, and setting the coefficients $c_1, c_2, c_3$ equal to the third column of Eq. 13.

Numerical Solution: If more than three samples are used, a numerical solution can be found by extending the equations of (6) with the extra samples $_1v_z = _1z_1c_1 + _1z_2c_2 + _1z_3c_3$ $$_2v_z = _2z_1c_1 + _2z_2c_2 + _2z_3c_3$$ (Eq. 14)
$$_3v_z = _3z_1c_1 + _3z_2c_2 + _3z_3c_3$$
$$\cdots$$
$$_nv_z = _nz_1c_1 + _nz_2c_2 + _nz_3c_3$$

and then by using a generalized inverse to solve for the coefficients $c_1, c_2, c_3$ $$c = Z^\dagger V$$ (Eq. 15)

Dynamic Dwell Time: Some prior art two DOF systems dwell for a predefined period of time at each position where the system attempts to locate a signal. In some embodiments, employing a dynamic dwell time and a stability signal analysis can increase search speed significantly. In some embodiments, signal energy is computed after waiting at position for a predetermined wait period of time to eliminate signal/noise transients. In some embodiments, for each position, the predetermined wait period is computed dynamically based on a signal stabilization analysis. In some embodiments, it is preferable to use M-mode data for the signal analysis instead of pulsatile signal information, such as envelope and spectral information. Pulsatile signals are constantly changing and a mean signal analysis could require at least 1 second of data. M-mode data is more consistent versus time because it is less sensitive to depth, and other positional parameters.

Rather than spending 200-300 ms at each position, some embodiments may spend as little as 10 ms at a location when it is determined through a dynamic dwell time analysis that no usable signal is present. In some embodiments, only a minimal amount of time is needed to be spent at a location if the M-mode signal is near zero. In some embodiments, spending a minimal amount of time at a location significantly speeds up the searching process because many positional data acquisitions only acquire noise level data.

E. Vascular Mapping

Vascular mapping may follow the signal to be optimized at several points within the Circle of Willis. Therefore, the mapping feature may be performed in connection with the following features: Automatic Transducer Placement, Automatic TCD Window Discovery, and Signal Optimization.

Figure 22:
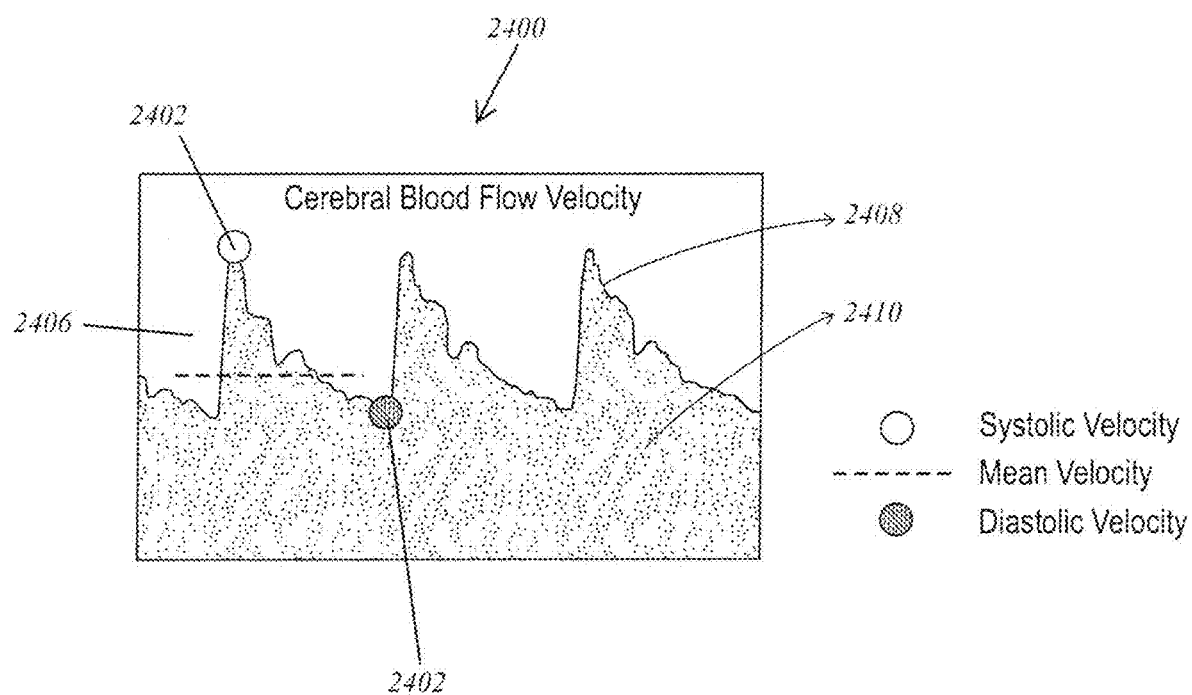
FIG. 22 illustrates a CBFV spectrum.

Overview: Traditionally, transcranial Doppler (TCD) ultrasound has been used for the assessment of cerebral blood flow velocity (CBFV) at a discrete point (depth) within the Circle of Willis with limited additional information. Some embodiments provide a method to combine discrete points into a "map" of the cerebral vasculature using an automated 6 DOF mechanism combined with an analytic approach for combining the ultrasound data. This rendering of the dynamics of the vasculature provides clinicians a more complete view of the vasculature allowing for better diagnosis, triage, and monitoring of a number of neurologic conditions including stroke (hemorrhagic or ischemic), traumatic brain injury, migraine, dementia, and others. Some embodiments include several subsections including vessel identification, robotic kinematics, use of anatomical context, and influence of bilateral monitoring FIGS. 22-24 correspond to features of Vascular Mapping. The simplest form of TCD is a single-gate pulsed Doppler ultrasound. In this setting, velocity information is obtained from a single depth, as shown in FIG. 22. FIG. 22 illustrates a CBFV spectrum 2400. For each CBFV pulse traditional TCD calculated the systolic velocity 2402, diastolic velocity 2404, and mean velocity 2406. Additionally, there is a velocity envelope 2408 (peak velocity throughout the cardiac cycle), and the velocity spectrum 2410. Additionally, multiple gates (depths) can be insonated allowing for the collection of different velocity spectrum at different depths within the cerebral vasculature.

Figure 23A:
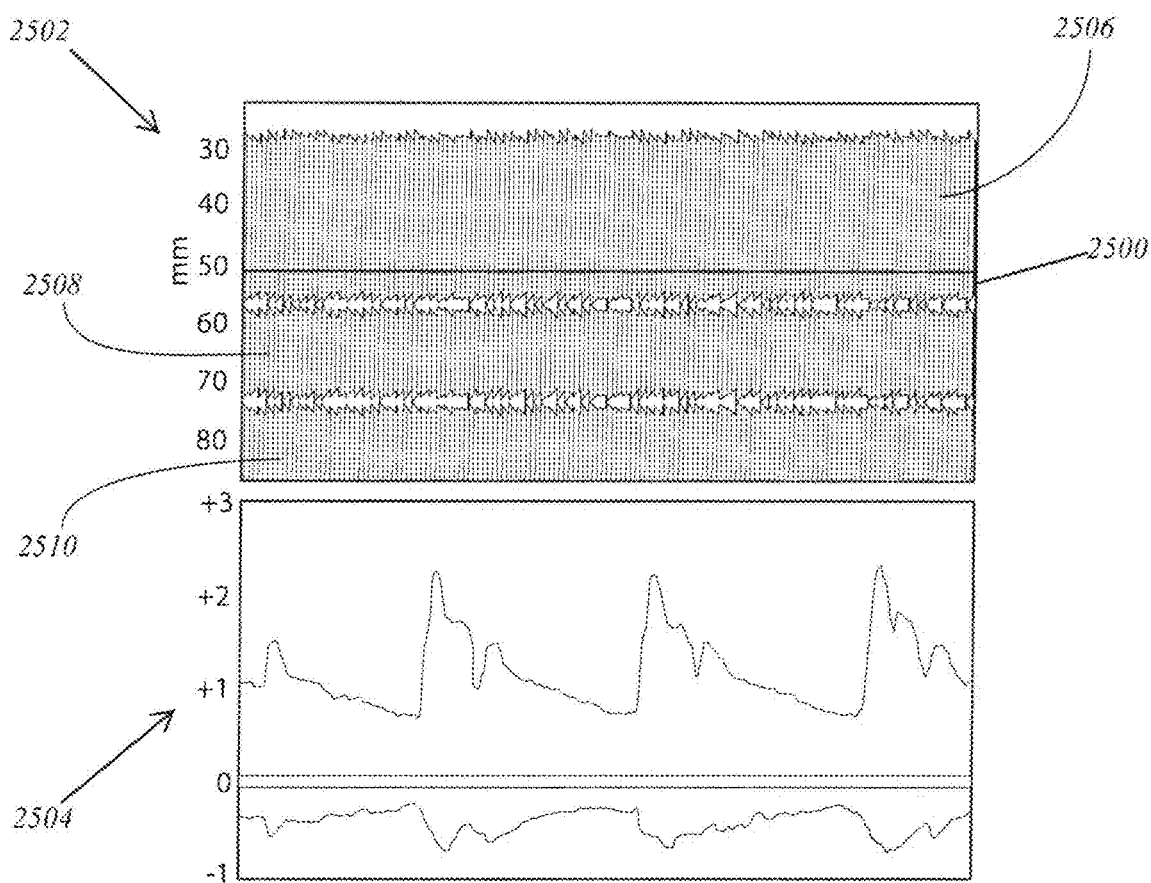
FIG. 23A illustrates a power M-mode Doppler display.

A relatively recent development known as power M-mode Doppler samples the power at a large number of depths providing power and direction information, as shown in FIG. 23A. The spectral display of FIG. 23A is calculated based on the depth represented by line 2500 in FIG. 23A. Although multi-gate and M-mode allow for a more complete "image" of the vasculature, limitations in information extraction/integration, user variability, and single transducer monitoring prevent a usable vascular map.

Information Extraction/Integration: Despite reporting of the overall velocity spectrum shown in FIG. 24, in some existing systems, this information is not utilized to assess optimal signal within a given vessel. Signal optimization is essential for accurate identification and visualization of the cerebral vasculature. M-Mode is an ultrasound presentation of temporal changes in echoes in which the depth of echo-producing interfaces is displayed along one axis with time (T) along the second axis; motion (M) of the interfaces toward and away from the transducer is displayed. M-Mode representations are based on power and mean velocity at a specific depth, and therefore disregard the velocity spectrum. Integration of the velocity spectrum is described below.

Manipulation of TCD Parameters: In some embodiments, various TCD parameters can be manipulated, including signal gain, pulse repetition frequency (PRF), the sample volume or length, and filtering the TCD signal to reduce noise.

In some embodiments, the depth of the sample volume is also manipulated. Specifically, a sample may be dynamically selected at specified intervals, and in some embodiments the specified intervals may range from 0.01 s to 1 s. In some embodiments, the depth of the sample volume may be guessed and checked for a given search position. For example, in some embodiments, such as a search for the MCA, the depth may be checked at approximately 45 mm to 65 mm.

In some embodiments, the depth can be automatically computed. For example, in some embodiments the appropriate depth may be calculated by determining the maximum power at a depth as provided by M-mode information.

User Variability: Despite the several measurement methods described above, traditional TCD suffers from significant user variability. Manual or semi-automated (Two DOF) systems do not provide a reliable signal and therefore are inadequate for complete insonation of the Circle of Willis.

Anatomical Feature Walking: Limitations of current manual TCD technology and user variability make it impossible or nearly impossible to construct a map of the path of a blood vessel. In some embodiments, using the robotic techniques described herein, including information concerning TCD signal strength, depth, and position, the robotic system can follow the path a blood vessel takes walking through the path at various depths within the body of a subject.

Signal Classification Based On Waveform Analysis: Identification of a particular vessel can be achieved by comparing the depth, velocity, angle, and/or waveform morphology with those from a sample population or within the individual's currently or previously collected waveform information.

In one embodiment, the waveform of an individual is compared to a dictionary of labeled waveforms contained in a validated dictionary. The comparison can be done using a standard distance metric such as the L2-norm or the correlation distance. A subspace decomposition in a supervised, unsupervised, or semi-supervised way can also be used alone or in conjunction with other distance methods.

In another embodiment, the waveform of the MCA captured below 50 mm is recorded initially. Using the depth and velocity information the identity of the MCA can be assumed. This waveform is used as the anchor vessel. Other vessels can then be insonated and recorded. The identity of these subsequent vessels can be determined using their physical location relevant to the anchor vessel. Ensuring their identity relative to each other can be accomplished by a complete pairwise distance comparison. Additionally, a subspace decomposition of the collected waveforms can be used to ensure adequate separation of the projected waveforms. This decomposition can be done after the collection of each vessel or after all of them have been collected.

Bilateral Monitoring: Although some prior TCD systems provided bilateral-monitoring capabilities, those systems are independent of one another. In some embodiments, integration of the two probes provides verification of optimal velocity and decreased calculation duration.

Figure 23B:
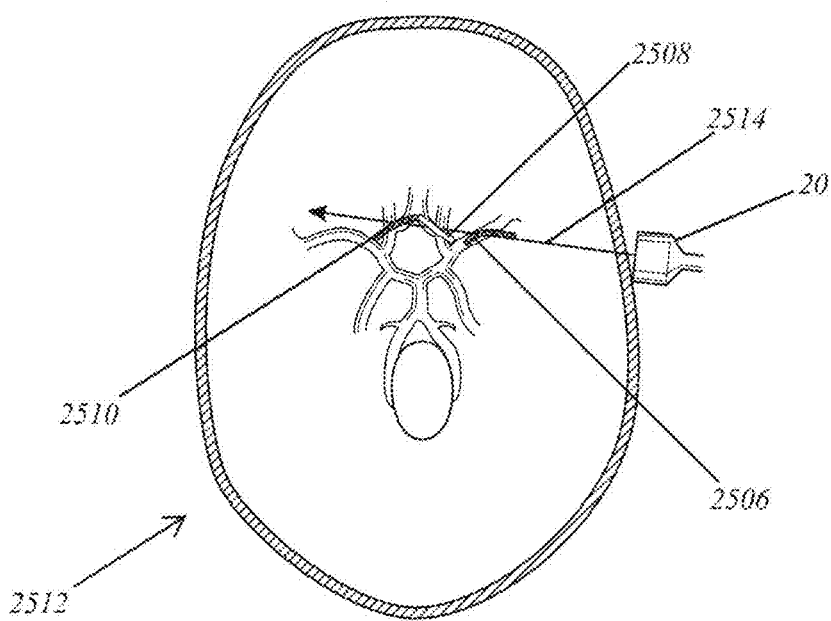
FIG. 23B illustrates a schematic of anatomy of arteries in the brain.

FIG. 23A: Example of power M-mode. The power M-mode Doppler image 2502 in FIG. 23A resides above the spectrogram image 2504 of FIG. 23A, so that they share the same horizontal time axis. The power M-mode Doppler image 2502 shows depth from the transducer on the vertical axis, time on the horizontal axis, and power of the Doppler shift signal at specific depths as intensity. Simultaneously, the direction of blood flow is derived from the positive or negative mean value of the Doppler shift signal at the particular depth. As each new line in the spectrogram is calculated and displayed, a corresponding power M-mode Doppler image line is displayed concurrently in the PMD image directly above. The horizontal line 2500 in the PMD display in FIG. 23A indicates the gate depth associated with the spectrogram in FIG. 23A. Also shown in FIG. 23A is demonstration of beam alignment with the right middle cerebral artery 2506, right anterior cerebral artery 2508, and the left anterior cerebral artery 2510. A schematic of the anatomy 2512 from which the PMD image is derived is drawn in FIG. 23B, showing right middle cerebral artery 2506, right anterior cerebral artery 2508, and the left anterior cerebral artery 2510 using a transducer 20, and ultrasound beam axis 2514.

Figure 24:
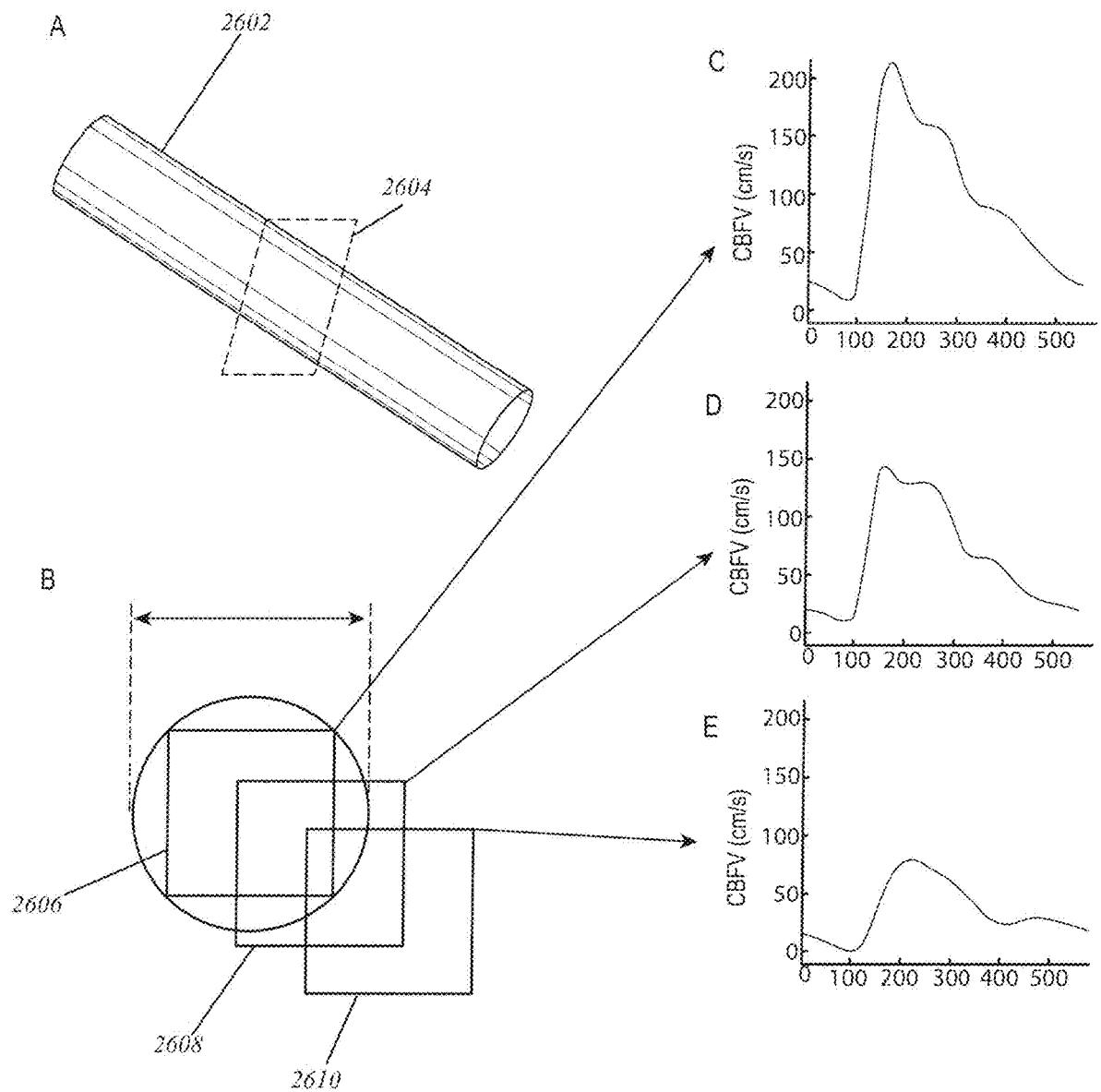
FIG. 24 illustrates CBFV samples for a blood vessel.

Cerebral Blood Flow Velocity: As shown in FIG. 24, a major conducting vessel 2602 of the Circle of Willis is commonly the Middle Cerebral Artery (MCA); however, it can represent any vessel. A cross section 2604 of an artery, with three projected samples volumes (TCD) 2606, 2608, 2610 is shown in FIG. 24. Optimal sample volume 2610, captures the true peak CBFV. Intermediate velocity 2608 and, CBFV is lower because of partial voluming. Work sample volume 2610 placement is also shown.

5 or 6 DOF Mechanism—Information Extraction/Integration: Some embodiments address the limitation of signal optimization through integration of fundamental elements of TCD. Manual insonation of the optimal CBFV signal requires integration of several elements including transducer orientation, spectrum recognition, vessel identification, and depth. These elements are developed through experience and unfortunately lead to variability between users.

Orientation of the Transducer: Over time, an expert user gains the ability to visualize the Circle of Willis structure. The orientation of the transducer in X-Y and Θ-Φ space is not used. Combined with the depth information embodiments can identify and record a sample volume in 3D space. Orientation and depth allows for more accurate vessel identification and mapping. When combined with bilateral monitoring some embodiments introduce a level of verification as well.

Spectral Information: As described, traditional analysis of CBFV is limited to the most prominent features, systolic, diastolic, mean velocities, and Pulsatility Index, as shown in FIG. 24. This analysis has been clinical practice for over 30 years and current machines are unable to capture the full potential of the signal. In such analysis, important information about the pulsatile CBFV waveform is lost.

By using a 5 DOF mechanism and a redundant depth DOF from the TCD (virtual six DOF kinematics), some embodiments manage position and orientation of the sample volume to maximize signal. By following maximized signal along normal flow velocity direction, some embodiments track along vascular structure—not grid scanning of entire head. This approach is useful in signal acquisition and total vascular mapping.

Using multidepth information the software communicates with the hardware on where to go next. Understanding where the current location is and where to go next greatly simplifies the problem of mapping the MCA, ACA, PCAs. The advantage of approach is that it identifies asymmetries automatically in not only flow velocity but waveform morphology.

F. Transducer Force Controller

One component often overlooked is the force required to maintain sufficient pressure of the transducer to the skin of the subject. When the transducer is at an extreme angle insufficient pressure will allow the transducer to slip, causing the loss of signal.

Some embodiments optimize TCD signal strength with a force sensing robot. Normal force to the head is achieved in current mechanisms in an uncontrolled fashion, such as being manually screwed in. By using a force sensor (or motor torque sensing) some embodiments automatically adjust TCD pressure to maximized signal strength. By sensing moments (torques) about the transducer, the surface normal orientation can be deduced. The condition for normal orientation is to minimize the moments about the transducer.

Curved Surface Following: Maintaining Transducer Orientation with Constant Force: In order to generalize an automated TCD system from two dimensional surfaces to contoured heads, some embodiments provide mechanical and robotic controls to align the transducer normal to the surface while applying constant force. This work occurs in parallel with the TCD search and signal processing algorithm.

G. Kinematics

According to various embodiments, a five actuated degree of freedom (DOF) kinematic mechanism is used that fully automates evaluation of the temporal window quality and can rediscover the temporal window even after complete loss of signal. To those skilled in the art, a distinction exists between an active, or actuated degree of freedom, on the one hand, and a passive degree of freedom on the other hand. An active, or actuated degree of freedom includes an actuator, such as for example, a motor. A passive degree of freedom does not require such an actuator. In this specification, if the term "degree of freedom" is used without being qualified as passive, the degree of freedom discussed is meant to be an active or actuated degree of freedom. In some embodiments, a computer generates commands and directs the mechanism to translate and reorient the probe along the surface of the head until a candidate signal is located. Once located, the probe is reoriented to increase signal strength. In some embodiments, reducing the search time of the automated system to discover the temporal window is accomplished by aligning the mechanism and probe at a known anatomical feature, such as the zygomatic arch. In some embodiments, the alignment is performed with a visual window guide for the user to place the probe at an initial starting point along the zygomatic arch between ear and the eye.

In some embodiments, after the probe is properly aligned, the stiffness of the probe is held normal to the surface at a high enough level to keep the probe seated, but low enough so to be comfortable to the user as the probe moves in and out following the surface of the head. In some embodiments, the X and Y axes can retain a higher servo stiffness in order to maintain precision control of probe location. In some embodiments, because the normal force of the probe is determined by the Z-axis stiffness, the sliding force encounter by the X and Y axes will be limited to a comfortable level, and the probe can be directed to perform a search for the TCD window. In some embodiments, if the orientation of the probe needs to be changed, the orientation stiffnesses can be increased via software.

In some embodiments, the kinematic mechanism of the probe includes five motor, or actuated, degrees of freedom, Q={J1, J2, J3, J4, J5} (i.e., motor or joint space) to effect five degrees of freedom in position and orientation X={x, y, z, pan, tilt} (i.e., task space). As such, the forward kinematics may be written as the relationship between motor coordinates and probe coordinates: X=fwd_kin(Q), where fwd_kin is a function representing a series of equations based on the mechanism design and typically analyzed by Denavit-Hartenberg parameters.

In some embodiments, placement of the TCD probe is specified via the inverse kinematics with either an analytic inverse solution: Q=inv_kin(X), or by using a numerical differential such as the Jacobian inverse solution $dQ_{cmd}(n) = J^{-1}(X_{err}(n))$, where J is the Jacobian, relating differential motion of the motors to the differential motion of the probe, $X_{err}(n)$ is the probe position and orientation error at time n, and $dQ_{cmd}(n)$ is the differential motor command at time n. For mechanisms with more motor or actuated degrees of freedom than probe position and orientation coordinates being controlled, the kinematics are called redundant, and such mechanisms have more than five motors. For redundant mechanisms, the inverse kinematics changes from the inverse Jacobian to the Moore-Penrose pseudo-inverse (or other generalized inverse) of the Jacobian, $dQ_{cmd}(n) = J^{\dagger}(X_{err}(n))$.

Figure 25:
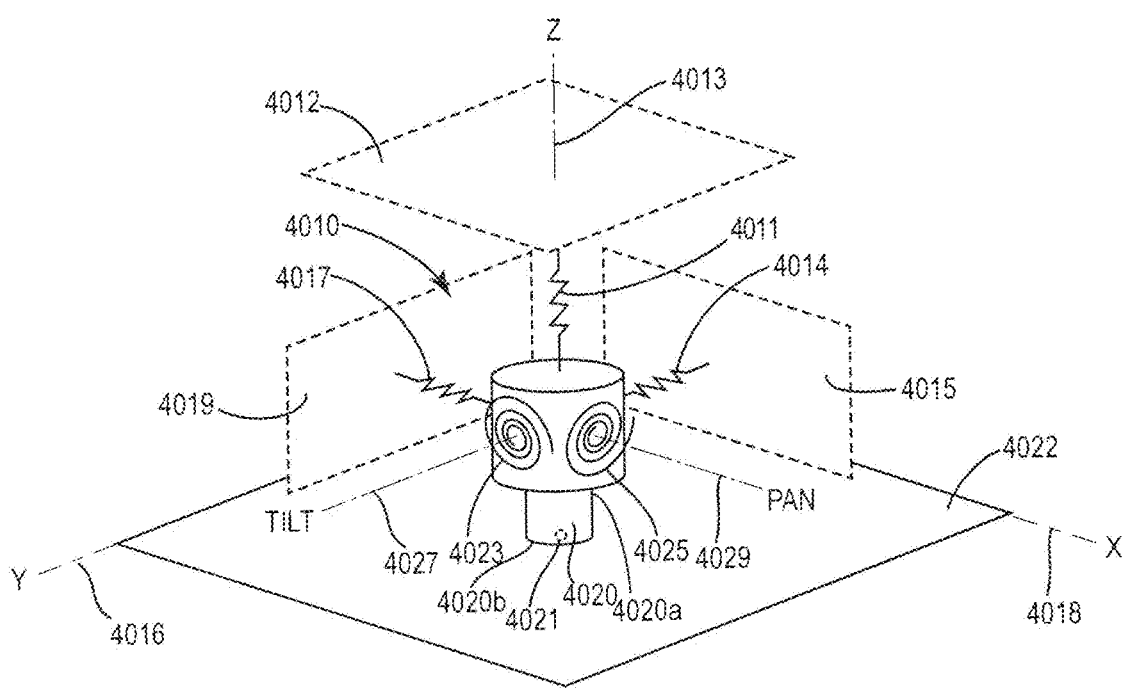
FIG. 25 is a diagram of a virtual support structure for manipulating a medical probe, according to an exemplary embodiment.

FIG. 25 is a diagram of a model of a virtual support structure 4010 for a probe 4020, according to an exemplary embodiment. When probe 4020 is discussed, a transducer could be used instead. The support structure 4010 is configured to position the probe 4020 relative to a target surface 4022. In some embodiments, the probe 4020 is a medical probe, such as a medical probe for use with a transcranial Doppler (TCD) apparatus to emit ultrasound wave emissions directed to the target surface 4022. In other embodiments, the probe 4020 is configured to emit other types of waves during operation, such as, but not limited to, infrared waves, x-rays, and so on. In various embodiments, the probe 4020 may be a transcranial color-coded sonography (TCCS) probe, or it may be an array such as a sequential array or phased array which emits waves.

In some embodiments, the probe 4020 has a first end 4020a and a second end 4020b. In some embodiments, the first end 4020a interfaces with the support structure 4010. In some embodiments, the second end 4020b contacts the target surface 4022 on which the probe 4020 operates at a contact point 4021. In some embodiments, the second end 4020b is a concave structure such that the contact point 4021 is a ring shape (i.e., the second end 4020b contacts the target surface 4022 along a circular outer edge of the concave second end 4020b). The support structure 4010 controls the relative position of the probe 4020 (e.g., z-axis force, y-axis force, x-axis force, normal alignment, etc.). The support structure 4010 is shown as a virtual structure including a first virtual spring 4011 coupled between the probe 4020 and a virtual surface 4012 and exerting a force along a z-axis 4013, a second virtual spring 4014 coupled between the probe 4020 and a virtual surface 4015 and exerting a force along a y-axis 4016, and a third virtual spring 4017 coupled between the probe 4020 and a virtual surface 4019 and exerting a force along the x-axis 4018. The virtual support structure 4010 further includes a torsional spring 4023 exerting a torque about a tilt axis 4027 and a second torsional spring 4025 exerting a torque about a pan axis 4029. In some embodiments, the virtual support structure 4010 includes other virtual elements, such as virtual dampers (not shown). Virtual dampers represent elements that improve the stability of the system and are useful for tuning the dynamic response of the system. The virtual, or apparent inertia of the probe, can also be set to have isotropic or anisotropic properties, by modeling and feed forwarding out the effects of mechanism inertia, motor rotational inertial, centripetal/centrifugal effects, and replacing them with arbitrary inertial properties, within the physical performance limits of the device.

The virtual support structure 4010 represents a variety of mechanical structures that may be utilized to position the probe 4020 relative to the target surface 4022, as described in more detail below. In some embodiments, the second end 4020b of the probe 4020 is caused to contact a relatively delicate surface, such as the skin of the patient or subject. The support structure is configured to adjust its stiffness (e.g., impedance, compliance, etc.) to provide variable linear forces and rotational forces on the probe 4020, and may be relatively stiff in some directions and may be relatively compliant in other directions. For example, the support structure 4010 may apply minimal force and may be relatively compliant along the z-axis 4013 to minimize forces applied to the patient or subject (e.g., if the patient or subject moves relative to the support structure) in a direction generally normal to the target surface 4022 and may be relatively stiff along the y-axis 4016 and the x-axis 4018 to improve the positional accuracy and precision of the probe 4020 along a plane generally parallel to the target surface 4022. Further, the desired stiffness of the support structure 4010 along various axes may vary over time, depending on the task at hand. For example, the support structure may be configured to be relatively compliant in scenarios in which the support structure 4010 is being moved relative to the patient or subject (e.g., during initial set-up of the probe structure, removal of the probe structure, etc.), or when it is advantageous to be relatively free-moving (e.g., during maintenance/cleaning, etc.), and may be configured to be relatively stiff, in some directions, in scenarios in which accuracy and precision of the positioning of the probe 4020 is advantageous (e.g., during the TCD procedure or other procedure being performed with the probe 4020).

As described in more detail below, a kinematic model of the support structure 4010 can be utilized to calculate the relationship between the forces applied to the target surface 4022 by the probe 4020 and the forces (e.g., torques) applied by actuators actuating the support structure 4010. The forces applied to the target surface 4022 by the probe 4020 in the idealized system can therefore be determined theoretically, without direct force sensing, thereby eliminating the need for a load cell disposed in-line with the probe 4020 and/or a force torque sensor coupled to the probe 4020 to maintain appropriate contact force that maximizes signal quality. In a physical system, static friction, along with other unmodeled physical effects, may introduce some uncertainty.

Figure 26:
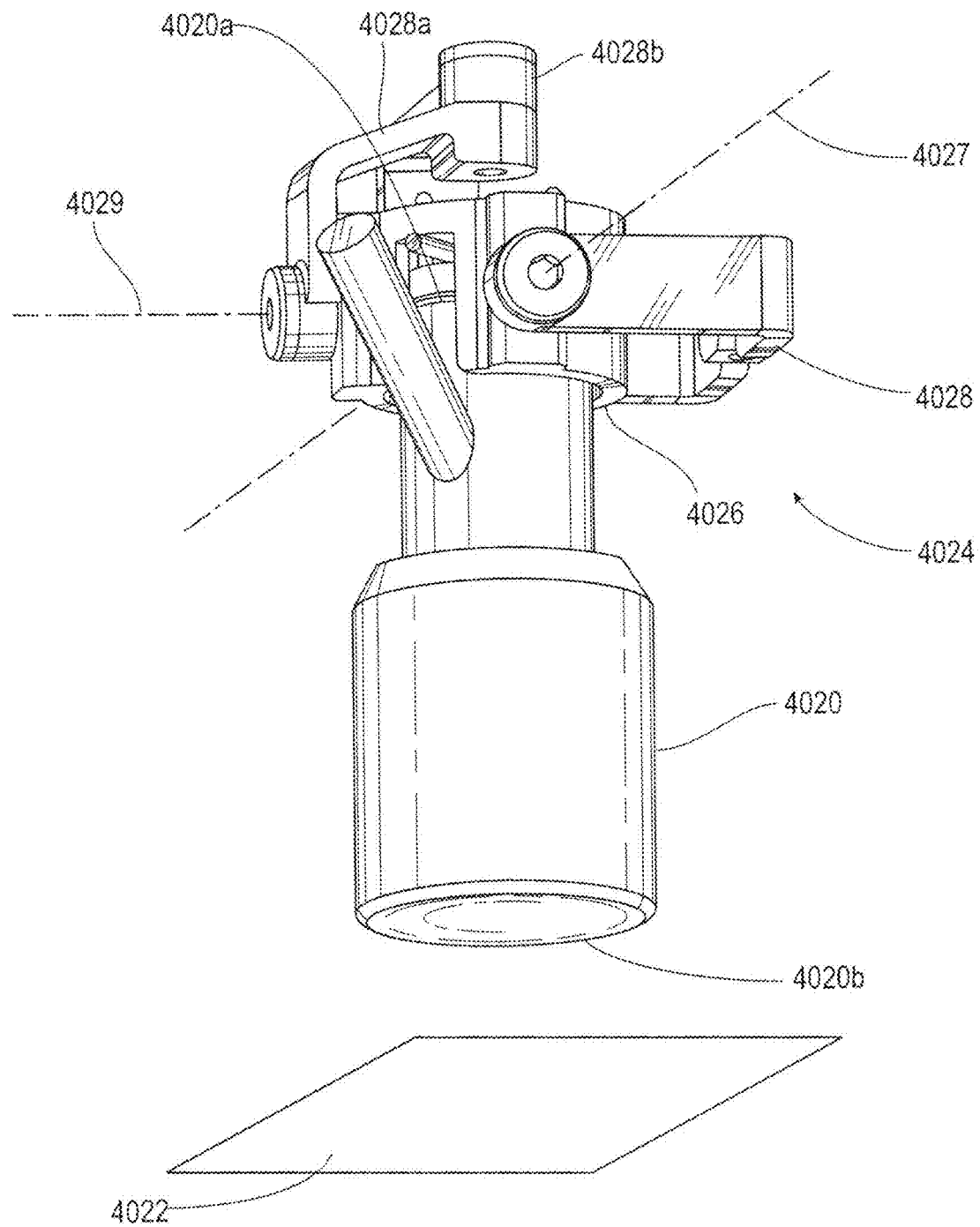
FIG. 26 is an perspective view of a medical probe and a gimbal structure, according to an exemplary embodiment.

Referring to FIG. 26, the probe 4020 is shown according to an exemplary embodiment mounted to a portion of a support structure, shown as a gimbal structure 4024, which can rotate about multiple axes, at the first end 4020a. The gimbal structure 4024 includes a first frame member 4026 that is able to rotate about the tilt axis 4027 and a second frame member 4028 that is able to rotate about the pan axis 4029. The target surface 4022 may be uneven (e.g., non-planar). The gimbal structure 4024 allows the probe 4020 to be oriented such that it is normal to the target surface 4022 at the contact point 4021.

Figure 27:
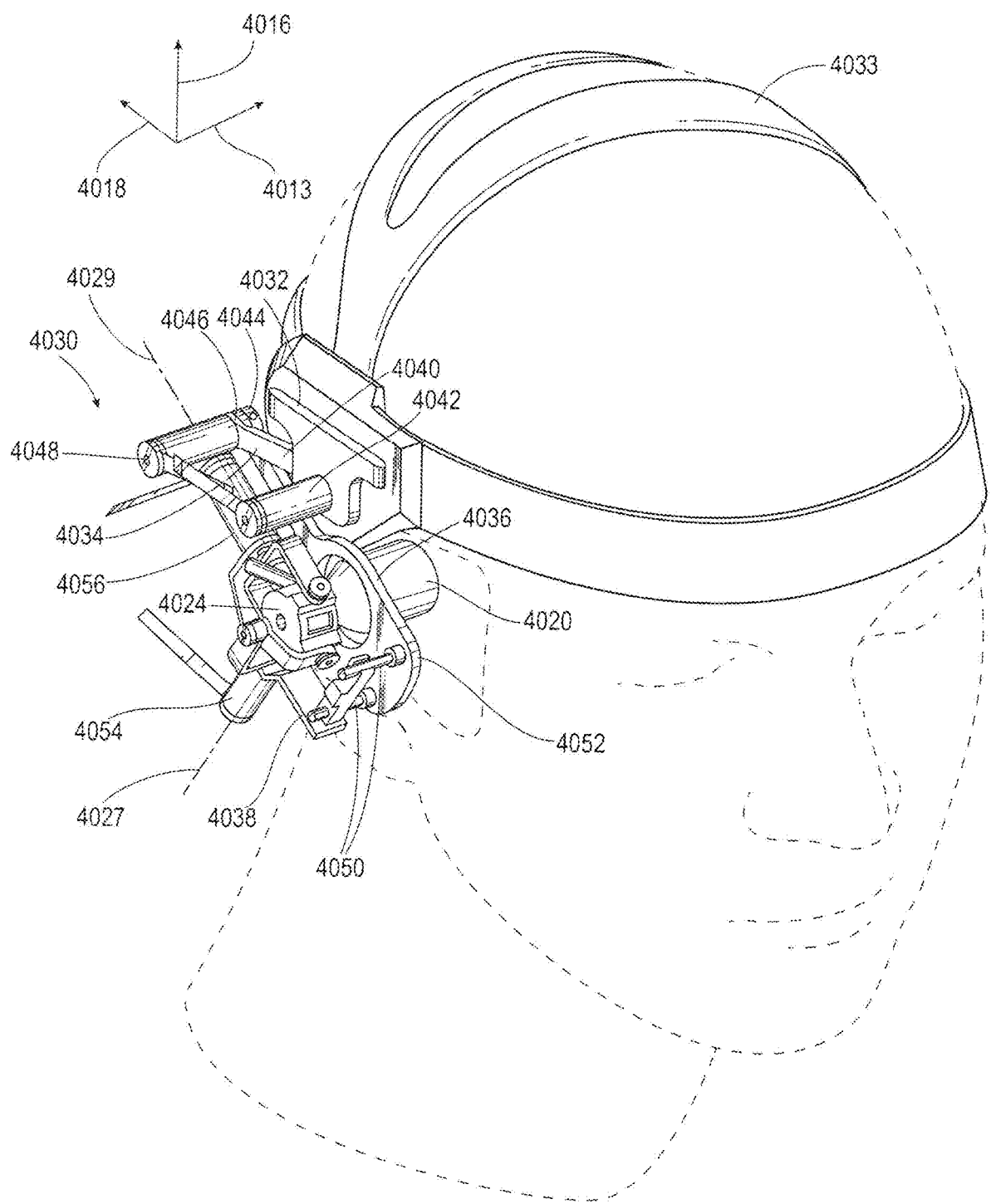
FIG. 27 is a perspective view of a two-link revolute support structure for the medical probe of FIG. 26, according to an exemplary embodiment.
Figure 28:
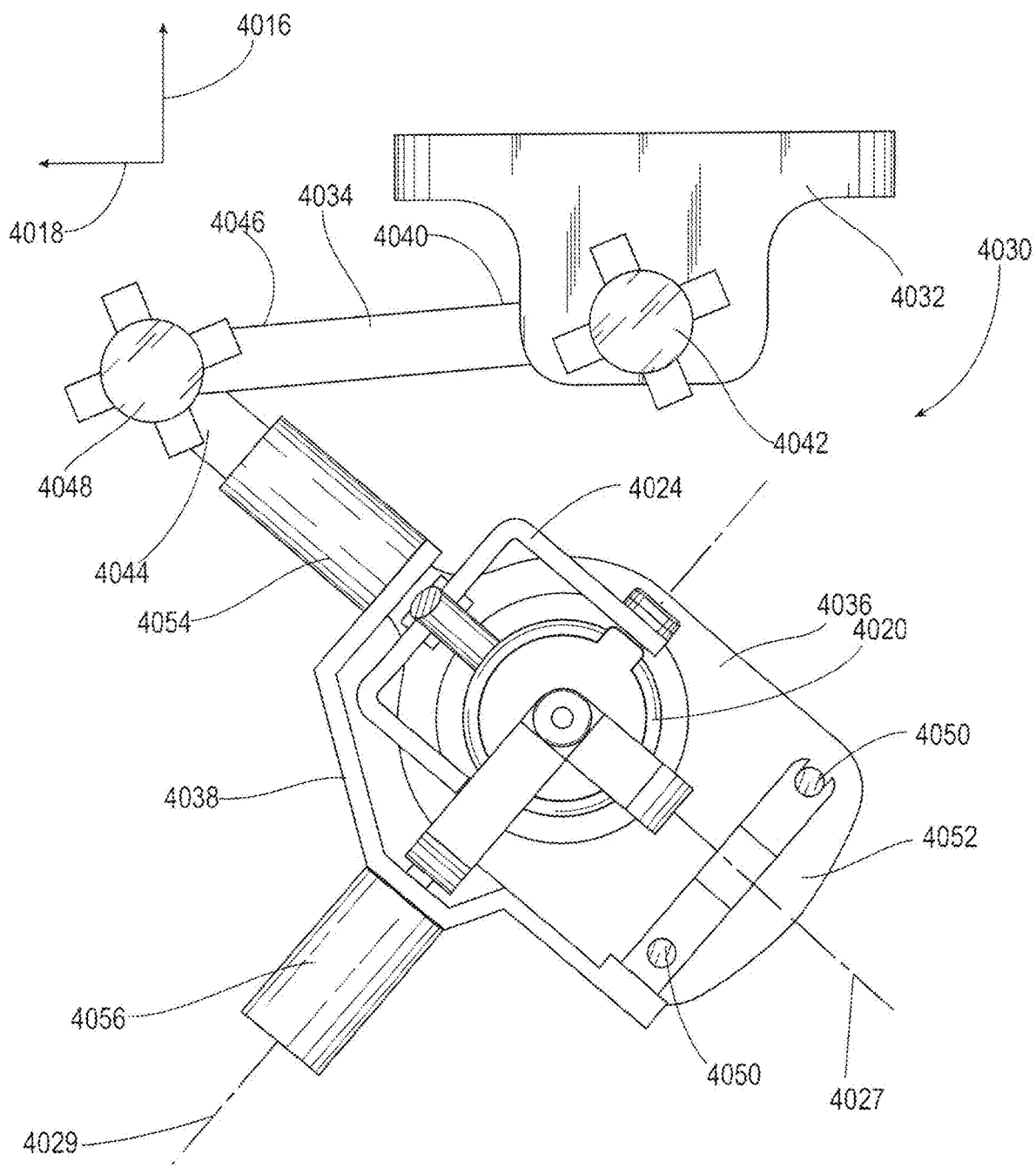
FIG. 28 is front elevation view of the support structure of FIG. 27.
Figure 29:
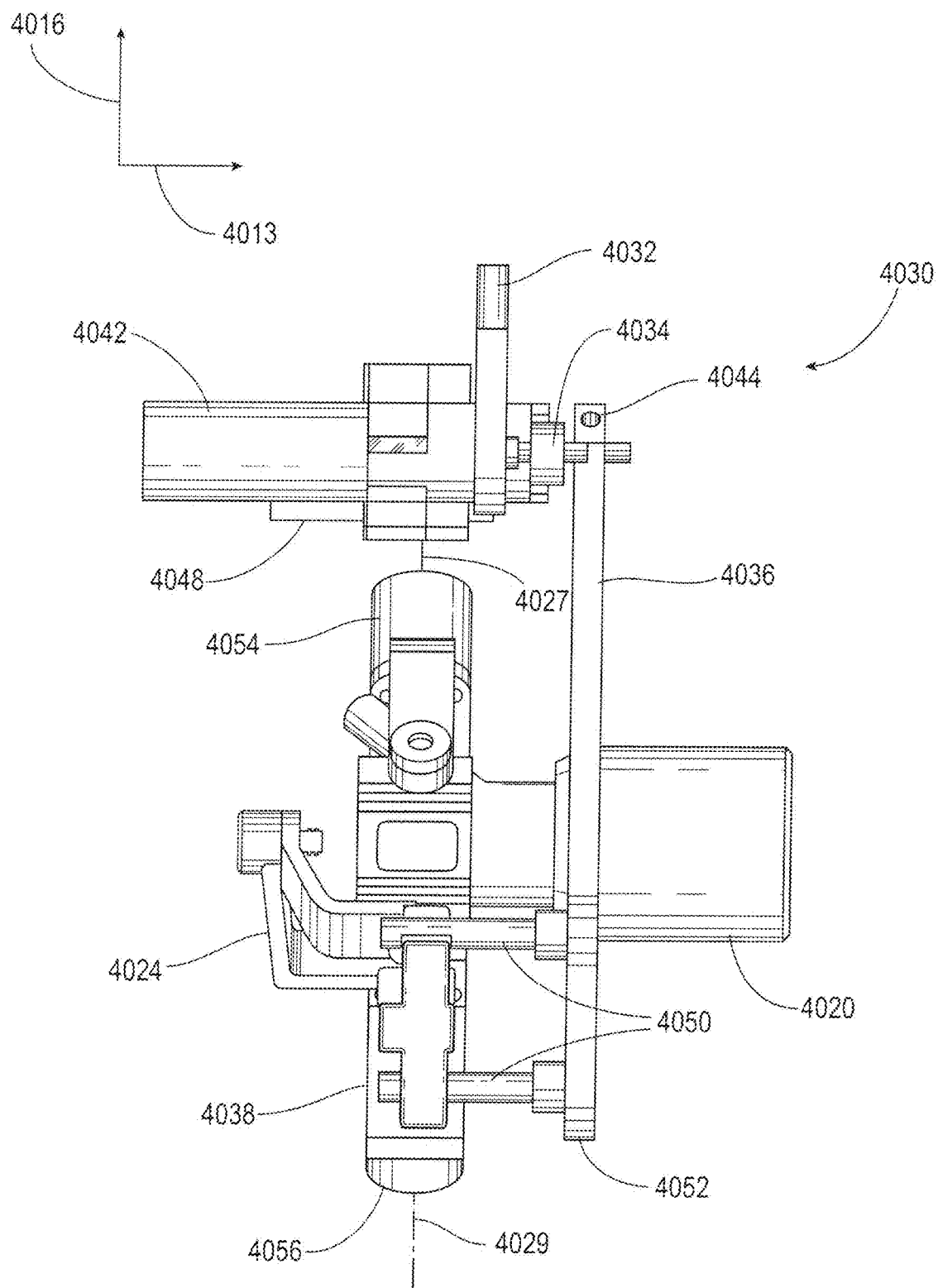
FIG. 29 is a right side elevation view of the support structure of FIG. 27.

Referring now to FIG. 27, FIG. 28, and FIG. 29, a support structure 4030 for the probe 4020 is shown according to an exemplary embodiment as a two-link revolute (e.g., revolute-revolute) robot. The support structure 4030 includes a first frame member 4032, a second frame member 4034, a third frame member 4036, a fourth frame member 4038, and the gimbal structure 4024. The first frame member 4032 is configured to be a static member. The first frame member 4032 may, for example, be mounted to a halo or headset 4033 worn on the patient's or subject's head or other structure that attaches the first frame member 4032 to the patient or subject or fixes the position of the first frame member 4032 relative to the patient or subject. The probe 4020 is configured to emit energy into the head of the patient or subject.

Referring to FIG. 27, the second frame member 4034 is a link configured to rotate about the z-axis 4013. The z-axis 4013 is generally perpendicular to the surface of the head. A first end 4040 of the second frame member 4034 is coupled to the first frame member 4032. According to an exemplary embodiment, the rotation of the second frame member 4034 relative to the first frame member 4032 is controlled by an actuator 4042, shown as an electric motor and gearbox that is attached through the first frame member 4032. Actuator 4042 acts as a perpendicular translation actuator for translating the probe along a perpendicular axis generally perpendicular to the surface of the head.

The third frame member 4036 is a link configured to rotate about the z-axis 4013. A first end 4044 of the third frame member 4036 is coupled to a second end 4046 of the second frame member 4034. According to an exemplary embodiment, the rotation of the third frame member 4036 relative to the second frame member 4034 is controlled by an actuator 4048, shown as an electric motor and gearbox that is attached through the second frame member 4034.

The fourth frame member 4038 is configured to translate along the z-axis 4013 (e.g., in and out, in and away from the head, etc.). According to an exemplary embodiment, the fourth frame member 4038 slides along rail members 4050 that are fixed to a second end 4052 of the third frame member 4036. The position of the fourth frame member 38 relative to the third frame member 4036 is controlled by an actuator, such as an electric motor and a lead screw (not shown for clarity).

The gimbal structure 4024 and the probe 4020 are mounted to the fourth frame member 4038. The gimbal structure 4024 controls the orientation of the probe 4020 about the tilt axis 4027 and the pan axis 4029 (e.g., pan and tilt). The position of the probe 4020 about the tilt axis 4027 is controlled by an actuator 4054, shown as an electric motor and gearbox. Actuator 4054 acts as a rotation actuator to rotate the probe. The position of the probe 4020 about the pan axis 4029 is controlled by an actuator 4056, shown as an electric motor and gearbox. Actuator 4056 acts as a rotation actuator to rotate the probe. In one embodiment, the rotation of the probe 4020 about the tilt axis 4027 and the pan axis 4029 is different than the z-axis 4013, regardless of the rotation of the frame members 4034 and 4036.

The probe 4020 is able to move on the x-y plane, i.e., the translation plane, which is defined by the x-axis 4018 and the y-axis 4016, through the rotation of the second frame member 4034 and the third frame member 4036. The probe 4020 is able to move along the z-axis 4013, i.e., the translation axis, through the translation of the fourth frame member 4038. Further, the probe 4020 is able to rotate about tilt axis 4027 and the pan axis 4029 through the gimbal structure 4024. Combining these five actuated degrees of freedom allows the position and orientation of the probe 4020 relative to the target surface 4022 to be completely described and controlled, discounting rotation about a third axis that is orthogonal to the pan axis 4029 and the tilt axis 4027.

According to an exemplary embodiment, the actuators utilized to position the support structure 4030 are servo motors. The use of servo motors to control the support structure allow for a more precise control, compared to a stepper motor, for the torque output, rotational position, and angular speed of the motor, as well as the corresponding position of the probe 4020 and the interaction between the probe 4020 and the target surface 4022. Of course, other suitable motors known to those of ordinary skill in the art could also be used.

Figure 30:
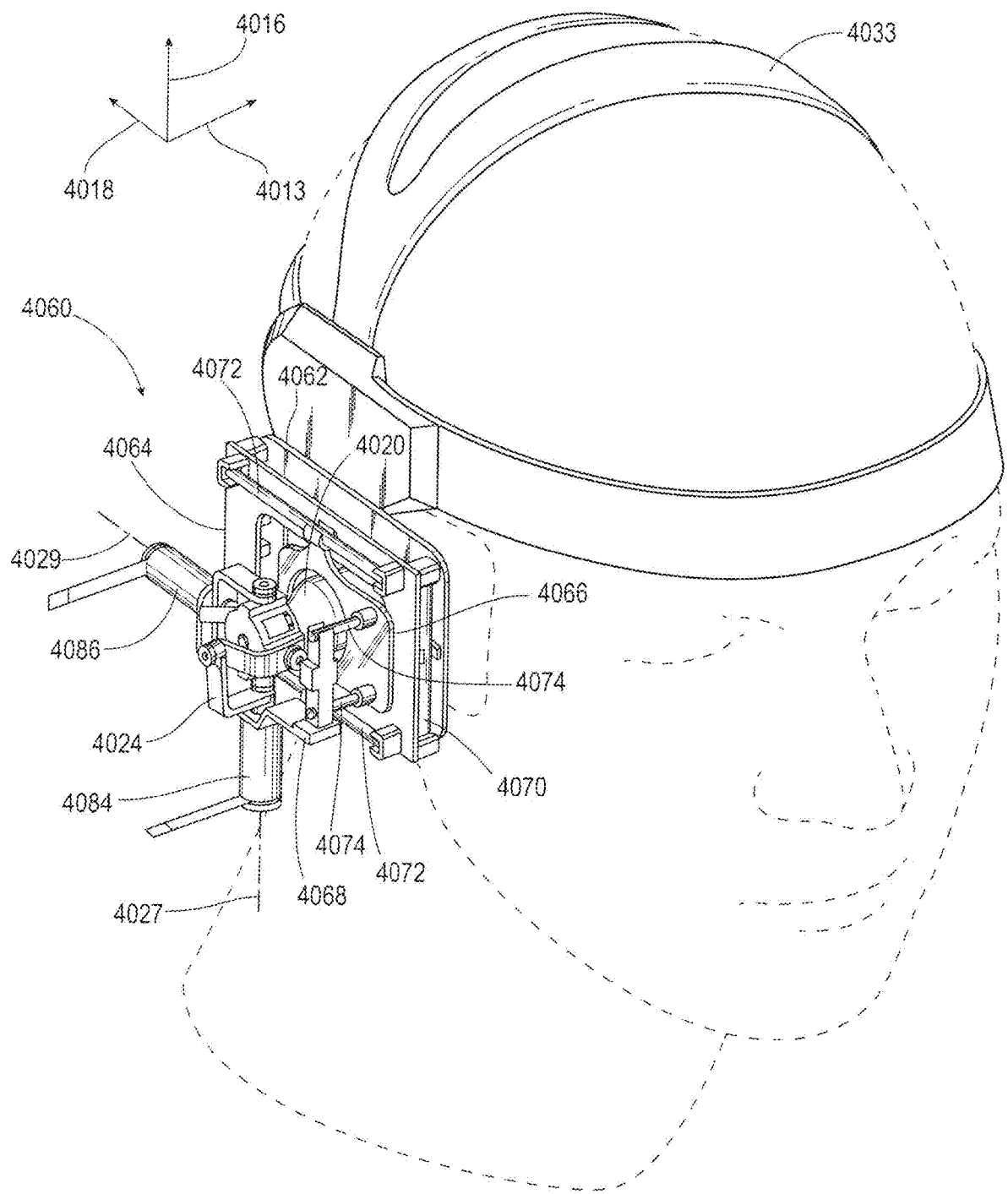
FIG. 30 is a perspective view of a prismatic support structure for the medical probe of FIG. 26, according to an exemplary embodiment.
Figure 31:
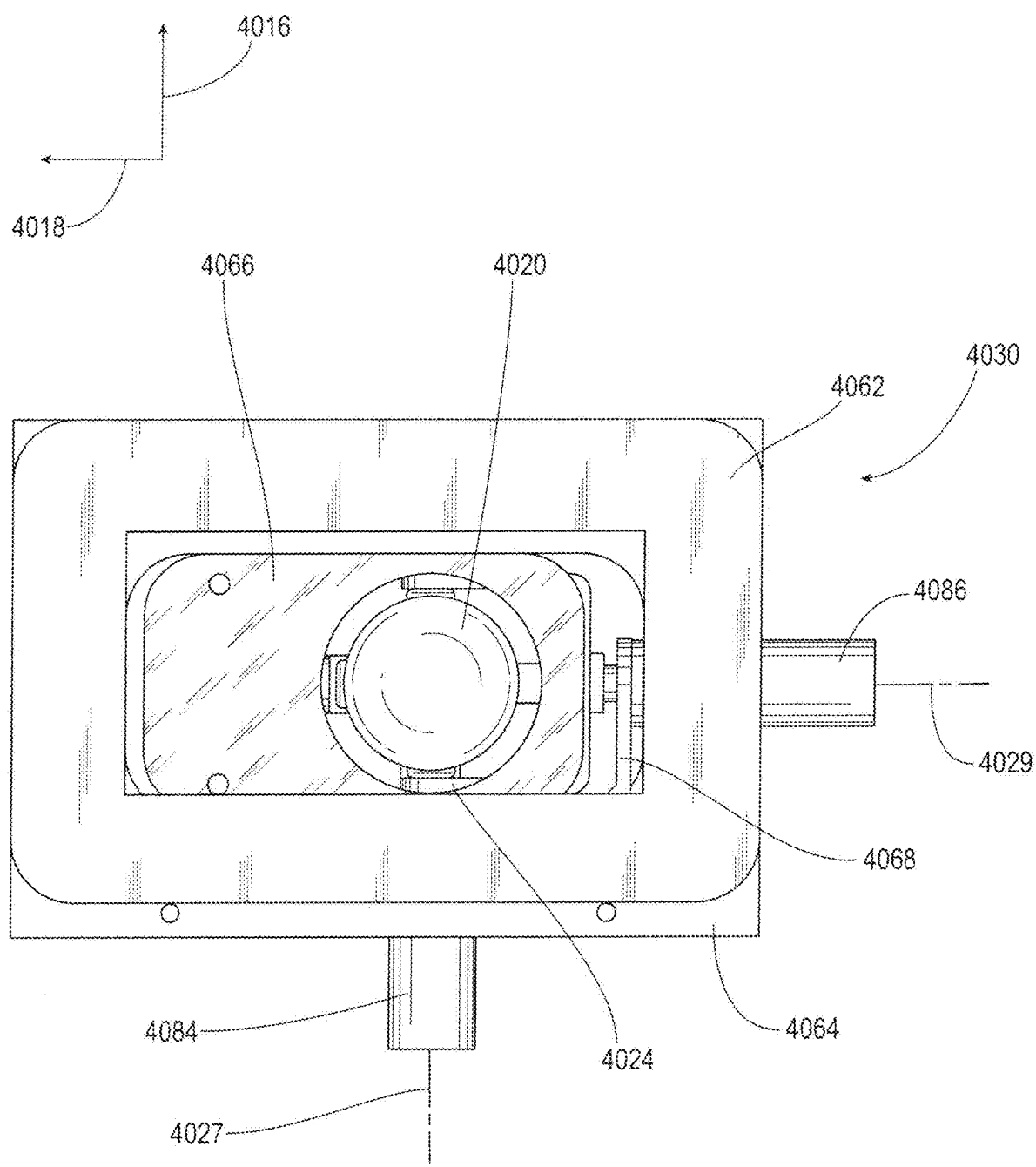
FIG. 31 is front elevation view of the support structure of FIG. 30.
Figure 32:
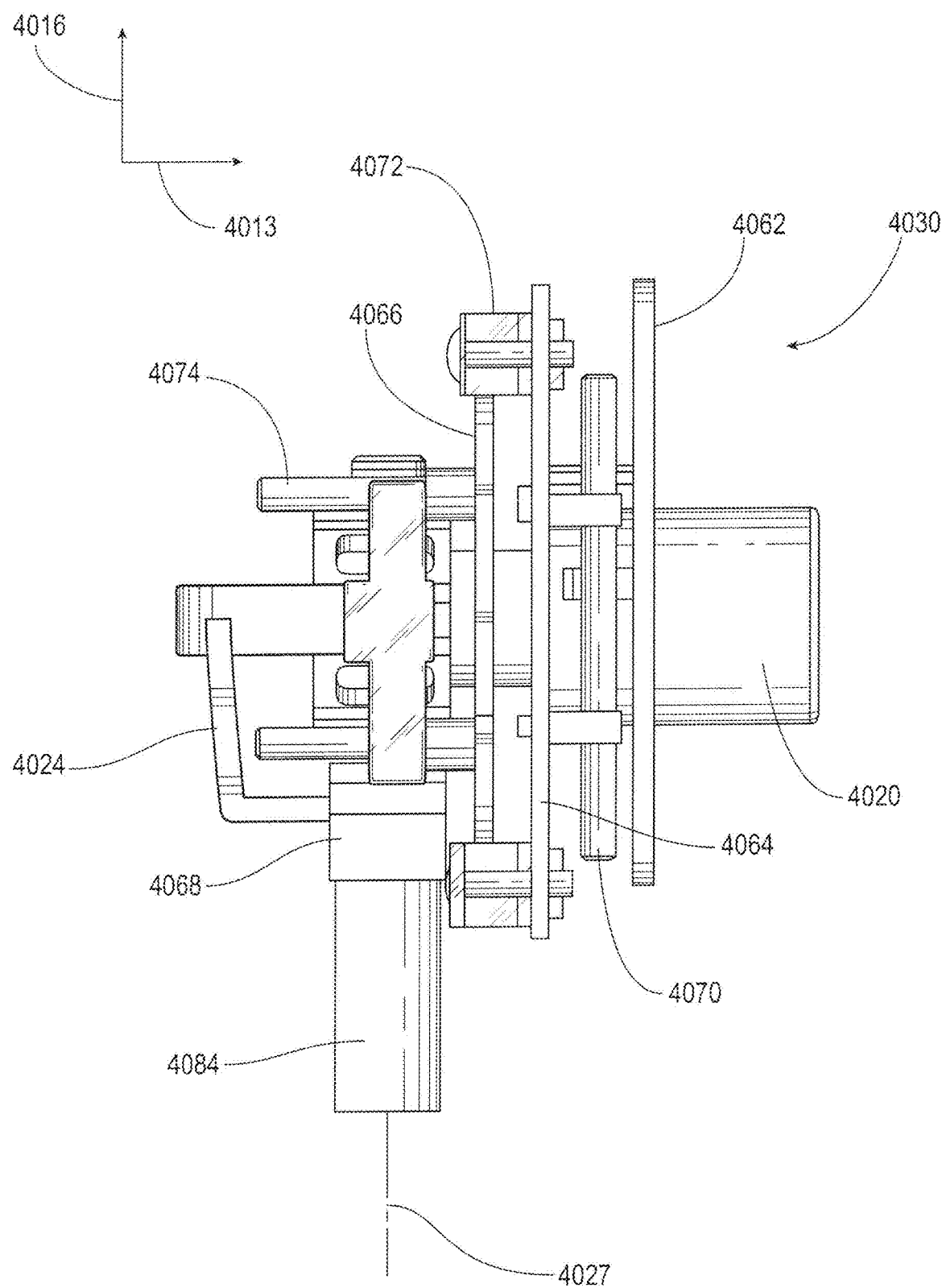
FIG. 32 is a right side elevation view of the support structure of FIG. 30.
Figure 33:
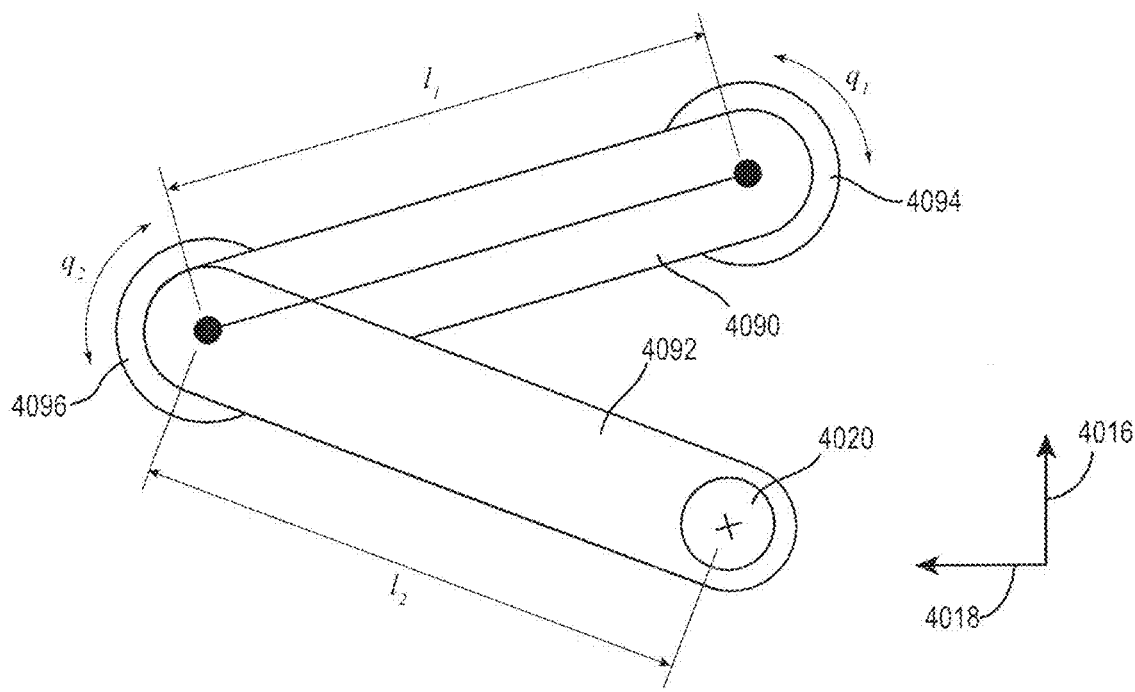
FIG. 33 is a schematic front view diagram of the support structure of FIG. 27.
Figure 34:
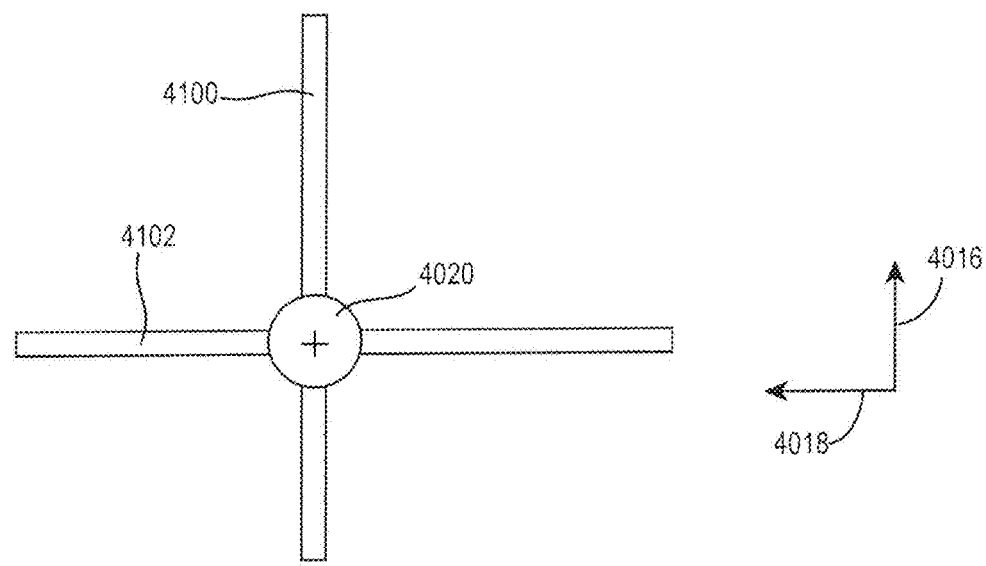
FIG. 34 is a schematic front view diagram of the support structure of FIG. 30.

Referring now to FIG. 30, FIG. 31, and FIG. 32, a support structure 4060 for the probe 4020 and the gimbal structure 4024 is shown according to another exemplary embodiment as a prismatic (e.g., Cartesian, rectilinear, etc.) robot. FIG. 30 illustrates an exemplary Prismatic-Prismatic-Prismatic robot. The support structure 4060 includes a first frame member 4062, a second frame member 4064, a third frame member 4066, a fourth frame member 4068, and the gimbal structure 4024. The first frame member 4062 is configured to be a static member. The first frame member 4062 may, for example, be mounted to a halo or headset 4033 worn on the patient's or subject's head or other structure that fixes the position of the first frame member 4062 relative to the patient or subject.

The second frame member 4064 is configured to translate along the y-axis 4016 (e.g., up and down, bottom of ear to top of ear, etc). According to an exemplary embodiment, the second frame member 4064 slides along rail members 4070 that are fixed to the first frame member 4062. The position of the second frame member 4064 relative to the first frame member 4062 is controlled by an actuator, such as an electric motor and a lead screw (not shown for clarity).

The third frame member 4066 is configured to translate along the x-axis 4018 (e.g., forward and backward, ear to eye, etc.). According to an exemplary embodiment, the third frame member 4066 slides along rail members 4072 that are fixed to the second frame member 4064. The rail members 4072 are orthogonal to the rail members 4070. The position of the third frame member 4066 relative to the second frame member 4064 is controlled by an actuator, such as an electric motor and a lead screw (not shown for clarity).

The fourth frame member 4068 is configured to translate along the z-axis 4013 (e.g., in and out, in and away from the head, etc.). According to an exemplary embodiment, the fourth frame member 4068 slides along rail members 4074 that are fixed to the third frame member 4066. The position of the fourth frame member 4068 relative to the third frame member 4066 is controlled by an actuator, such as an electric motor and a lead screw (not shown for clarity).

The gimbal structure 4024 and the probe 4020 are mounted to the fourth frame member 4068. The gimbal structure 4024 controls the orientation of the probe 4020 about the tilt axis 4027 and the pan axis 4029 (e.g., tilt and pan). The position of the probe 4020 about the tilt axis 4027 is controlled by an actuator 4084, shown as an electric motor and gearbox. The position of the probe 4020 about the pan axis 4029 is controlled by an actuator 4086, shown as an electric motor and gearbox.

The probe 4020 is able to move on the x-y plane through the translation of the second frame member 4064 and the third frame member 4066, move along the z-axis 4013 through the translation of the fourth frame member 4068, and rotate about tilt axis 4027 and the pan axis 4029 through the gimbal structure 4024. Combining these five actuated degrees of freedom allows the position and orientation of the probe 4020 relative to the target surface 4022 to be completely described and controlled, discounting rotation about a third axis that is orthogonal to the pan axis 4029 and the tilt axis 4027.

A kinematic model can be developed for any embodiment of a support structure for the probe 4020 to determine the relationship between the forces exerted at the probe 4020 and the forces applied by the actuators controlling the support structure.

A stiffness matrix for the support structure is first determined. The stiffness matrix is determined using a multitude of variables, including the physical properties of the support structure (e.g., the geometry of the frame members, the stiffness of the individual frame members etc.), the system stiffness along the chosen coordinate system axis, and a velocity-based term for system damping. According to an exemplary embodiment, the desired stiffness of the support structure is defined in the z direction ($K_z$), the y direction ($K_y$), and the x direction ($K_x$)(e.g., as represented by the virtual springs 4011, 4014, and 4017 in FIG. 25), and about the pan axis 4029 ($K\omega_x$) and about the tilt axis 4027 ($K\omega_y$)(e.g., as represented by the virtual torsional springs 4023 and 4025 in FIG. 25). As described above, in some embodiments, the virtual stiffnesses vary over time and are based on the task being accomplished with the probe 4020. For example, stiffness in the y direction and in the x direction may have a lower bound corresponding to a relatively low lateral stiffness during a set-up or removal procedure, in which the support structure is configured to be relatively compliant; and an upper bound corresponding to a relatively high stiffness during a scanning procedure, in which the support structure is configured to be relatively stiff, allowing for a more accurate positioning of the probe 4020. Likewise, stiffness in the z direction may have a lower bound corresponding to a relatively low stiffness during initial positioning of the probe 4020 in the z direction, in which the support structure is configured to be relatively compliant to allow the probe 4020 to self-align (e.g., to minimize discomfort for the patient or subject); and an upper bound corresponding to a relatively high stiffness during a scanning procedure, in which the support structure is configured to more stiff, to overcome friction forces between the probe 4020 and the target surface 4022 and to maintain the orientation of the probe 4020. Further, rotational stiffnesses about the y axis and the x axis may have a lower bound corresponding to a relatively low rotational stiffness during positioning of the probe 4020 to conform to the contour of the target surface 4022 (e.g., the head of the patient or subject), in which the support structure (e.g., the gimbal structure 4024) is configured to be relatively compliant (e.g., to minimize discomfort for the patient or subject); and an upper bound corresponding to a relatively high rotational stiffness when a more accurate positioning (e.g., panning, tilting, etc.) of the probe 4020 is desired.

A force vector is then derived using the following equation:

$$\vec{F} = K \Delta \vec{x} \qquad \text{(Eq. 16)}$$

where K is the stiffness matrix and $\Delta \vec{x}$ is the vector of the difference of the desired and actual translational position in the x, y, and z directions and rotational position about the x-axis 404018 and y-axis 16 of the probe 4020.

The force applied by the actuators (e.g., the torque applied by rotational actuators) controlling the position of the support structure may then be determined using the following equation:

$$\tau = J^T \vec{F} \qquad \text{(Eq. 17)}$$

where $J^T$ is the Jacobian transpose determined by the kinematics of the specific support structure. The Jacobian is the differential relationship between the joint positions and the end-effector position and orientation (e.g., the position of the probe 4020). The joint positions are either in units of radians (e.g., for rotational joints), or in units of length (e.g., for prismatic or linear joints). The Jacobian is not static and changes as the support structure position articulates.

Referring now to FIG. 29, a schematic front view diagram of the support structure 4030 is shown. The second frame member 4034 is represented by a first link 4090, having a length $l_1$. The first link 4090 is articulated by a rotary actuator 4094, the rotation of which is shown as $q_1$. The third frame member 4036 is represented by a second link 4092, having a length $l_2$. The second link 4092 is articulated by a rotary actuator 4096, the rotation of which is shown as $q_2$. The actuators 4094 and 4096 move the probe 4020 in the x-y plane.

The forward kinematics of this device are:

$$c_1 = \cos(q_1),$$

$$s_1 = \sin(q_1),$$

$$c_{12} = \cos(q_1 + q_2),$$

$$s_{12} = \sin(q_1 + q_2),$$

$$x = l_1 c_1 + l_2 c_{12} \qquad \text{(Eq. 18)}$$

$$y = l_1 s_1 + l_2 s_{12} \qquad \text{(Eq. 19)}$$

The Jacobian for such a revolute-revolute robot is derived by taking the partial derivative of the forward kinematics with respect to both $q_1$ and $q_2$.

$$J = \begin{bmatrix} -l_1 s_1 - l_2 s_{12} & -l_2 s_{12} \\ l_1 c_1 + l_2 c_{12} & l_2 c_{12} \end{bmatrix} \qquad \text{(Eq. 20)}$$

The Jacobian shown in Eq. 20 is the Jacobian for the Cartesian movement of the revolute-revolute robot on the x-y plane (e.g., translation along the y-axis 4016 and the x-axis 4018), describing the differential relationship between joint motion and probe motion. One of ordinary skill in the art would understand that in other embodiments, additional terms may be included in the Jacobian to describe the differential relationship between the motion of the probe 4020 and other motions of the robot (e.g., rotation of the probe 4020 about the tilt axis 4027 and the pan axis 4029 and translation along the z-axis 4013).

Referring now to FIG. 30, a schematic front view diagram of the support structure 4060 is shown. The probe 4020 is moved in the y direction by a first linear actuator 4100 (e.g., an electric motor and lead screw) and is moved in the x direction by a second linear actuator 4102 (e.g., an electric motor and lead screw). The actuators 4100 and 4102 move the probe 4020 in the x-y plane. Because each joint is orthogonal to the other, and has a one to one mapping of joint motion to Cartesian motion, the Jacobian for such a prismatic robot becomes the identity matrix:

$$J = \begin{bmatrix} 1 & 0 \\ 0 & 1 \end{bmatrix} \qquad \text{(Eq. 21)}$$

The Jacobian shown in Equation 21 is the Jacobian for the Cartesian movement of the prismatic robot on the x-y plane (e.g., translation along the y-axis 4016 and the x-axis 4018), describing the differential relationship between joint motion and probe motion. In other embodiments, additional terms may be included in the Jacobian to describe the differential relationship between the motion of the probe 4020 and other motions of the robot (e.g., rotation of the probe 4020 about the tilt axis 4027 and the pan axis 4029 and translation along the z-axis 4013).

Referring to FIG. 27, The support structure 4030 controls the position of the probe 4020 in the z direction with the translation of the fourth frame member 4038 with a single linear actuator (e.g., an electric motor and lead screw). Referring to FIG. 30, Similarly, the support structure 4060 controls the position of the probe 4020 in the z direction with the translation of the fourth frame member 4068 with a single linear actuator (e.g., an electric motor and lead screw). For either support structure, there is a direct correlation between the position of the actuator and the position of the probe 4020.

Figure 35:
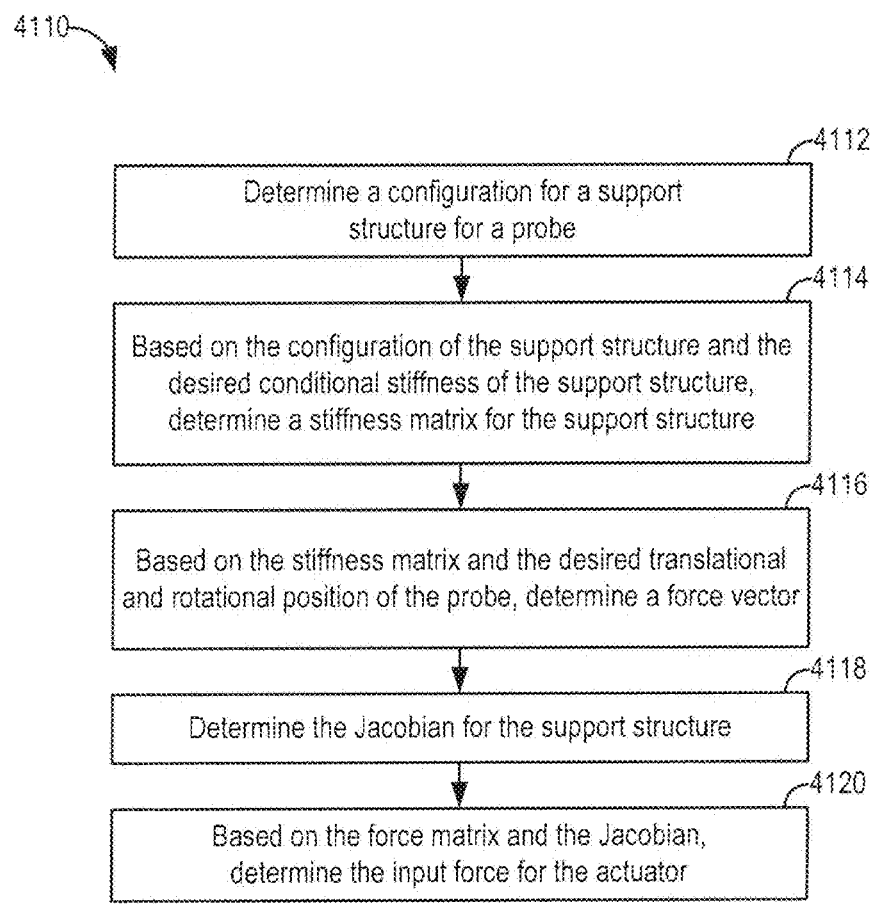
FIG. 35 is a flowchart of a method for determining the input force, or torque, for an actuator, according to an exemplary embodiment.

Referring now to FIG. 35, a method 4110 of determining the input force, or torque, for an actuator for a probe support structure is shown according to an exemplary embodiment. The configuration of the support structure for a probe is first determined (step 4112). The configuration may include any number of revolute joints and/or prismatic joints. In some embodiments, the support structure provides translation of the probe along one or more axis (e.g., the x, y, and z axis in a Cartesian coordinate system; the r, θ, and z axis in a polar coordinate system, etc.) and/or rotation about one or more axis.

Based on the configuration of the support structure and the desired variable stiffness of the support structure, a stiffness matrix for the support structure is determined (step 4114). The stiffness matrix includes terms based on the physical properties of the support structure, including the geometry of the frame members and the stiffness of the individual frame members, the desired stiffness of the support structure in the z direction (Kz), the y direction (Ky), and the x direction (Kx), the desired rotational stiffness of the support structure ($K\omega_x$, $K\omega_y$), and a velocity-based term for system damping.

Based on the stiffness matrix and the desired translational and rotational position of the probe, a force vector is determined (step 4116). The desired position of the probe may be determined using any coordinate system. According to an exemplary embodiment, the force vector is derived from the product of the stiffness matrix and a matrix of the desired translational and rotational position of the probe, as shown in Equation 1.

The Jacobian for the support structure is then calculated (step 4118). The Jacobian is determined by the kinematics of the specific support structure. The Jacobian is the differential relationship between the joint positions and the end-effector position. The joint positions are either in units of radians (e.g., for rotational joints), or in units of length (e.g., for prismatic or linear joints). The Jacobian is not static and changes as the support structure position articulates.

Based on the force vector and the Jacobian, the input force for the actuator is determined (step 4120). According to an exemplary embodiment, the input force for the actuator is derived from the product of the Jacobian and the force vector, as shown in Eq. 17.

Figure 36:
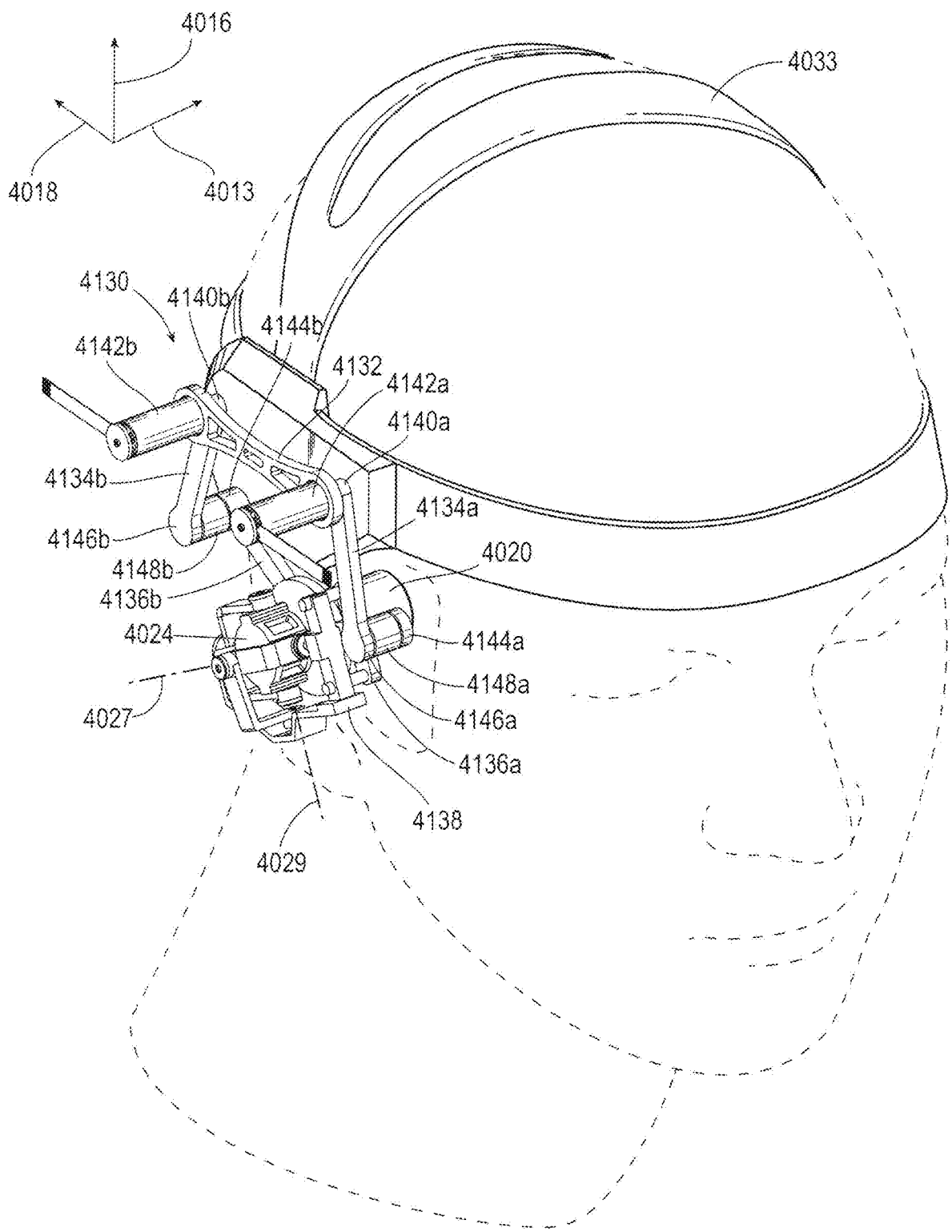
FIG. 36 is a perspective view of a 5-bar parallel mechanism (revolute-revolute) support structure for the medical probe of FIG. 26, according to an exemplary embodiment.
Figure 37:
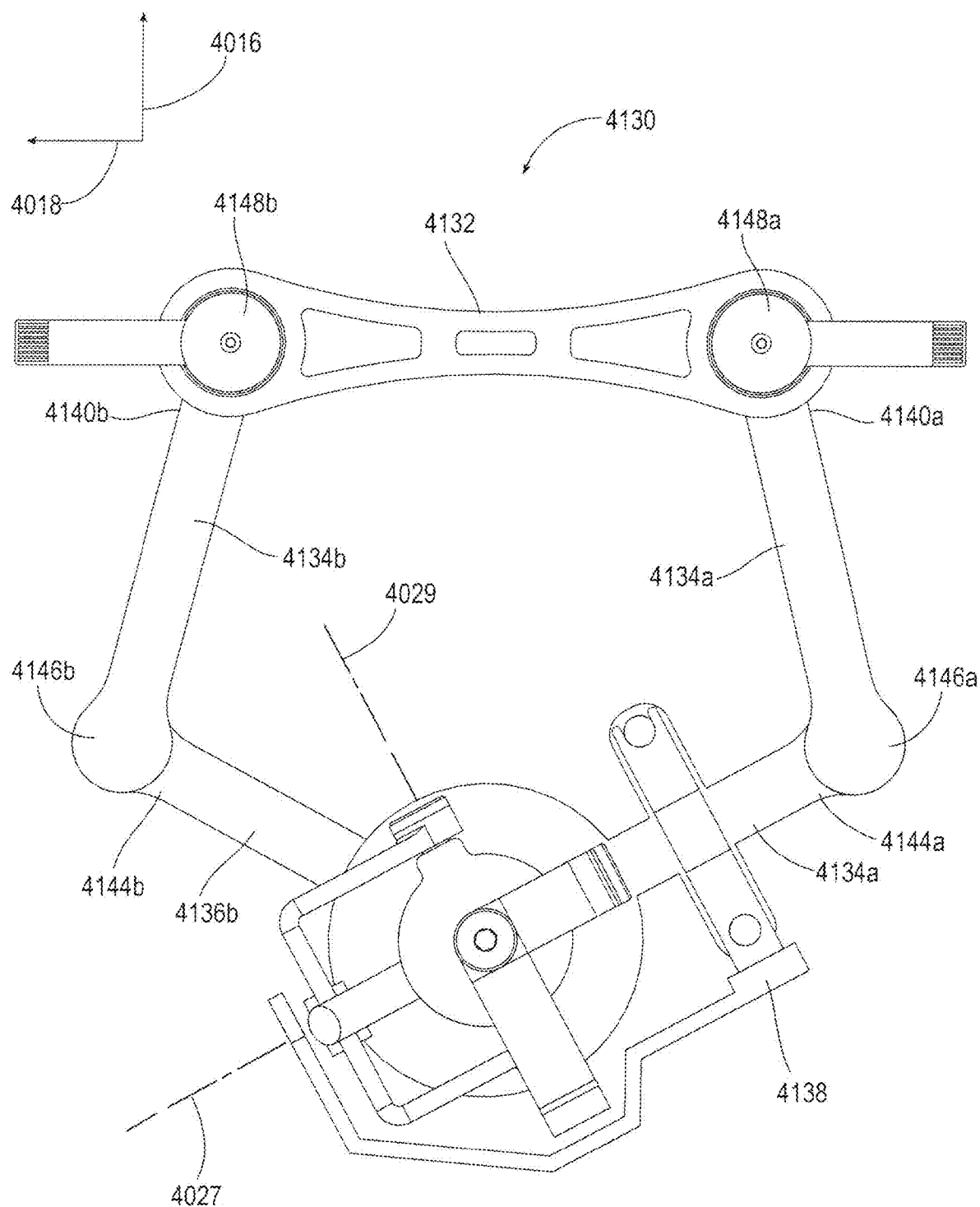
FIG. 37 is front elevation view of the support structure of FIG. 36.
Figure 38:
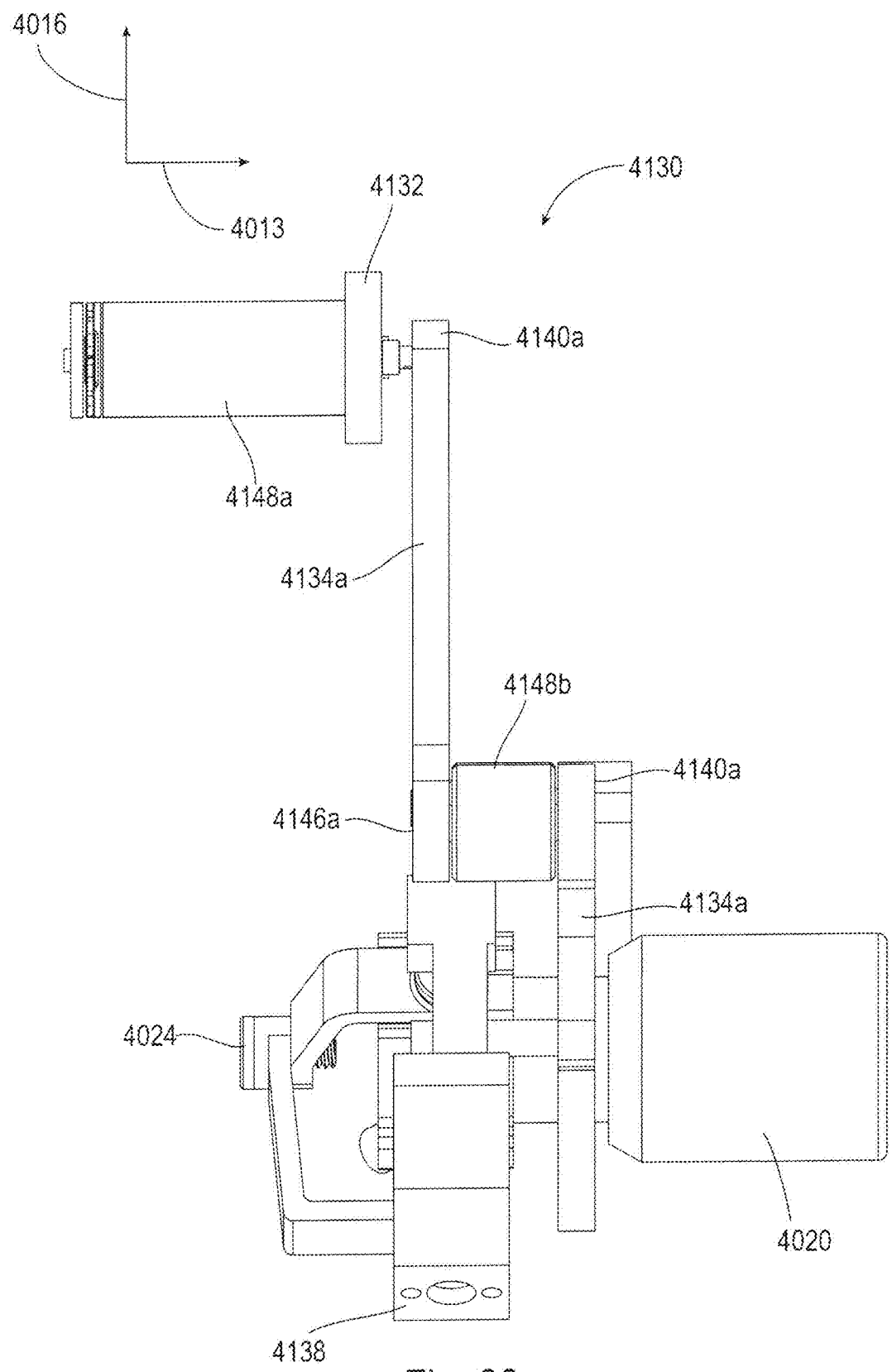
FIG. 38 is a right side elevation view of the support structure of FIG. 36.

Referring now to FIG. 36, FIG. 37, and FIG. 38, a support structure 4130 for the probe 4020 is shown according to another exemplary embodiment as a five-link revolute robot. The support structure 4130 includes a first frame member 4132; a pair of proximal members coupled to the first frame member 4132, shown as a second frame member 4134a and a third frame member 4134b; a pair of distal members coupled to the respective proximal frame members and to each other, shown as a fourth frame member 4136a and a fifth frame member 4136b; a sixth frame member 4138 coupled to the distal frame members; and the gimbal structure 4024. The first frame member 4132 is configured to be a static member. The first frame member 4132 may, for example, be mounted to a halo or headset 4033 worn on the patient's or subject's head or other structure that fixes the position of the first frame member 4132 relative to the patient or subject.

The second frame member 4134a and the third frame member 4134b are links configured to rotate about the z-axis 4013. A first end 4140a of the second frame member 4134a is coupled to the first frame member 4132. Similarly, a first end 4140b of the third frame member 4134b is coupled to a separate portion of the first frame member 4132. According to an exemplary embodiment, the rotation of the second frame member 4134a relative to the first frame member 4132 is controlled by an actuator 4142a, shown as an electric motor and gearbox that is attached through the first frame member 4132. According to an exemplary embodiment, the rotation of the third frame member 4134b relative to the first frame member 4132 is controlled by an actuator 4142b, shown as an electric motor and gearbox that is attached through the first frame member 4132.

The fourth frame member 4136a and the fifth frame member 4136b are links configured to rotate about the z-axis 4013. A first end 4144a of the fourth frame member 4136a and a second end 4146a of the second frame member 4134a are each coupled to a hub member 4148a via bearings (e.g., press fit bearings, etc.). Similarly, a first end 4144b of the fifth frame member 4136b and a second end 4146b of the third frame member 4134b are each coupled to a hub member 4148b via bearings (e.g., press fit bearings, etc.).

The fourth frame member 4136a and the fifth frame member 4136b are coupled together via a bearing (e.g., a press fit bearing, etc.) to form a five-bar linkage. The hub members 4148a and 4148b offset the proximal members from the distal members along the z-axis 4013, which allows the proximal frame members (e.g., second frame member 4134a and third frame member 4134b) to move freely past the distal frame members (e.g., fourth frame member 4136a and fifth frame member 4136b) as the links are rotated by the actuators 4142a and 4142b.

The gimbal structure 4024 and the probe 4020 are mounted to the sixth frame member 4138. The sixth frame member 4138 is coupled to one of the distal members (e.g., fourth frame member 136a or fifth frame member 4136b) and is configured to translate the gimbal structure 4024 and the probe 4020 along the z-axis 4013 (e.g., in and out, in and away from the head, etc.). The sixth frame member 4138 may translate, for example, on rails, as described above in regards to the fourth frame member 4038 of the support structure 4030 (see FIG. 36, FIG. 37, FIG. 38). The gimbal structure 4024 controls the orientation of the probe 4020 about the tilt axis 4027 and the pan axis 4029 (e.g., pan and tilt). The position of the probe 4020 about the tilt axis 4027 is controlled by an actuator (not shown), such as an electric motor and gearbox. The position of the probe 4020 about the pan axis 4029 is controlled by an actuator (not shown), such as an electric motor and gearbox. In one embodiment, the rotation of the probe 4020 about the tilt axis 4027 and the pan axis 4029 is different than the z-axis 4013, regardless of the rotation of the frame members 4134 and 4136.

The probe 4020 is able to move on the x-y plane through the movement of the five-bar linkage formed by the first frame member 4132, the second frame member 4134a, the third frame member 4134b, the fourth frame member 4136a, and the fifth frame member 4136b. The probe 4020 is able to move along the z-axis 4013 through the translation of the sixth frame member 4138. Further, the probe 4020 is able to rotate about tilt axis 4027 and the pan axis 4029 through the gimbal structure 4024. Combining these five actuated degrees of freedom allows the position and orientation of the probe 4020 relative to the target surface 4022 to be completely described and controlled, discounting rotation about a third axis that is orthogonal to the pan axis 4029 and the tilt axis 4027.

According to an exemplary embodiment, the actuators utilized to position the support structure 4130 are servo motors. Of course, any suitable motors could be used instead of servo motors. The use of servo motors to control the support structure allow for a more precise control, compared to a stepper motor, over the rotational position and angular speed of the motor, as well as the corresponding position of the probe 4020 and the interaction between the probe 4020 and the target surface 4022.

The input forces for the actuators 4142a and 4142b can be calculated in a manner similar to that described above by determining the force vector, determining the forward kinematics of the support structure 4130, and calculating the Jacobian by taking the partial derivative of the forward kinematics with respect to the rotations of each of the actuators 4142a and 4142b.

In some embodiments, for probe 4020 contact and seating, instead of trying to predict and control the exact position and orientation of the probe 4020, the impedance of the probe 4020 is selectively controlled, whether by mechanical design or through software. As such, the orientation degrees of freedom of the probe 4020 can be compliant so that they rotate against contact and seat the probe 4020 flush with the head, while the translation degrees of freedom are stiff enough to move the probe 4020 and keep it placed against the head. In some embodiments, each of the directions has different impedances.

In some embodiments, software is implemented to limit motor torque and motor servo stiffness of the probe 4020. In some embodiments, there may be different limits for each direction, creating different stiffnesses in different directions. In some embodiments, the pan and tilt are very compliant, while the translational motions are moderately stiffer. In some embodiments, stiffness through the probe 4020 is more compliant than the X, Y translational degrees of freedom.

In some embodiments, software is implemented for task space impedance control. In other words, there can be considered the probe 4020 orientation to define a local coordinate system with the Z axis through the center of the probe 4020. Instead of manipulating the impedance of the probe 4020 by adjusting motor servo stiffness and torque limiting, in some embodiments, the kinematics of the entire robot can be considered to set the impedance of each of the five directions, X, Y, Z, pan, and tilt, local to the probe's 4020 coordinate frame. As such, the probe 4020 can be more compliant through the center line of the probe 4020, but still maintain contact with the surface of the skin, but have local X and Y stiffness sufficient to control the location of the probe 4020 with precision.

According to various embodiments, the probe 4020 includes a series elastic actuator. In some embodiments, the impedance of the device is altered by adding a compliant member into the mechanical design, either as a spring element into the motor or as a structural member of the robot. In some embodiments, measurement of the amount of deflection is implemented in order to measure the exact position and orientation of the probe 4020. A series elastic actuator has the benefit of being designed to an exact compliance, and even has a damping element added, while avoiding computational nonlinearities and instabilities associated with programming the impedance.

In some embodiments, the force is indirectly measured by monitoring the applied current of the motor. For the static case, taking into account the kinematics of the robot, the force/torque vector of the system is computed from the Jacobian: $F=(J^T)^{-1}\tau$, where $\tau$ is the vector of motor torques as predicted by the applied current to the motor.

In some embodiments, the interaction force and torque between the probe 4020 and the head is controlled by placing a force/torque sensing mechanism behind the probe 4020. The position and orientation of the probe is specified in relation to the measured forces and torques to achieve a desired force/torque vector. This type of closed loop controller is called admittance control and is programmed into the software. Admittance control relates the measured force to a desired probe position and orientation, as illustrated in the following equation.

$$\vec{X}_{desired} = G_{control} \vec{F}_{measured}$$

Figure 39:
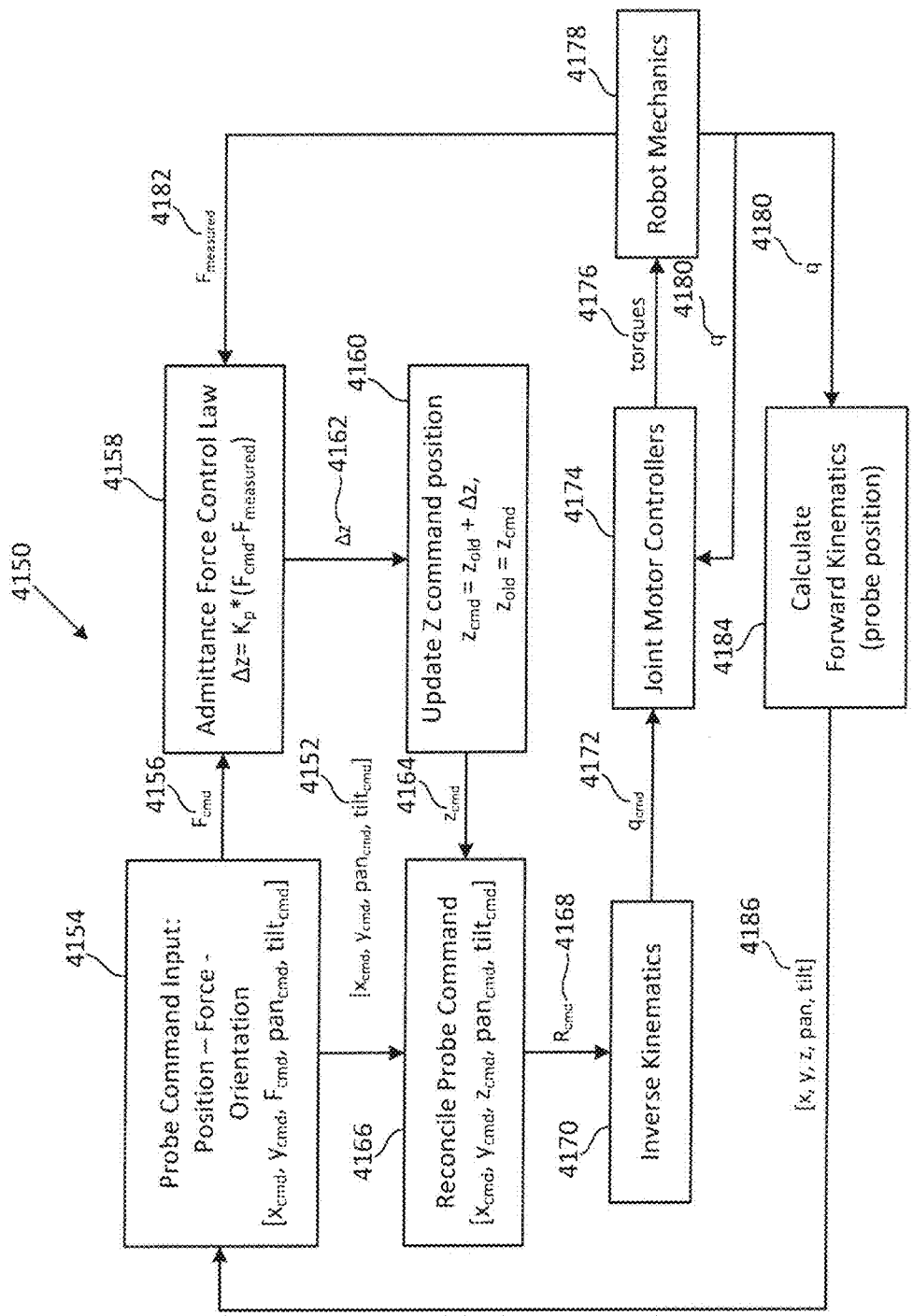
FIG. 39 illustrates a hybrid position-force admittance controller.

The desired position vector is used to compute desired joint positions from the inverse kinematics. Motor joint controllers are programmed with high servo stiffness to enhance disturbance rejection and have low servo tracking errors. A hybrid position-force admittance controller 4150 is illustrated in FIG. 39.

In this example of a hybrid position-force controller, force is controlled in the z direction of the probe, while position is controlled in the x and y directions, and the pan and tilt orientations. A hybrid command of positions and force in task space, $[x_{cmd}, y_{cmd}, F_{cmd}, pan_{cmd}, tilt_{cmd}]$ 4152, is sent by the probe command input block 4154, which determines task oriented moves of the probe, such as searching. In this case the position and orientation is specified in x, y, pan and tilt, and is given in units of length and angle (mm and radians). Force is specified in the z direction, and is given in units of Newtons. For an admittance controller, the force command must be transformed into a desired position. The force command, $F_{cmd}$ 4156, is extracted from the probe input command block 4154 as used as the command for the admittance force control law block 4158. Using the measured force, $F_{measured}$, a change in z position, $\Delta z$, is computed by the admittance force control law block 4158. A simple, single proportional gain controller is illustrated, but other controller forms can be used. In the update z command position block 4160, $\Delta z$ 4162 is added to the old z command position to create an updated z command, $Z_{cmd}$ 4164. This information is merged with the other probe position and orientation commands in the reconcile probe command block 4166. The reconciled command, $R_{cmd}$ 4168 specifies the probe position and orientation in units of length and angle, $[x_{cmd}, y_{cmd}, z_{cmd}, pan_{cmd}, tilt_{cmd}]$. The inverse kinematics block 4170 uses the reconciled command, $R_{cmd}$ 4168 to solve for the new robot joint command position, $g_{cmd}$ 4172, based on the mechanics of the specific robot. It is understood from the discussion above that the robot could have a direct analytic inverse solution, or a numerical solution based on the inverse or pseudo inverse Jacobians depending on the number of degrees of freedom.

The joint command position, $q_{cmd}$ 4172, is used as the input for the inner position control loop comprised of the joint motor controllers block 4174, the output torques 4176, robot mechanics block 4178, which is the physical robot, and the measured joint positions, q 4180. The robot mechanics block 4178 also includes a force sensor which outputs the measured force, $F_{measured}$ 4182. The measured force, $F_{measured}$ 4182 is the second input to the admittance force control law block 4158, which closes the force control loop.

The measured joint positions, q 4180, are used as the to the calculate forward kinematics block 4184, which computes the current probe position and orientation [x,y,z,pan,tilt] 4186, and sends it back to the probe command input block 4154, for use in its probe command generation algorithm.

When combined with an impedance law, different directional and orientational stiffnesses at the probe 4020 can be programmed. Admittance control is appropriate for non-backdriveable motors, which are more difficult to use with pure impedance controllers because, without a force-torque sensor, the static friction resisting the user is unobservable while at rest.

Other configurations of the support structure include over and under actuated mechanisms. An over-actuated mechanism, or redundant manipulator, includes more actuated degrees of freedom than task space coordinates that are attempted to be controlled; e.g., the number of motors, Q={J1, J2, J3, J4, J5, . . . ) is greater than the five degrees of freedom in position and orientation X={x, y, z, pan, tilt} of the probe that is being controlled. For such mechanisms there will be many, and possibly an infinite number, of inverse kinematic solutions.

An example of an over-actuated mechanism, or redundant manipulator, is the UR3 Robot, made by Universal Robots, which has six rotating joints, each controlled by its own actuator or motor, to allow for six actuated degree of freedom movement.

Figure 40:
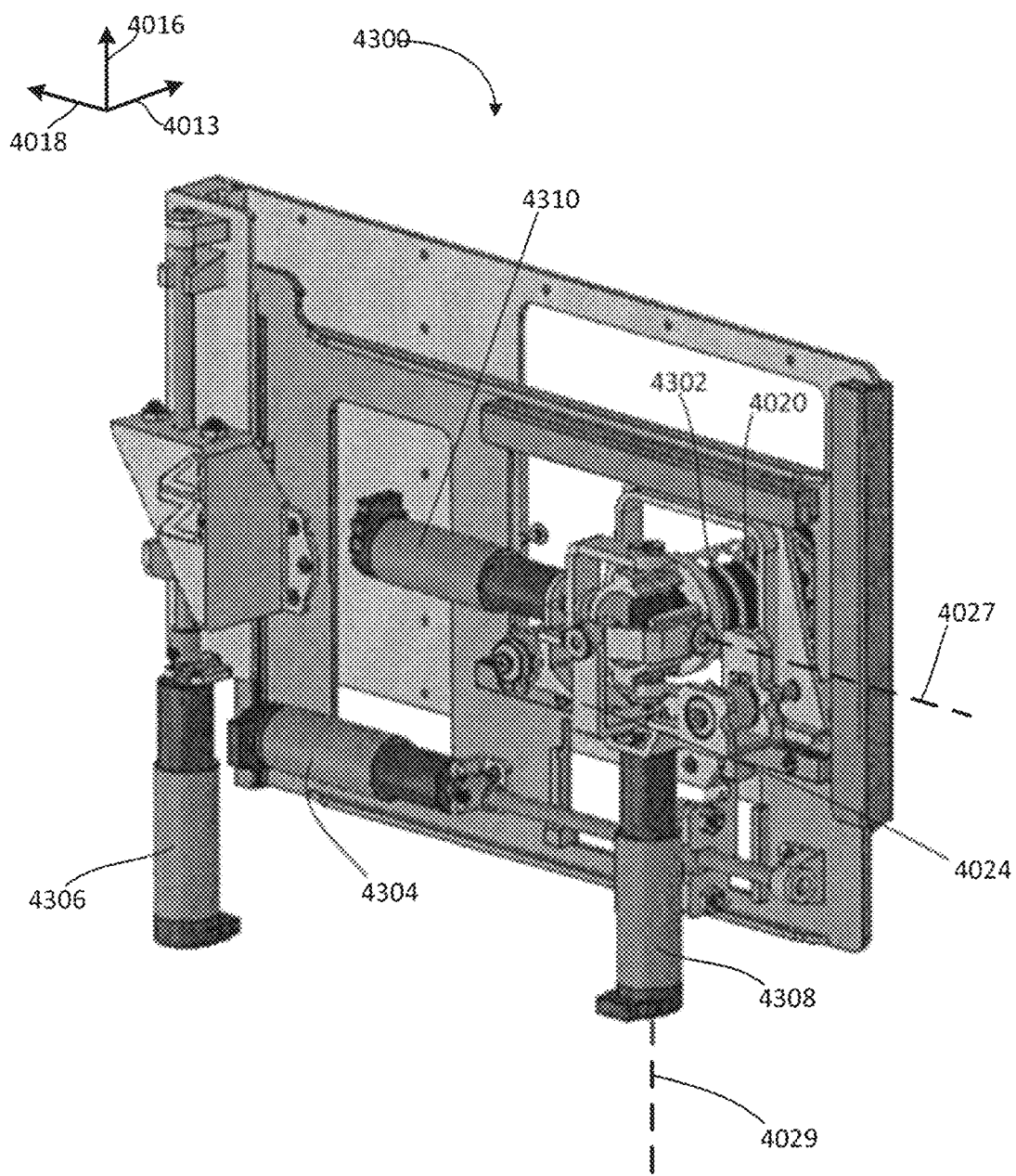
FIG. 40 illustrates a top perspective view of a spring loaded probe in a support structure with four actuated degrees of freedom as well as one passive degree of freedom.
Figure 41:
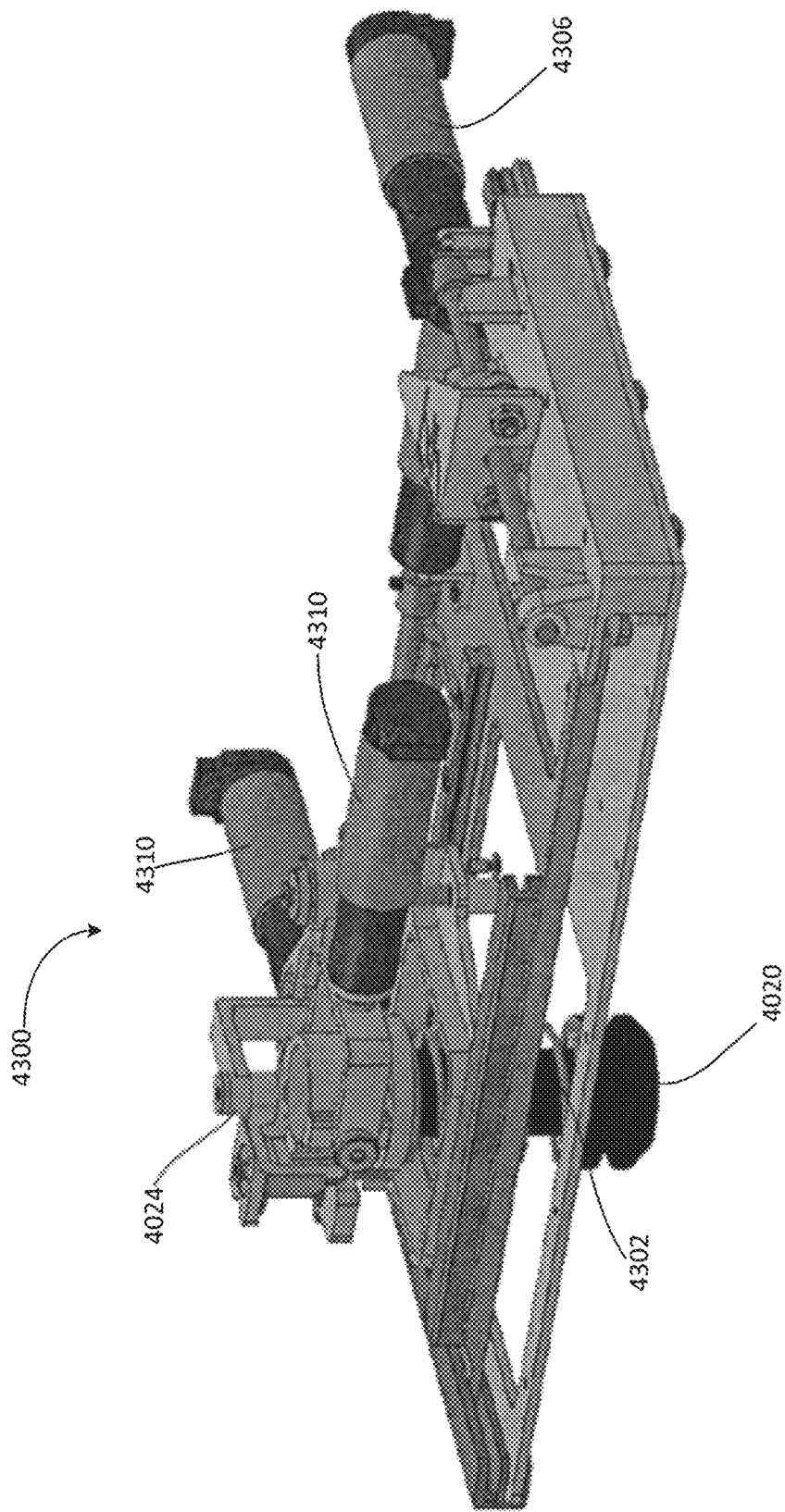
FIG. 41 illustrates a front perspective view of a spring loaded probe in a support structure with four actuated degrees of freedom as well as one passive degree of freedom.
Figure 42:
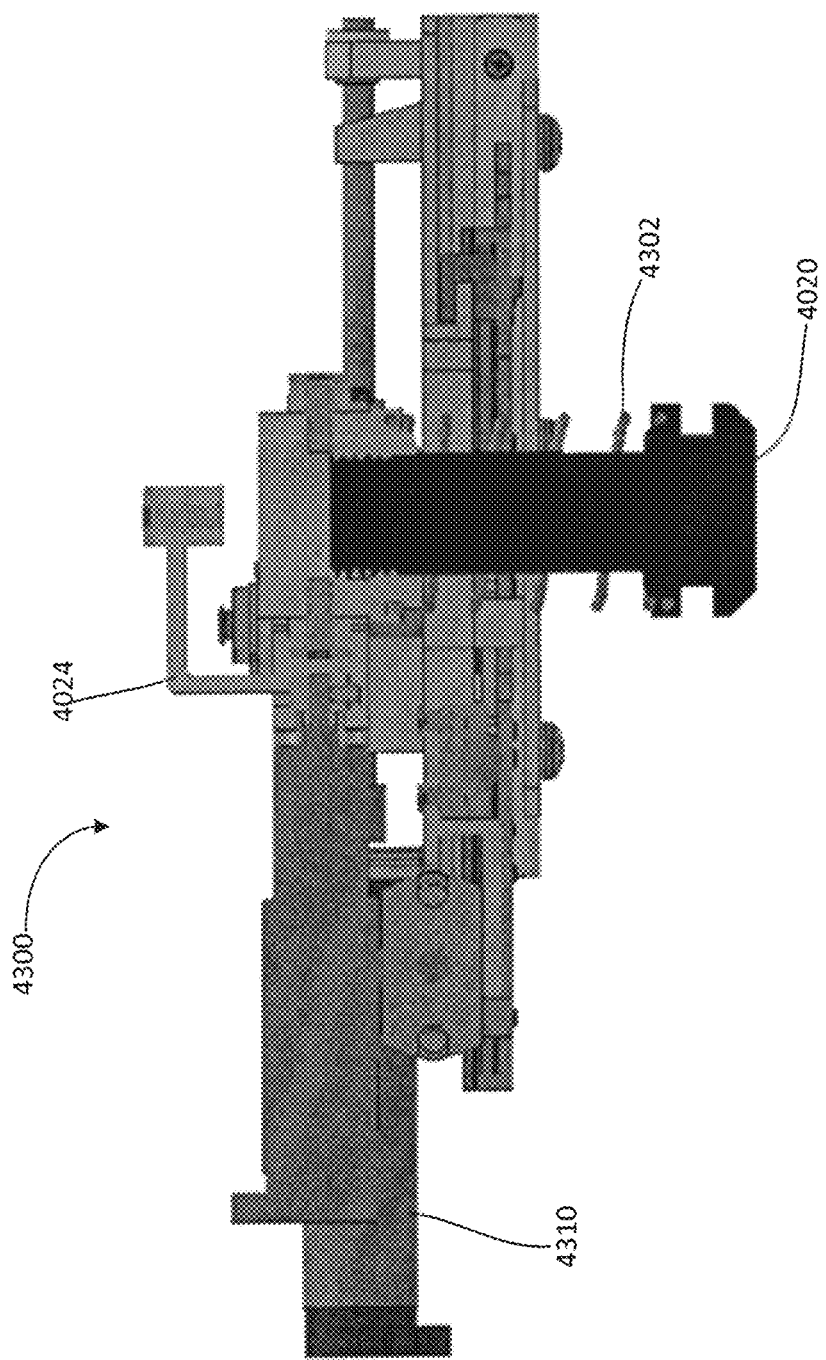
FIG. 42 illustrates a cross-sectional view of a spring loaded probe in a support structure with four actuated degrees of freedom as well as one passive degree of freedom.

Referring now to FIG. 40, FIG. 41, and FIG. 42, an under actuated system 4300 is shown. Such a system has four actuated degrees of freedom in the x,y,pan,tilt axes and a spring providing force along the z axis. In the under actuated system 4300 shown, the system has fewer than five actuated degrees of freedom, but is still capable of performing the TCD positioning task. The under actuated system 4300 shown is a four actuated degree of freedom mechanism that can position and orient the probe 4020 in X={x, y, pan, tilt}. In the under actuated system 4300, a spring 4302 exerts force on the probe 4020 along a z-axis 4013. In five actuated degree of freedom systems the force exerted by the spring in under actuated system 4300 would be actuated by a motor driven mechanism. The gimbal structure 4024 allows the probe 4020 to be oriented. The force in the z-axis 4013 is in effect, monitored by the characterization of the spring constant associated with the spring 4302. The actuation in the x-axis 4018 is controlled by actuator 3404 shown as an electric motor and lead screw. The actuation in the y-axis 4016 is controlled by actuator 4306 shown as an electric motor and lead screw. The actuation in the pan axis 4029 is controlled by motor 4308. The actuation in the tilt axis 4027 is controlled by motor 4310.

Figure 43:
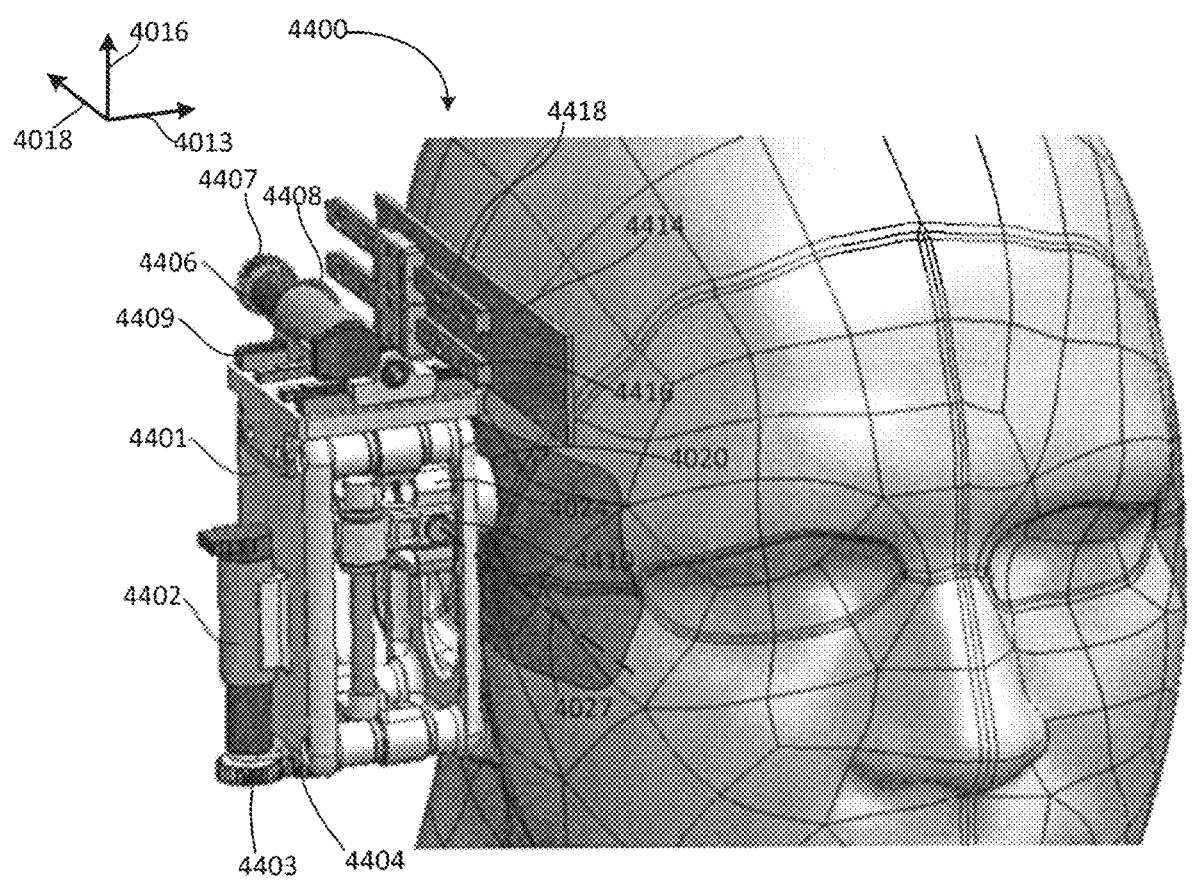
FIG. 43 illustrates a front perspective view of a five actuated degrees of freedom prismatic support structure for a medical probe, according to an exemplary embodiment.
Figure 45:
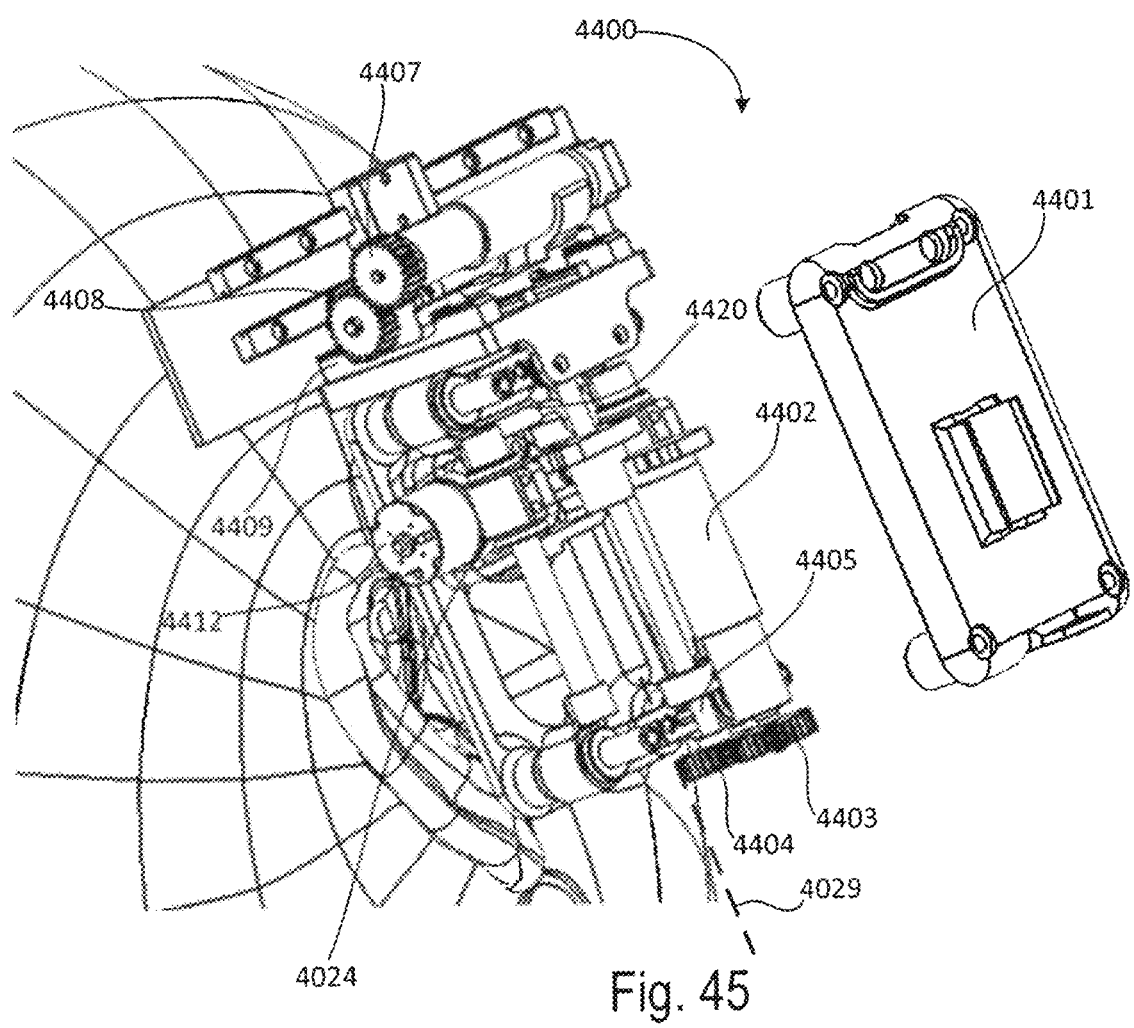
FIG. 45 illustrates an exploded perspective view of a five actuated degrees of freedom prismatic support structure for the a medical probe, according to an exemplary embodiment.

Referring now to FIG. 43, FIG. 45, and FIG. 45 a support structure 4400 is shown for the probe 4020 and the gimbal structure 4024 is shown according to another exemplary embodiment as a prismatic (e.g., Cartesian, rectilinear, etc.) robot. The support structure 4400 may, for example, be mounted to a halo or headset 4033 worn on the patient's or subject's head or other structure. The support structure 4400 includes a cover 4401 that covers some of the mechanisms of the support structure 4400. In FIG. 45, an exploded view of support structure 4400 shows the cover 4401 taken off the support structure 4400.

Figure 44:
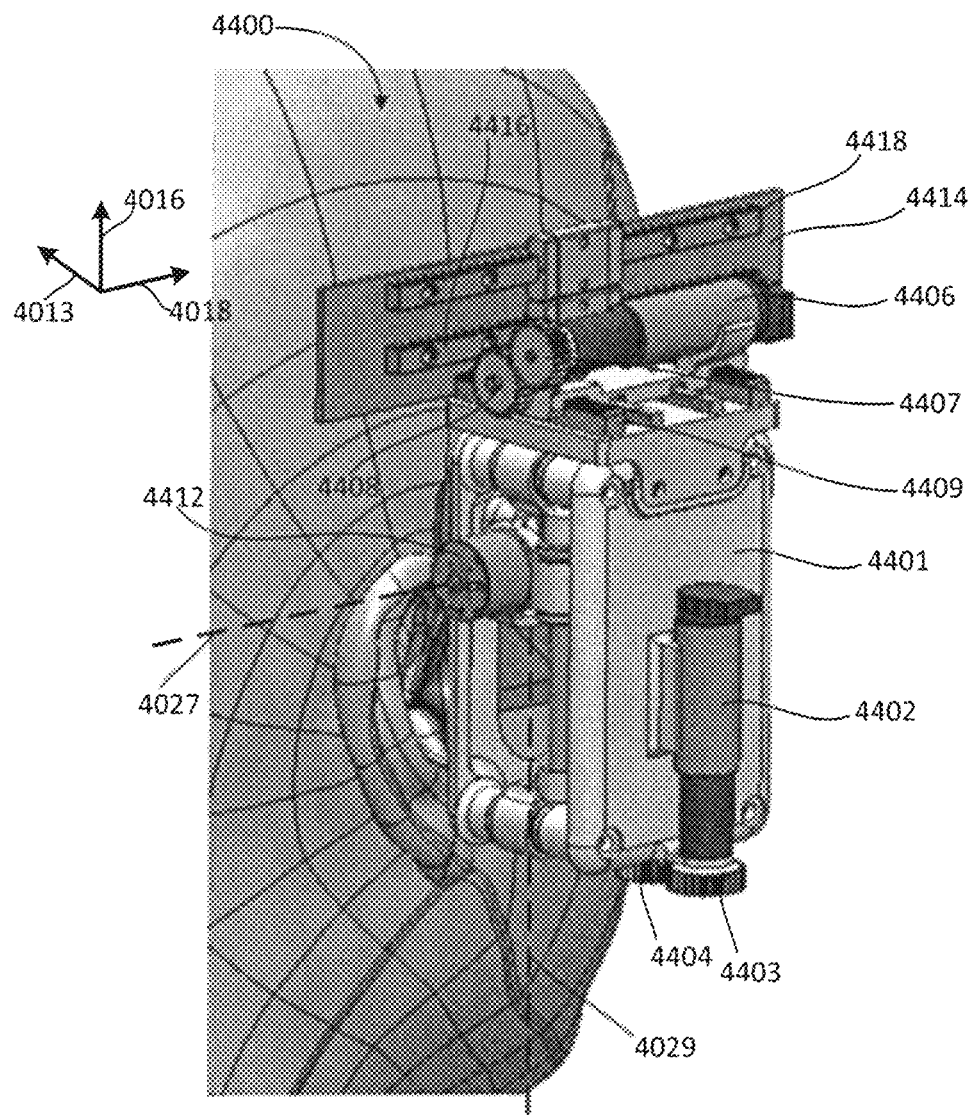
FIG. 44 illustrates a rear perspective view of a five actuated degrees of freedom prismatic support structure for the a medical probe, according to an exemplary embodiment.

A first motor 4402 is configured to use a first spur gear 4403 to actuate a lead screw 4405 mechanism. The first spur gear 4403 is coupled to a second spur gear 4404 which converts rotational motion of the first motor 4402 into linear motion along lead screw 4405 to translate the probe 4020 along a y-axis 4016 (e.g., up and down, bottom of ear to top of ear, etc). A second motor 4406 is configured to use a third spur gear 4407 coupled to a fourth spur gear 4408, which in turn is coupled to a rack and pinion mechanism 4409 to translate the probe 4020 along a z-axis 4013 towards and away from the head of a subject. As shown, in FIG. 44, a third motor 4412 and bearing 4410 allow for rotation of the gimbal 4024 about a tilt axis 4027, which in this embodiment, is parallel to x-axis 4018. A plate 4414 houses two linear rails 4416, 4418 and allows for mounting of a fourth motor (not shown for clarity) to translate along the x-axis 4018 (e.g., forward and backward, ear to eye, etc.). As shown in FIG. 45, a fifth motor 4420 allows for controlling rotation of the gimbal 4024 about pan axis 4029, which, in this embodiment is parallel to y-axis 4016, thus completing the necessary degrees of freedom to define five degree of freedom actuated robotic system.

H. Surface Alignment

Figure 46:
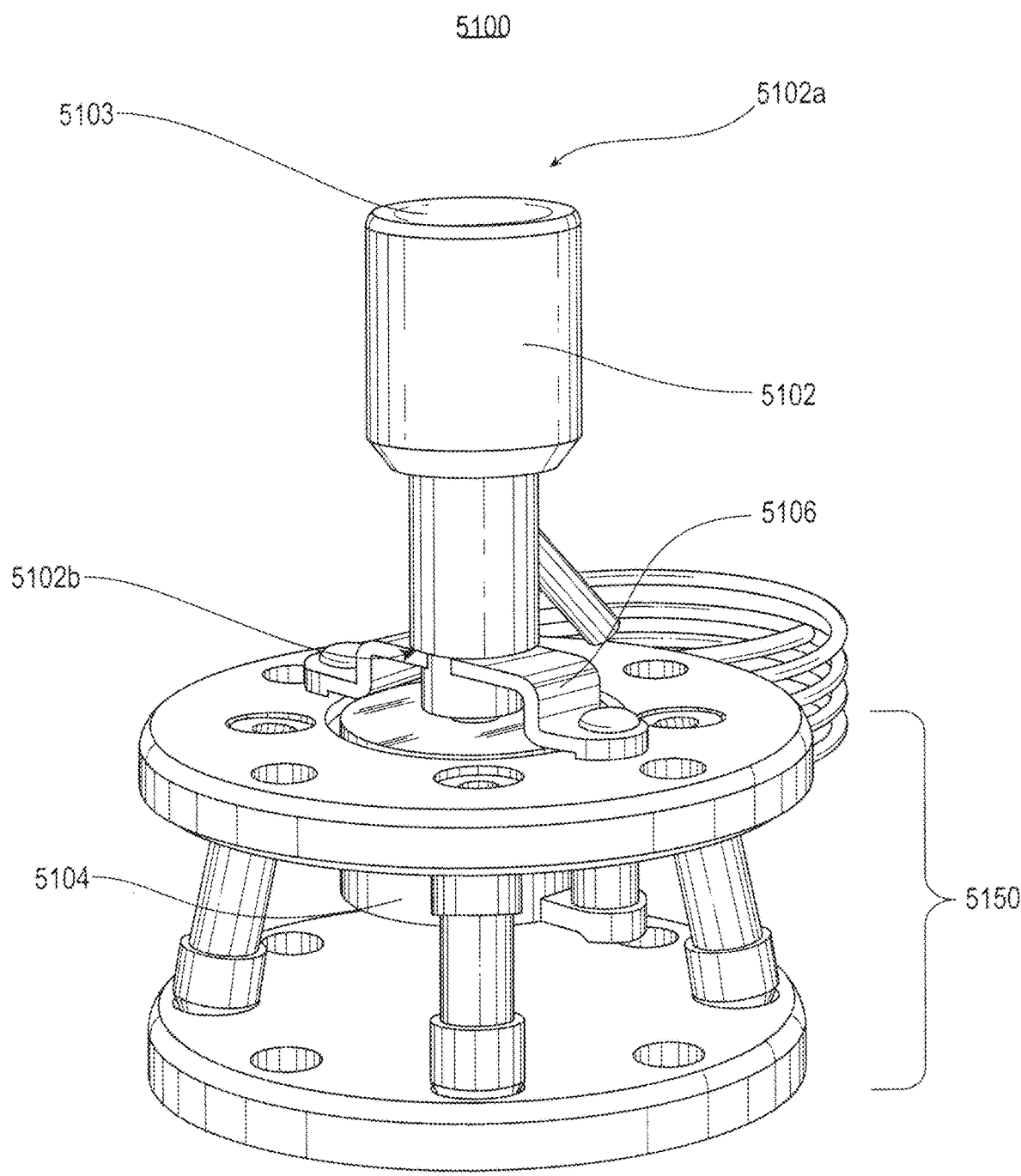
FIG. 46 illustrates a front perspective view of a remote center of compliance probe device according to various embodiments.
Figure 47:
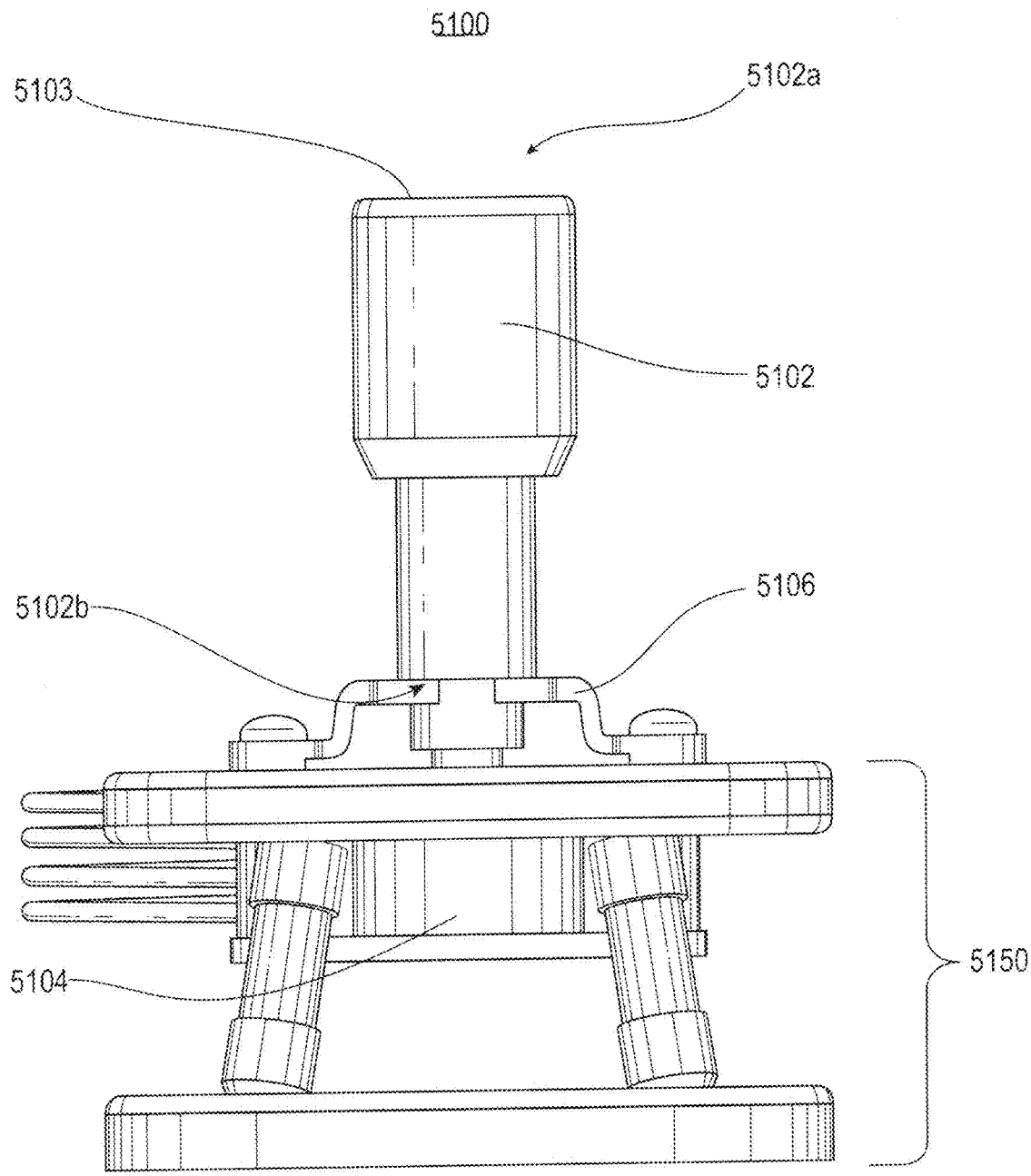
FIG. 47 illustrates a rear view of a remote center of compliance probe device according to various embodiments.

FIG. 46 illustrates a front perspective view of a remote center of compliance (RCC) probe device 5100 according to various embodiments. FIG. 47 illustrates a rear view of the RCC probe device 5100 according to various embodiments. Referring to FIG. 46 and FIG. 47, in some embodiments, the RCC probe device 5100 includes a probe 5102, an RCC assembly 5150, and a load cell 5104.

In some embodiments, the probe 5102 includes a first end 5102a and a second end 5102b that is opposite to the first end 5102a. In some embodiments, the first end 5102a includes a concave surface 5103 that is configured to be adjacent to or contact a scanning surface. The concave surface 5103 is configured with a particular pitch to focus generated energy towards the scanning surface. In some embodiments, the RCC probe device 5100 is a Transcranial Doppler (TCD) apparatus such that the first end 5102a of the probe 5102 is configured to be adjacent to or contact and align along a human head (e.g., a side of the human head), and the first end 5102a of the probe 5102 is configured to provide ultrasound wave emissions from the first end 5102a and directed into the human head (e.g., towards the brain). In other embodiments, the probe 5102 is configured to emit other types of waves during operation, such as, but not limited to, infrared waves, x-rays, or the like.

In some embodiments, the second end 5102b of the probe 5102 is coupled to the RCC assembly 5150. In some embodiments, the probe 5102 is connected to the RCC assembly 5150 via a connection interface 5106 that interposes the RCC assembly 5150 and the probe 5102. In some embodiments, the second end 5102b of the probe 5102 includes a threaded section along a portion of the body of the probe 5102, and the second end 5102b is configured to be secured in the connection interface 5106 via the threads (e.g., by being screwed into the connection interface 5106). In other embodiments, the probe 5102 is secured in the connection interface 5106 by any other suitable connecting means, such as, but not limited to, welding, adhesive, one or more hooks and latches, one or more separate screws, press fittings, or the like.

In some embodiments, the connection interface 5106 is connected to the RCC assembly 5150 by use of separate connecting members. In some embodiments, the connecting members are a plurality of screws, and the RCC assembly 5150 includes corresponding threaded holes for receiving the plurality of screws. In other embodiments, the connection interface 5106 is secured in the RCC assembly 5150 by any other suitable connecting means, such as, but not limited to, welding, adhesive, one or more hooks and latches, or the like. Accordingly, in some embodiments, the connection interface 5106 provides a means for connecting and securing the probe 5102 to the RCC assembly 5150.

In some embodiments, the load cell 5104 is coupled to the probe 5102. In some embodiments, the load cell 5104 is configured to take measurements of pressure or force exerted on the load cell 5104. In some embodiments, because the load cell 5104 is adjacent to or contacting the probe 5102 (e.g., via the connection interface 5106), a force exerted against the concave surface 5103 of the first end 5102a of the probe 5102 (e.g., caused by the concave surface 5103 being pressed against a human head), is registered at the load cell 5104 and can be measured by the load cell 5104.

In some embodiments, the load cell 5104 is a transducer that is used to create an electrical signal whose magnitude is proportional to the force being measured. In some embodiments, wires extending from the load cell 5104 provide electrical signals emanating from the load cell 5104, responsive to the force on the load cell 5104 caused by the probe 5102. During operation, in some embodiments, when the probe 5102 is pressed against a human skull, a force will also be imparted through the connection interface 5106 to the load cell 5104, which can be measured by the load cell 5104.

Accordingly, in some embodiments, the RCC probe device 5100 utilizes the measurements of the load cell 5104 to adjust the pressure exerted by the probe 5102. For example, in some embodiments, the RCC probe device 5100 decreases the force exerted against a human head by the probe 5102 when the pressure measured by the load cell 5104 is determined to be relatively high (e.g., the pressure measurement exceeds a predetermined threshold).

According to various embodiments, the RCC probe device 5100 is capable of fitting and functioning with a table-top robot, such as, but not limited to, the UR3 collaborative table-top robot, and the RCC probe device 5100 is adapted to fit into an end effector of the robot.

In some embodiments, the load cell 5104 indirectly contacts the probe 5102 via the connection interface 5106, or, in other words, the connection interface 5106 is interposed between the probe 5102 and the load cell 5104. Accordingly, in some embodiments, the connection interface 5106 is made of a suitable material for transmitting the pressure forces against the probe 5102 to the load cell 5104, such as, but not limited to, a non-metal material (e.g., polyurethane) and the like. Moreover, in some embodiments, the connection interface 5106 has any suitable shape for transmitting forces to the load cell 5104 from the probe 5102, such as, but not limited to, a bridge or the like.

In some embodiments, the load cell 5104 is positioned to be housed within the RCC assembly 5150. In such embodiments, the RCC assembly 5150 includes an empty space therein to accommodate the load cell 5104 such that the form factor of the RCC probe device 5100 may be minimized. In other embodiments, the load cell 5104 is positioned at any suitable location within the RCC probe device 5100 to measure the force exerted against the probe 5102. In one example, the load cell 5104 is located above the RCC assembly 5150 and below the probe 5102 such that the load cell 5104 interposes the probe 5102 and the RCC assembly 5150. In another example, the load cell 5104 is located below the RCC assembly such that the RCC assembly 5150 interposes the load cell 5104 and the probe 5102.

Figure 48:
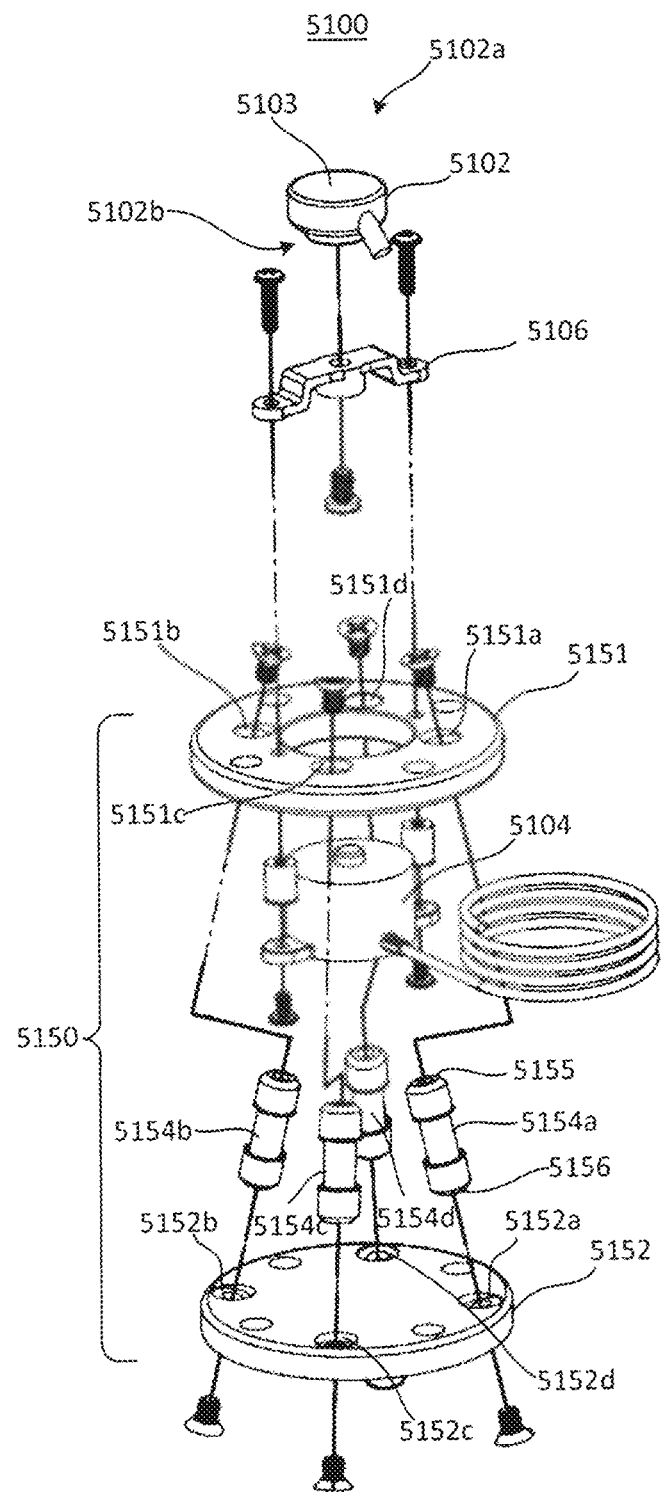
FIG. 48 illustrates an exploded view of a remote center of compliance probe device according to various embodiments.

FIG. 48 illustrates an exploded view of the RCC probe device 5100 according to various embodiments. Referring to FIG. 46, FIG. 47, and FIG. 48, in some embodiments, the RCC assembly 5150 includes a first plate 5151, a second plate 5152, and a plurality of compliant beams 5154a, 5154b, 5154c, and 5154d interposed between the first plate 5151 and the second plate 5152.

In some embodiments, the first plate 5151 has a substantially similar size and shape to the size and shape of the second plate 5152. In some embodiments, the first plate 5151 and the second plate 5152 are circular shapes having substantially similar diameters, with each of the first plate 5151 and second plate 5152 having a center point or origin. In other embodiments, the first plate 5151 and the second plate 5152 are any other suitable shape, such as, but not limited to, squares, triangles, hexagons, or the like. In some embodiments, the first plate 5151 has a circular hole at its center to allow a pathway for a connection of the load cell 5104 to the connection interface 5106 and the probe 5102. In some embodiments, the first plate 5151 and the second plate 5152 each have a center point (e.g., an origin) aligned to be along the same axis. In some embodiments, the first plate 5151 and the second plate 5152 are made from any suitable rigid material, such as, but not limited to, steel, iron, plastic, polyoxymethylene, aluminum, or the like. In some embodiments, the first plate 5151 and the second plate 5152 are made from the same material. In other embodiments, the first plate 5151 and the second plate 5152 are made from different materials.

In some embodiments, the compliant beams include a first compliant beam 5154a, a second compliant beam 5154b, a third compliant beam 5154c, and a fourth compliant beam 5154d. In other embodiments, any suitable number of compliant beams are used, such as, but not limited to, three compliant beams, five compliant beams, or more. In some embodiments, the compliant beams 5154a, 5154b, 5154c, and 5154d are made from any suitable flexible material, such as, but not limited to, polyurethane, rubber, or the like. In some embodiments, the first compliant beam 5154a includes a top end 5155 and a bottom end 5156, and the top end 5155 is coupled to the first plate 5151 and the bottom end 5156 is coupled to the bottom plate 5152. Each of the second compliant beam 5154b, third compliant beam 5154c, and fourth compliant beam 5154d includes a top end 5155 and a bottom end 5156 arranged between the first plate 5151 and the second plate 5152.

In some embodiments, each of the compliant beams 5154a, 5154b, 5154c, and 5154d is affixed to the first plate 5151 (e.g., via the top end 5155) and to the second plate 5152 (e.g., via the bottom end 5156) by any suitable means of securing the compliant beams 5154a, 5154b, 5154c, and 5154d, such as, but not limited to, welding, adhesive, one or more hooks and latches, one or more separate screws, bolting, or the like.

In some embodiments, the first plate 5151 includes a first hole 5151a, a second hole 5151b, a third hole 5151c, and a fourth hole 5151d, and each of the first hole 5151a, the second hole 5151b, the third hole 5151c, and the fourth hole 5151d creates an opening through the body of the first plate 5151. In some embodiments, the top end 5155 of each of the compliant beams 5154a, 5154b, 5154c, and 5154d is coupled to the first plate 5151 via the first hole 5151a, the second hole 5151b, the third hole 5151c, and the fourth hole 5151d, respectively. In some embodiments, corresponding connectors (e.g., screws) are positioned through the holes 5151a, 5151b, 5151c, and 5151d and couple to the top end 5155 of each of the compliant beams 5154a, 5154b, 5154c, and 5154d for securing the compliant beams 5154a, 5154b, 5154c, and 5154d within the RCC assembly 5150.

In some embodiments, the second plate 5152 includes a first via 5152a, a second via 5152b, a third via 5152c, and a fourth via 5152d, and each the first via 5152a, the second via 5152b, the third via 5152c, and the fourth via 5152d creates an opening through the body of the second plate 5152. In some embodiments, the bottom end 5156 of each of the compliant beams 5154a, 5154b, 5154c, and 5154d is coupled to the second plate 5152 via the first via 5152a, the second via 5152b, the third via 5152c, and the fourth via 5152d, respectively. In some embodiments, corresponding connectors (e.g., screws) are positioned through the vias 5152a, 5152b, 5152c, and 5152d and couple to the bottom end 5156 of each of the compliant beams 5154a, 5154b, 5154c, and 5154d for securing the compliant beams 5154a, 5154b, 5154c, and 5154d within the RCC assembly 5150.

In some embodiments, the holes 5151a, 5151b, 5151c, and 5151d of the first plate 5151 are positioned along a first circumference of the first plate 5151 and the vias 5152a, 5152b, 5152c, and 5152d of the second plate 5152 are positioned along a second circumference of the second plate 5152, and the first circumference has a smaller diameter than that of the second circumference. In other words, in some embodiments, the holes 5151a, 5151b, 5151c, and 5151d are positioned closer to the center point of the first plate 5151 than the vias 5152a, 5152b, 5152c, and 5152d are positioned with respect to the center point of the second plate 5152. In other words, each of the holes 5151a, 5151b, 5151c, and 5151d has a smaller radial distance from the center point of the first plate 5151 than that of each of the vias 5152a, 5152b, 5152c, and 5152d from the center point of the second plate 5152.

Accordingly, in some embodiments, due to the difference in radial distances between the holes 5151a, 5151b, 5151c, and 5151d and the vias 5152a, 5152b, 5152c, and 5152d, the compliant beams 5154a, 5154b, 5154c, and 5154d are angled or tilted inwards towards the center point of the first plate 5151. In some embodiments, the degree of the angle or tilt is dependent on the difference in radial distances between the holes 5151a, 5151b, 5151c, and 5151d and the vias 5152a, 5152b, 5152c, and 5152d. For example, the greater the difference in the radial distances between the holes 5151a, 5151b, 5151c, and 5151d and the vias 5152a, 5152b, 5152c, and 5152d, the greater the degree of tilt is of the compliant beams 5154a, 5154b, 5154c, and 5154d.

In some embodiments, the compliant beams 5154a, 5154b, 5154c, and 5154d are adjusted or manufactured for particular parameter characteristics, such as, but not limited to, shore hardness (hardness of the material), tensile strength (point at which the material transitions from elastic to plastic deformation), elongation (change in length over initial length at the tensile strength), modulus of elasticity (slope of the curve in the elastic section of a stress/strain curve), length, and diameter. In one example, the compliant beams 5154a, 5154b, 5154c, and 5154d have a shore hardness of about 60 A, a tensile strength of about 4100 psi, an elongation of 500%, a modulus of elasticity of 820 psi, a length of 1 in, and diameter 0.25 in. In some embodiments, the compliant beams 5154a, 5154b, 5154c, and 5154d have a shore hardness in a range from about 60 A to about 80 A, a tensile strength in a range from about 4100 psi to about 4600 psi, an elongation in a range from about 450% to about 500%, and a modulus of elasticity in a range from about 820 psi to about 1020 psi.

According to various embodiments, the RCC assembly 5150 of the RCC probe device 5100 is configured to adjust a center of compliance of the RCC probe device 5100 (e.g., by adjusting the shape, angle of tilt, thickness, length, etc. of the compliant beams 5154a, 5154b, 5154c, and 5154d). In particular embodiments, the connection of the RCC assembly 5150 to the probe 5102 is configured to adjust the center of compliance to be at the tip of the probe 5102, on the scanning surface, or beneath the scanning surface such that the scanning surface interposes the probe 5102 and the center of compliance.

In some embodiments, the center of compliance is adjusted from being at the second end 5102b of the probe 5102 (without the RCC assembly 5150) to being at the first end 5102a of the probe 5102 or beyond (with the RCC assembly 5150 connected to the probe 5102). In some embodiments, the precise location of the remote center of compliance is determined by the design of the RCC assembly 5150, such as, but not limited to, the number and material of the compliant beams, the angle of tilt of the compliant beams, the locations of the compliant beams, the length of the compliant beams, thickness of the compliant beams, and so on.

Figure 49:
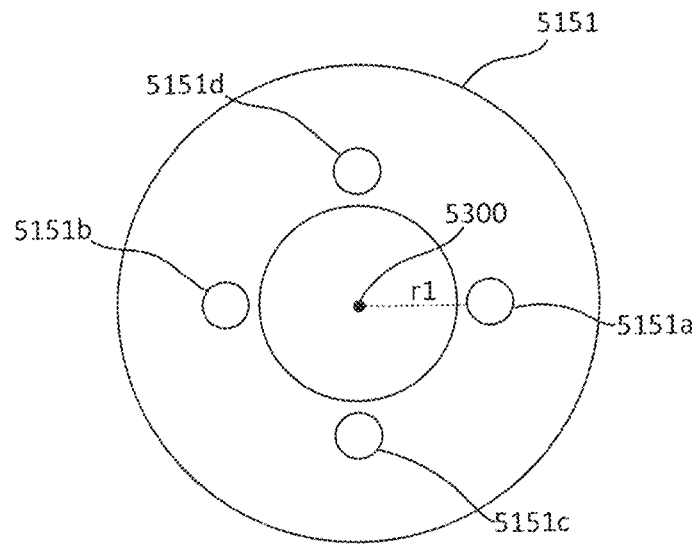
FIG. 49 illustrates a top view of a first plate of a remote center of compliance probe device according to various embodiments.
Figure 50:
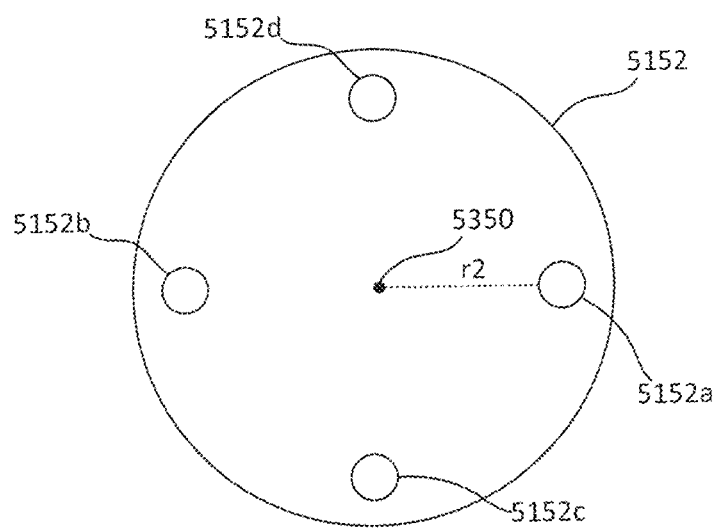
FIG. 50 illustrates a top view of a second plate of a remote center of compliance probe device according to various embodiments.

FIG. 49 illustrates a top view of the first plate 5151 of the RCC probe device 5100 according to various embodiments. FIG. 50 illustrates a top view of the second plate 5152 of the RCC probe device 5100 according to various embodiments.

Referring to FIGS. 54A-56B, in some embodiments, the first plate 5151 has an origin or center point 5300 and the second plate 5152 has an origin or center point 5350. In some embodiments, the center points 5300 and 5350 are aligned such that a single axis passes through both the center point 5300 of the first plate 5151 and the center point 5350 of the second plate 5152.

In some embodiments, each of the holes 5151a, 5151b, 5151c, and 5151d surround the center point 5300 of the first plate 5300, and each of the holes 5151a, 5151b, 5151c, and 5151d are spaced from adjacent holes at equal distances. In other words, the holes 5151a, 5151b, 5151c, and 5151d are spaced along a circumference of the first plate 5151 at equal intervals. In some embodiments, each of the holes 5151a, 5151b, 5151c, and 5151d are a same first radial distance or first radius r1 from the center point 5300.

In some embodiments, each of the vias 5152a, 5152b, 5152c, and 5152d surround the center point 5350 of the second plate 5152, and each of the vias 5152a, 5152b, 5152c, and 5152d are spaced from adjacent vias at equal distances. In other words, the vias 5152a, 5152b, 5152c, and 5152d are spaced along a circumference of the second plate 5152 at equal intervals. In some embodiments, each of the vias 5152a, 5152b, 5152c, and 5152d are a same second radial distance or second radius r2 from the center point 5350.

In some embodiments, the first radial distance r1 is less than the second radial distance r2, such that the compliant beams 5154a, 5154b, 5154c, and 5154d are tilted inwards towards the center points 5300 and 5350 when coupled to the first plate 5151 (via the holes 5151a, 5151b, 5151c, and 5151d) and to the second plate 5152 (via the vias 5152a, 5152b, 5152c, and 5152d). The degree or angle of tilt of the compliant beams 5154a, 5154b, 5154c, and 5154d is dependent on the difference between the first radial distance r1 and the second radial distance r2. In other embodiments, the first radial distance r1 is equal to the second radial distance r2, or the first radial distance r1 is greater than the second radial distance r2.

In some embodiments, the first radial distance r1 is less than the second radial distance r2 such that the angle of tilt of each of the compliant beams 5154a, 5154b, 5154c, and 5154d is about 12.5 degrees inwards toward the center points 5300 and 5350, with respect to a lateral upper surface of the second plate from which the compliant beams 5154a, 5154b, 5154c, and 5154d extend towards the first plate 5151. In some embodiments, the distance from a center axis to centers of the compliant beams 5154a, 5154b, 5154c, and 5154d (e.g., the distance between an axis that passes through the center points 5300 and 5350 and a midpoint of a compliant beam along the length of the compliant beam) is about 0.9 inches. In some embodiments, a projection ratio (ratio of lengths) of the compliant beams 5154a, 5154b, 5154c, and 5154d is about 1.516.

Figure 51:
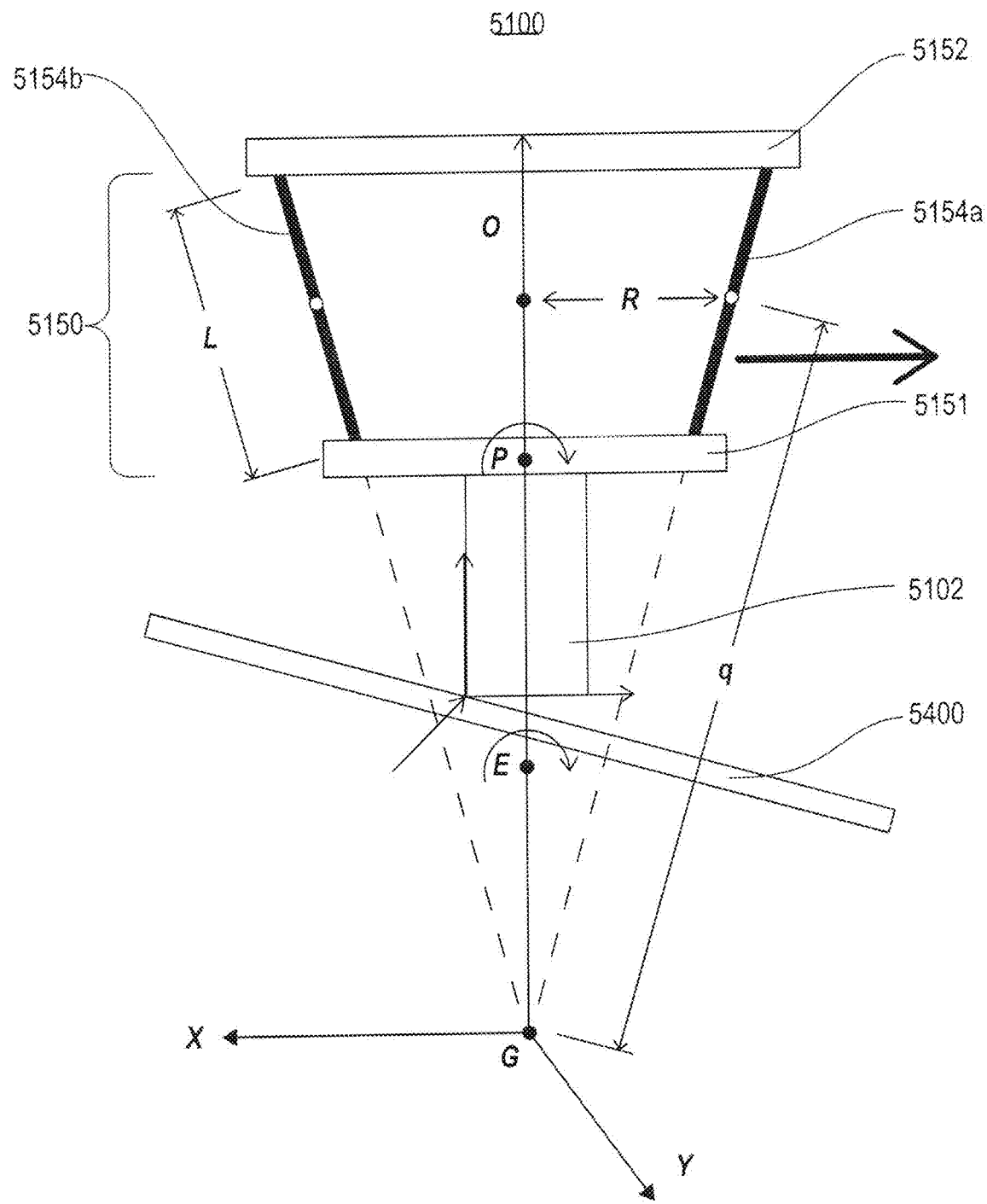
FIG. 51 illustrates a free body diagram including a remote center of compliance probe device according to various embodiments.

FIG. 51 illustrates a free body diagram including the RCC probe device 5100 according to various embodiments. Referring to FIGS. 54A-57, the diagram illustrates the function of the RCC probe device 5100. The free body diagram illustrates the RCC probe device 5100 traveling laterally along a tilted scanning surface 5400 (e.g., skin or a head of a person). The RCC probe device 5100 travels laterally from left to right, or laterally along the decline of the scanning surface 5400.

In some embodiments, the RCC assembly 5150 provides the remote center of compliance E about which the probe 5102 may rotate, and the remote center of compliance E may be located beneath the scanning surface 5400. As such, in some embodiments, due to the remote center of compliance E being positioned beyond the probe 5102, the probe, no matter where placed, can align normal to the scanning surface 5400 (e.g., such that substantially all of the concave surface 5103 of the probe 5102 contacts the scanning surface 5400). In various embodiments, a force about the remote center of compliance E twists the probe 5102 into alignment with the scanning surface 5400.

In some embodiments, in providing the remote center of compliance E, one or more of the compliant beams 5154a, 5154b, 5154c, and 5154d of the RCC assembly 5150 will twist and/or bend to allow the probe 5102 to align such that the probe 5102 rotates into the scanning surface 5400. As such, in some embodiments, when a linear misalignment occurs, a contact force translates the probe away, and when an angular misalignment occurs, a contact moment turns the probe 5102 about the remote center of compliance E, allowing for the probe 5102 to align normal with the scanning surface 5400. Accordingly, in various embodiments, the probe 5102, with the aid of the attached RCC assembly 5150, will auto-align normal to the scanning surface 5400 along which the probe 5102 is sliding.

In some embodiments, the behavior of the RCC probe device 5100 shown in FIG. 51 can be represented by the following equations. In the following equations for a particular rod or beam, L is the longitudinal length
E is the modulus of elasticity
A is the cross-sectional area
$A_{sx}$ is the shear area in the x direction
$A_{sy}$ is the shear area in the y direction $I_x$ is the area moment of inertia in the x direction
$I_y$ is the area moment of inertia in the y direction
v is Poisson's ratio
G is the shear modulus, which is equal to E/2(1+v)
J is the polar moment of inertia
O is the origin point of a beam in the longitudinal length direction
R is the distance from a center axis to a midpoint of a compliant beam $$\lambda_{zy} = \lambda_z = \lambda_y = \frac{12EI}{L^3(1+\Phi)} \quad (1)$$

$$\lambda_z = \frac{AE}{L} \quad (2)$$

$$\mu_{zy} = \mu_z = \mu_y = \frac{EI}{L} \quad (3)$$

$$\mu_z = \frac{GJ}{L} \quad (4)$$

$$p = \frac{EO}{R} = \frac{\lambda_z \cos^2\theta + \lambda_{y+\lambda_z sin^2\theta}}{(\lambda_z - \lambda_x)\cos\theta\sin\theta} \quad (5)$$

$$\Phi_z = \frac{12EI_y}{GA_{xz}L^2} \quad (6)$$

$$\Phi_y = \frac{12EI_z}{GA_{xy}L^2} \quad (7)$$

The above used terms, including "attached," "connected," "secured," and the like are used interchangeably. In addition, while certain embodiments have been described to include a first element as being "coupled" (or "attached," "connected," "fastened," etc.) to a second element, the first element may be directly coupled to the second element or may be indirectly coupled to the second element via a third element.

The algorithmic subject matter and the operations described in this specification can be implemented in digital electronic circuitry, or in computer software, firmware, or hardware, including the structures disclosed in this specification and their structural equivalents, or in combinations of one or more of them. The algorithmic subject matter described in this specification can be implemented as one or more computer programs, e.g., one or more circuits of computer program instructions, encoded on one or more computer storage media for execution by, or to control the operation of, data processing apparatuses. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). The algorithmic operations described in this specification can be implemented as operations performed by a data processing apparatus on data stored on one or more computer-readable storage devices or received from other sources.

The terms "data processing system" "computing device" "component" or "data processing apparatus" encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The algorithmic processes and logic flows described in this specification can be performed by one or more programmable processors executing one or more computer programs (e.g., components or modules of the system 1040 or system 1080) to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system such as system 1040 or system 1080 can include clients and servers. A client and server are generally remote from each other and typically interact through a communication network. The relationship of client and server arises by virtue of computer programs running on the respective computers and having a client-server relationship to each other. In some implementations, a server transmits data (e.g., data packets representing a content item) to a client computing device (e.g., for purposes of displaying data to and receiving user input from a user interacting with the client computing device). Data generated at the client computing device (e.g., a result of the user interaction) can be received from the client computing device at the server.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an embodiment," "some embodiments," "various embodiments," "one embodiment," or the like are not necessarily mutually exclusive and are intended to indicate that a particular feature, structure, or characteristic described in connection with the embodiment may be included in at least one implementation or embodiment. Such terms as used herein are not necessarily all referring to the same embodiment. Any embodiment may be combined with any other embodiment, inclusively or exclusively, in any manner consistent with the aspects and embodiments disclosed herein.

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. For example, components of the data processing system 105 need not be separate components, and one component can include other components. Processors of one or more computing devices (e.g., servers) can include or execute components of the data processing system 105. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A device comprising a processor configured to:
control a robotic system to autonomously position a transducer at a plurality of locations adjacent a subject's skull;
register a position of the transducer relative to the subject's skull; and
autonomously locate a window on the subject's skull within which an artery can be located, from which artery a signal can be returned to the transducer, the signal having an energy level exceeding a predefined threshold, wherein the processor autonomously locates the window by:
receiving the signaling at the plurality of locations starting from an initial location, wherein the initial location of the plurality of locations is a seed point selected from a plurality of seed points stored in a database accessible by the processor, the seed point represents a location of the transducer that has a high likelihood of locating a window;
determining a candidate location of the transducer based on the signal; and
maximizing signal strength with respect to the candidate location of the transducer by:
directing the transducer to insonate at multiple depths and angles at the candidate location, wherein the signal comprises a plurality of signals, each of the plurality of signals returned at each of the depths and each of the angles, and directing the transducer to insonate at multiple angles comprises re-orienting the transducer;
determining one of the plurality of depths and one of the plurality of angles by interpreting the plurality of signals; and controlling the robotic system to position the transducer at the one of the plurality of depths and the one of the plurality of angles.

2. The device of claim 1 wherein the processor is further configured to: cause the robotic system to autonomously locate within the window the signal returned to the transducer representative of blood flow within the artery, the signal having an energy level exceeding the predefined threshold.

3. The device of claim 1, wherein the processor is further configured to record in a database a plurality of locations of the transducer as the robotic system autonomously positions the transducer.

4. The device of claim 3, wherein the processor is further configured to record in a database a plurality of energy levels of signals returned to the transducer as the robotic system autonomously positions the transducer.

5. The device of claim 3, wherein the device further comprises a robotic mechanism configured to move the transducer in multiple axes, and the processor is further configured to control pan, tilt, and Z axis positions of the robotic mechanism.

6. The device of claim 1, wherein the processor is further configured to execute a search algorithm stored on non-transitory computer readable media, wherein the search algorithm uses the signal returned to the transducer to position the transducer.

7. The device of claim 1, further comprising a database of previously measured locations with respect to the subject's skull stored on non-transitory computer readable media accessible by the processor, which database of previously measured locations is used by the processor to position the transducer.

8. The device of claim 1, wherein the processor is configured to execute a search algorithm, the search algorithm being configured to use dynamic dwell time at a plurality of locations searched to position the transducer.

9. The device of claim 1, wherein the robotic system further comprises a five degree of freedom robotic mechanism.

10. The device of claim 1, wherein the robotic system further comprises a five degree of freedom robotic mechanism configured to move the transducer in multiple axes simultaneously.

11. The device of claim 1, further comprising a robotic headset within which the transducer is mounted.

12. The device of claim 1, wherein the processor is further configured to cause the robotic system to build a vascular map of the brain inside the subject's skull.

13. The device of claim 1, wherein said transducer comprises an ultrasound probe.

14. A robotic imaging device comprising:
a transducer;
a processor in communication with the transducer, the processor configured to receive and process data from the transducer;
a robotic mechanism controlled by the processor configured to move the transducer to scan for and locate a window in a skull of a subject; and
wherein the processor is configured to:
register a position of the transducer with respect to the skull of a subject; autonomously control the robotic mechanism to search for; and
locate a transcranial Doppler (TCD) signal within the window in the skull of the subject, said TCD signal having an energy level exceeding a predefined threshold, wherein the processor autonomously locates the window by:
receiving the TCD signal at the plurality of locations starting from an initial location, wherein the initial location of the plurality of locations is a seed point selected from a plurality of seed points stored in a database accessible by the processor, the seed point represents a location of the transducer that has a high likelihood of locating a window;
determining a candidate location based on the TCD signal of the transducer; and
maximizing TCD signal strength with respect to the candidate location of the transducer by:
directing the transducer to insonate at multiple depths and angles at the candidate location, wherein the TCD signal comprises a plurality of TCD signals, each of the plurality of TCD signals returned at each of the depths and each of the angles, and directing the transducer to insonate at multiple angles comprises re-orienting the transducer;
determining one of the plurality of depths and one of the plurality of angles by interpreting the plurality of TCD signals; and
controlling the robotic system to position the transducer at the one of the plurality of depths and the one of the plurality of angles.

15. The robotic imaging device of claim 14, wherein the processor is further configured to execute a search algorithm stored on non-transitory computer readable media, wherein the search algorithm uses the TCD signal returned to the transducer to position the transducer.

16. The robotic imaging device of claim 14 wherein the processor is further configured to execute a search algorithm stored on non-transitory computer readable media, which search algorithm employs dynamic dwell time at a plurality of search locations to position the transducer.

17. The robotic imaging device of claim 14 further comprising a visual window guide, wherein the robotic mechanism is further configured to use the visual window guide for initial registration.

18. The robotic imaging device of claim 14, wherein the robotic mechanism is further configured to move in at least two axes simultaneously.

19. The robotic imaging device of claim 14, wherein the robotic mechanism is further configured to comprise a five degree of freedom robotic mechanism configured to move the transducer in multiple axes simultaneously.

20. The robotic imaging device of claim 14, wherein the robotic mechanism is further configured to comprise a six degree of freedom robotic mechanism.

21. The robotic imaging device of claim 14, wherein the robotic mechanism is further configured to comprise at least a four degree of freedom robotic mechanism.

22. The robotic imaging device of claim 14, further comprising a feedback mechanism used to adjust the position of the transducer with respect to the skull of the subject due to subject movement.

* * * * *